United States Patent
Tyan et al.

(10) Patent No.: US 10,527,613 B2
(45) Date of Patent: Jan. 7, 2020

(54) BIOMARKER DETECTION METHODS AND SYSTEMS AND KITS FOR PRACTICING SAME

(71) Applicant: The Board of Trustees of the Leland Stanford Junior University, Stanford, CA (US)

(72) Inventors: Dolly B. Tyan, Palomar Park, CA (US); Ge Chen, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 427 days.

(21) Appl. No.: 15/336,439

(22) Filed: Oct. 27, 2016

(65) Prior Publication Data
US 2017/0131268 A1    May 11, 2017

Related U.S. Application Data

(60) Provisional application No. 62/253,549, filed on Nov. 10, 2015.

(51) Int. Cl.
   G01N 33/50         (2006.01)
   G01N 33/543        (2006.01)
   C12N 5/00          (2006.01)

(52) U.S. Cl.
   CPC ..... *G01N 33/54313* (2013.01); *C12N 5/0075* (2013.01); *C12N 2531/00* (2013.01); *G01N 2333/705* (2013.01)

(58) Field of Classification Search
   None
   See application file for complete search history.

(56) References Cited

U.S. PATENT DOCUMENTS

| | | | |
|---|---|---|---|
| 4,708,871 A | 11/1987 | Geysen | |
| 5,035,995 A | 7/1991 | Taguchi et al. | |
| 5,270,169 A | 12/1993 | Chang et al. | |
| 5,851,829 A | 12/1998 | Marasco et al. | |
| 5,965,371 A | 10/1999 | Marasco et al. | |
| 6,146,589 A | 11/2000 | Chandler | |
| 6,150,122 A | 11/2000 | Lee et al. | |
| 6,159,748 A | 12/2000 | Hechinger | |
| 6,514,714 B1 | 2/2003 | Lee et al. | |
| 7,332,349 B2 | 2/2008 | Yang et al. | |
| 8,828,664 B2 | 9/2014 | Fekete et al. | |
| 2005/0059095 A1 | 3/2005 | Yang et al. | |
| 2005/0277158 A1 | 12/2005 | Chen | |
| 2005/0282172 A1 | 12/2005 | Liu | |
| 2007/0042414 A1 | 2/2007 | Hutchens et al. | |
| 2007/0042505 A1 | 2/2007 | Israel et al. | |
| 2009/0075378 A1* | 3/2009 | Horlick | C07K 16/00 435/375 |
| 2011/0281757 A1 | 11/2011 | Tyan et al. | |
| 2012/0070834 A1 | 3/2012 | Greinacher et al. | |
| 2012/0065092 A1 | 5/2012 | Wai et al. | |
| 2015/0240229 A1* | 8/2015 | Gjerde | C12N 5/061 435/177 |
| 2016/0033524 A1 | 2/2016 | Tyan et al. | |
| 2016/0041185 A1 | 2/2016 | Tyan et al. | |
| 2018/0052154 A1* | 2/2018 | Stoner | G01N 33/538 |

FOREIGN PATENT DOCUMENTS

| | | |
|---|---|---|
| CN | 1423130 | 6/2003 |
| CN | 1444044 | 9/2003 |
| CN | 1766616 | 5/2006 |
| EP | 0204522 | 12/1986 |
| JP | 61245060 | 10/1986 |
| JP | 63109371 | 5/1988 |
| JP | 1501571 A | 6/1989 |
| JP | 2001521909 | 11/2001 |
| JP | 2008100986 | 5/2008 |
| JP | 2009080019 | 4/2009 |
| WO | WO2008035047 | 3/2008 |
| WO | WO2010138456 | 12/2010 |
| WO | WO2013029181 | 3/2013 |

OTHER PUBLICATIONS

Lewis et al., Microparticle surface modifidations targeting dendritic cells for non-activiating applications, Biomaterials, 33, 2012, pp. 7221-7232. (Year: 2012).*
Ahrens et al., Receptor-Mediated Endocytosis of Iron-Oxide Particles Provides Efficient Labeling of Dendritic Cells for In Vivo MR Imaging, Magnetic Resonance in Medicine 19, 2003, pp. 1006-1013. (Year: 2003).*
Kempf et al., Improved Stimulation of Human Dendritic Cells by Receptor Engagement with Surface-modified Microparticles, Journal of Drug Testing, vol. 11, 1, 2003, pp. 11-18. (Year: 2003).*
Anjaneyulu & Staros (1987) "Reactions of N-Hydroxysulfosuccinimide Active Esters" *Int. J. Pept. Protein Res.* 30(1):117-124.
Billen et al. (2008) "Luminex donor-specific crossmatches" Tissue antigens 71(6):507-513.
Brinkley (1992) "A Brief Survey of Methods for Preparing Protein Conjugates with Dyes, Haptens, and Cross-Linking Reagents" *Bioconjug. Chem.* 3(1):2-13.
Chen et al. (2011) "Novel C1q assay reveals a clinically relevant subset of human Leukocyte antigen antibodies independent of immunoglobulin G strength on single antigen beads" *Hum. Immunol.* 72(10):849-858.

(Continued)

*Primary Examiner* — Gary Counts
(74) *Attorney, Agent, or Firm* — Edward J. Baba; Bozicevic, Field & Francis LLP

(57) ABSTRACT

Aspects of the present disclosure include methods that include co-culturing a cell and a microparticle that includes a capture ligand, in a culture medium under conditions in which a biomarker produced by the cell is bound by the capture ligand. Such methods may further include detecting (e.g., by flow or mass cytometry) complexes that include the microparticle, the capture ligand, the biomarker, and a detection reagent. The methods may further include determining the proportion or number of cells among a heterogeneous cell population that produced the biomarker and/or the level of biomarker secreted by such cells. Compositions, systems and kits are also provided.

27 Claims, 37 Drawing Sheets

(56) References Cited

OTHER PUBLICATIONS

Chen et al. (2013) "C1q Assay for the Detection of Complement Fixing Antibody to HLA Antigens" Methods in Molecular Biology 1034:305-311.
Elshal & Mccoy (2006) "Multiplex Bead Array Assays: Performance Evaluation and Comparison of Sensitivity to ELISA" Methods, 38(4):317-323.
Geysen et al. (1986) "A priori Delineation of a Peptide Which Mimics a Discontinuous Antigenic Determinant" *Mol. Immunol.* 23(7):709-715.
Geysen et al. (1984) "Use of Peptide Synthesis to Probe Viral Antigens for Epitopes to a Resolution of a Single Amino Acid" *Proc. Natl. Acad. Sci. USA* 81(13):3998-4002.
Hashida et al. (1984) "More Useful Maleimide Compounds for the Conjugation of Fab' to Horseradish Peroxidase through Thiol Groups in the Hinge" *J. Appl. Biochem.* 6(1-2):56-63.
International Search Report for PCT Appln No. PCT/US2009/065984 datd Mar. 30, 2010, 2009.
Kishore et al., (1997) "Release of calreticulin from neutrophils may alter C1q-mediated immune functions" Biochem J. 322(pt 2):543-550.
Kishore et al., (2003) "Modular Organization of the Carboxyl-Terminal, Globular Head Region of Human C1q A, B, and C Chains" Journal of Immunology, 171(2):812-820.
Kishore et al. (2004) "C1q and Tumor Necrosis Factor Superfamily: Modularity and Versatility" *Trends Immunol.* 25(10):551-561.

Pei et al. (1998) "Simultaneous HLA Class I and Class II antibodies screening with flow cytometry" *Human Immunology* 59(5):313-322.
Smith et al. (1994) "β-Sheet Secondary Structure of the Trimeric Globular Domain of C1q of Complement and Collagen Types VIII and X by Fourier-Transform Infrared Spectroscopy and Averaged Structure Predictions" *Biochem. J.* 301(Pt 1):249-256.
Smith et al. (2007) "C4d Fixing, Luminex Binding Antibodies—A New Tool for Prediction of Graft Failure after Heart Transplantation" *Am. J. Transplant.* 7(12):2809-2815.
Saunkratay et al. (1999) "Mechanism of complement-dependent haemolysis via the lectin pathway: role of the complement regulatory proteins" *Clin Exp Immunol* 117:442-448.
Steinberger et al. (Journal of Leukocyte Biology 71.1 (2002): 133-140).
Wahrmann et al. (2003) "Flow Cytometry Based Detection of HLA Alloantibody Mediated Classical Complement Activation" *J. Immunol. Methods.* 275(1/2):149-160.
Wahrmann et al. (2005) "[C4d]FlowPRA Screening—A Specific Assay for Selective Detection of Competent-Activating Anti-HLA Alloantibodies," *Hum. Immunol.* 66(5):526-534.
Yabu et al., (2011) "C1q-fixing human leukocyte antigen antibodies are specific for predicting transplant glomerulopathy and late graft failure after kidney transplant" Transplantation, 91(3):342-347.
Schønau et al. (1998) "A one-step solid phase immunoassay for simultaneous detection of serum IgG and IgM antibodies to Borrelia burgdorferi." Journal of immunological methods 218.1-2 :9-17.

* cited by examiner

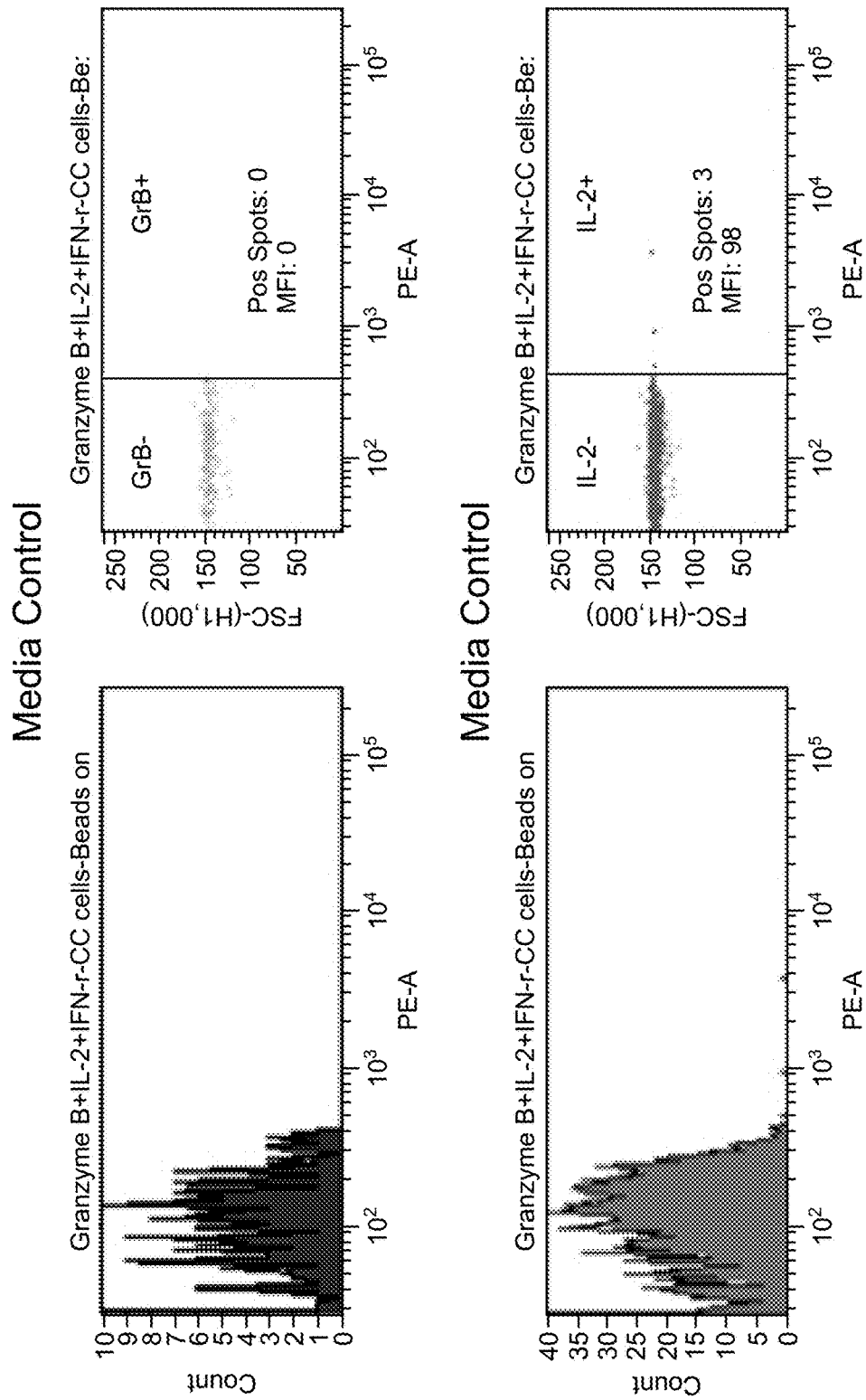

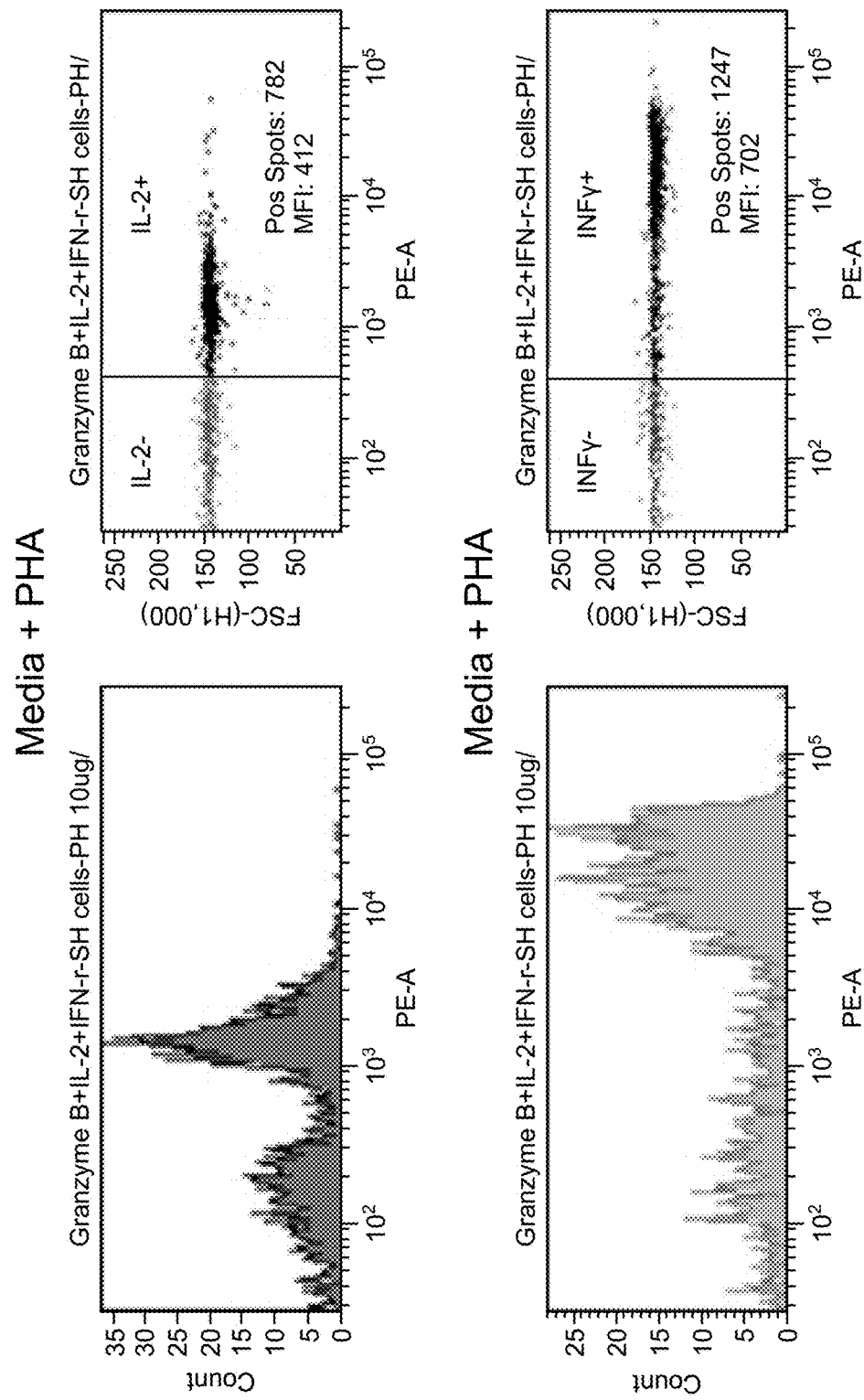

FIG. 10
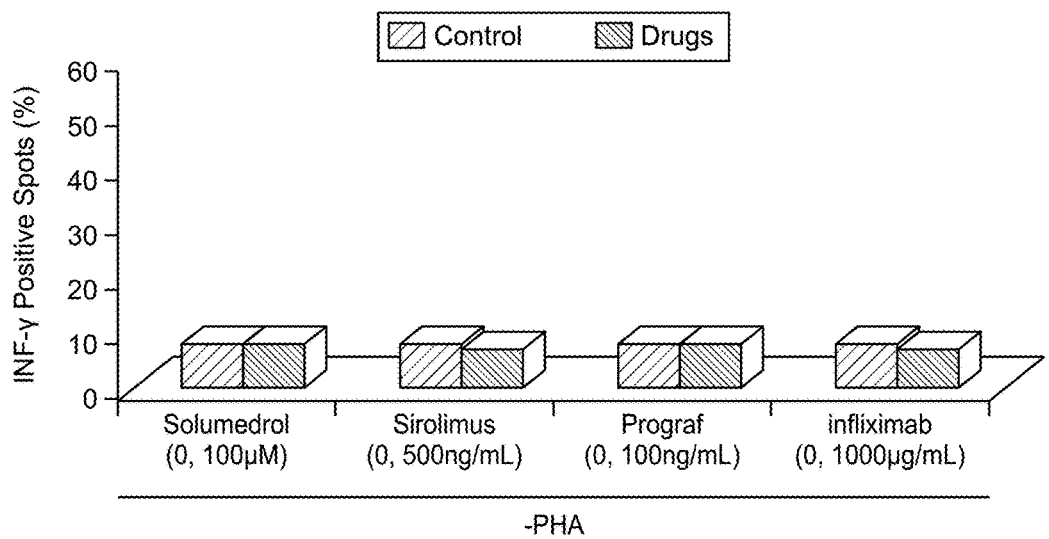
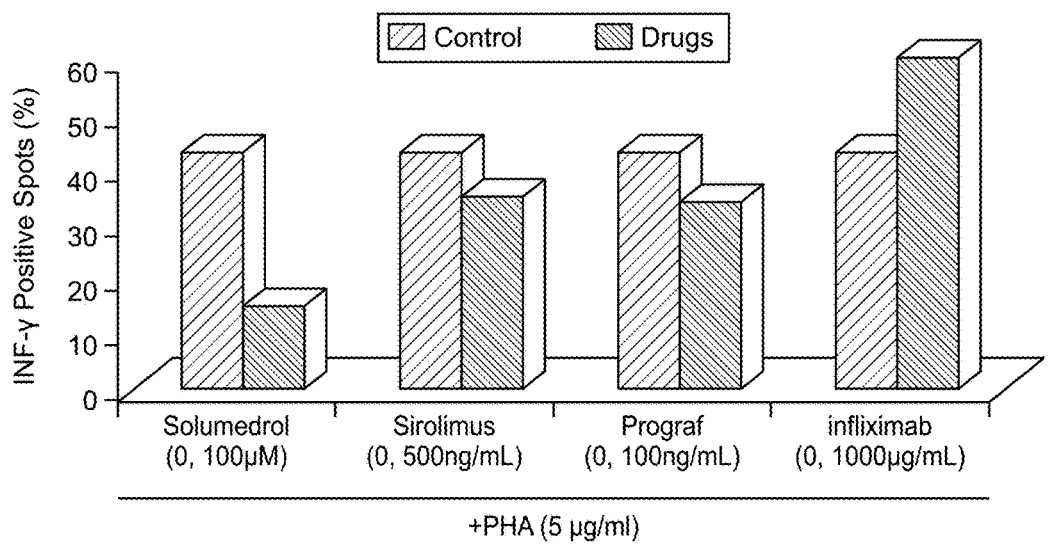

FIG. 11
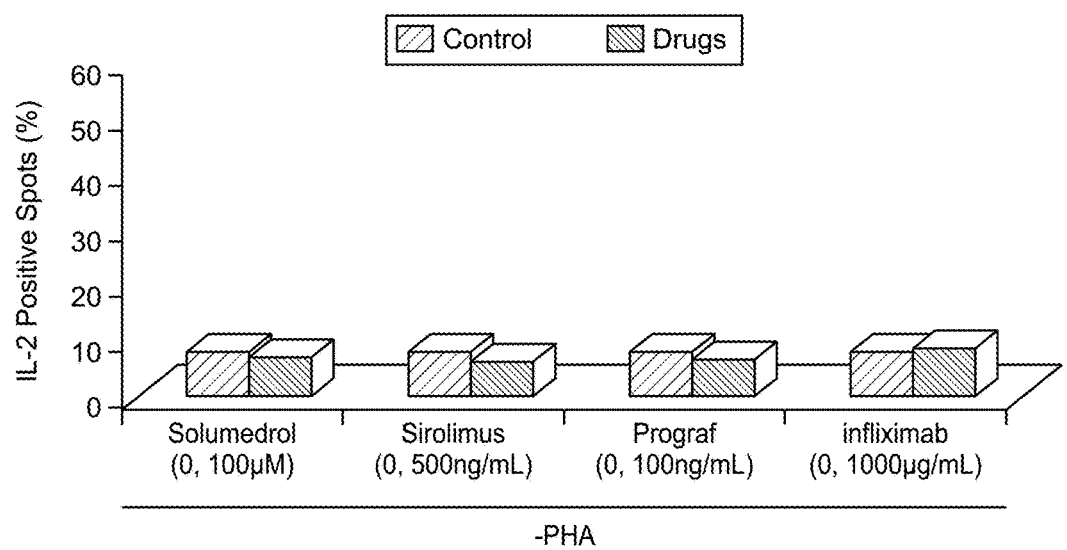
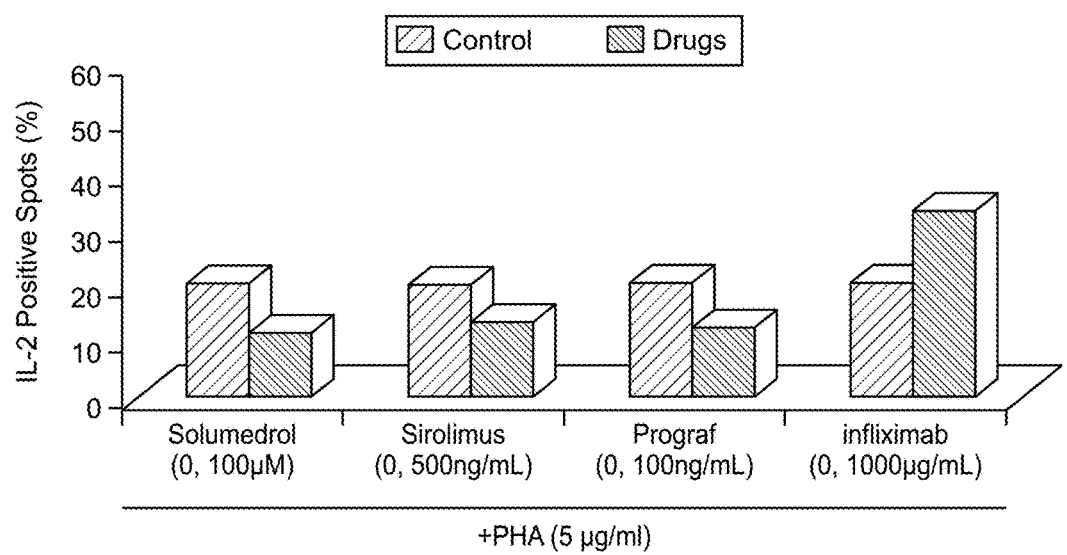

FIG. 12
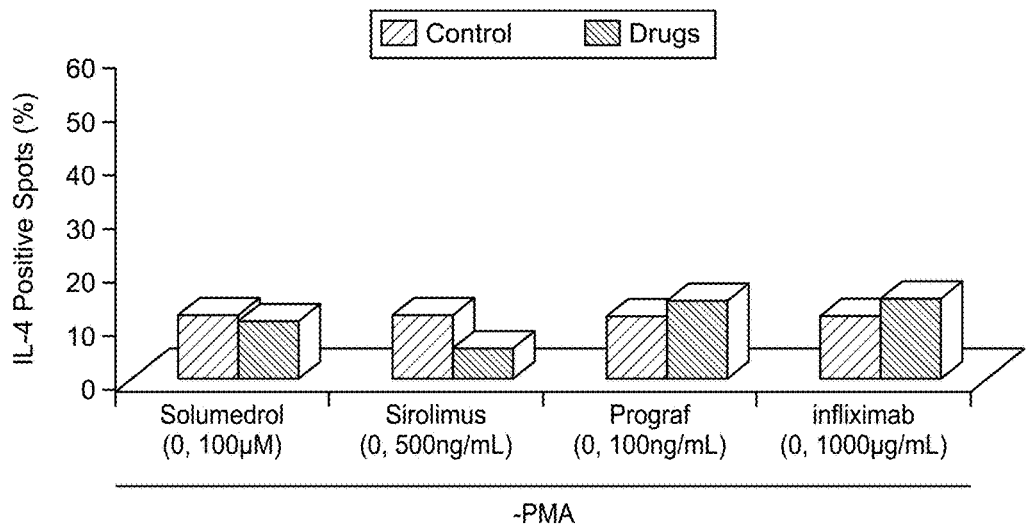
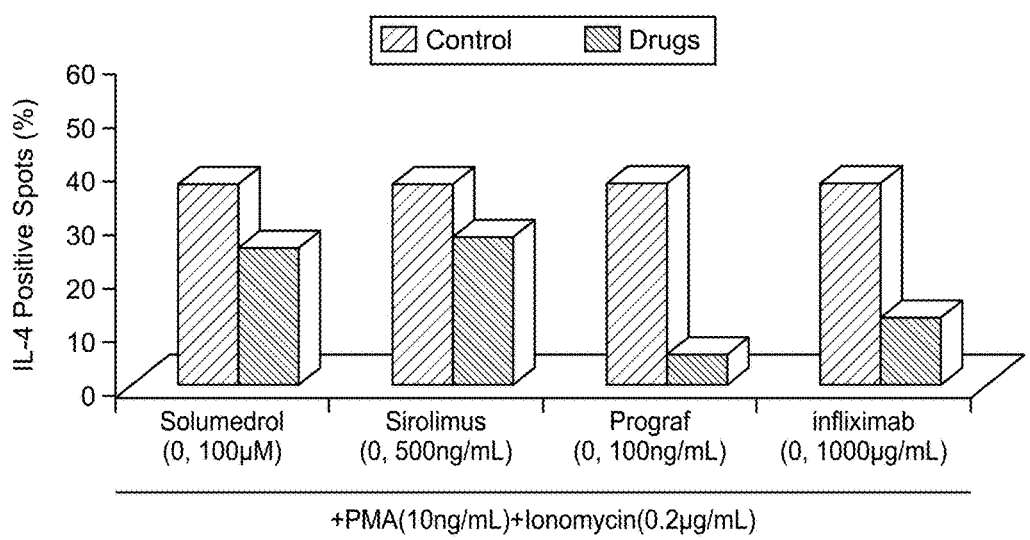

FIG. 13
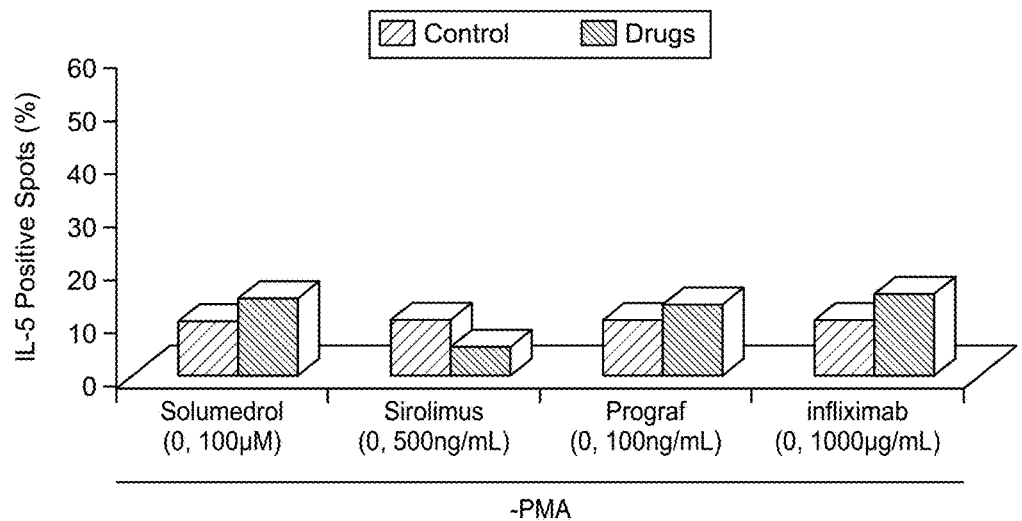
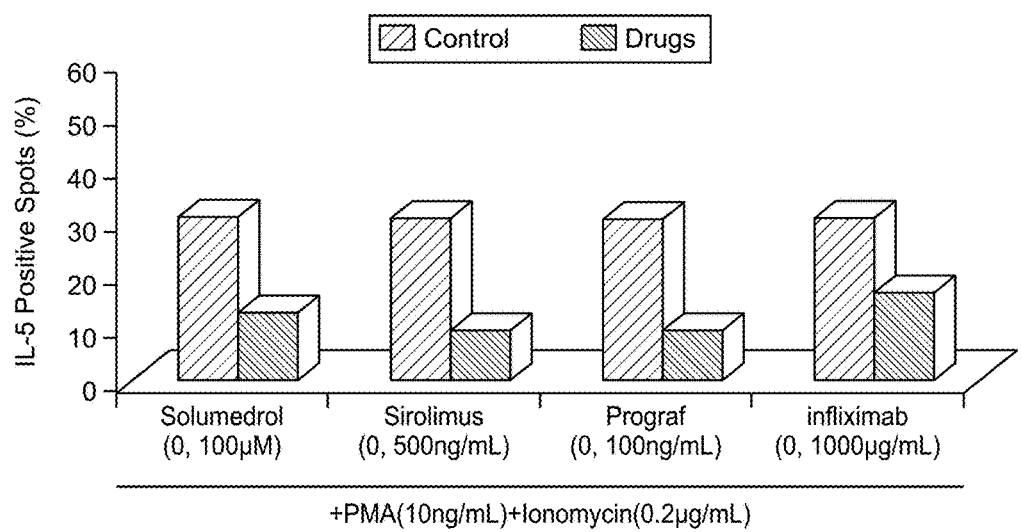

FIG. 14
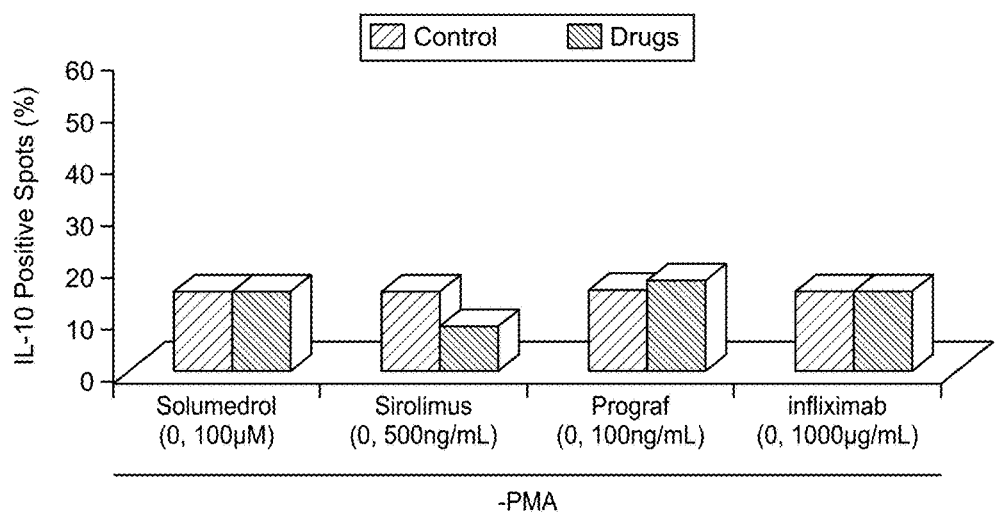
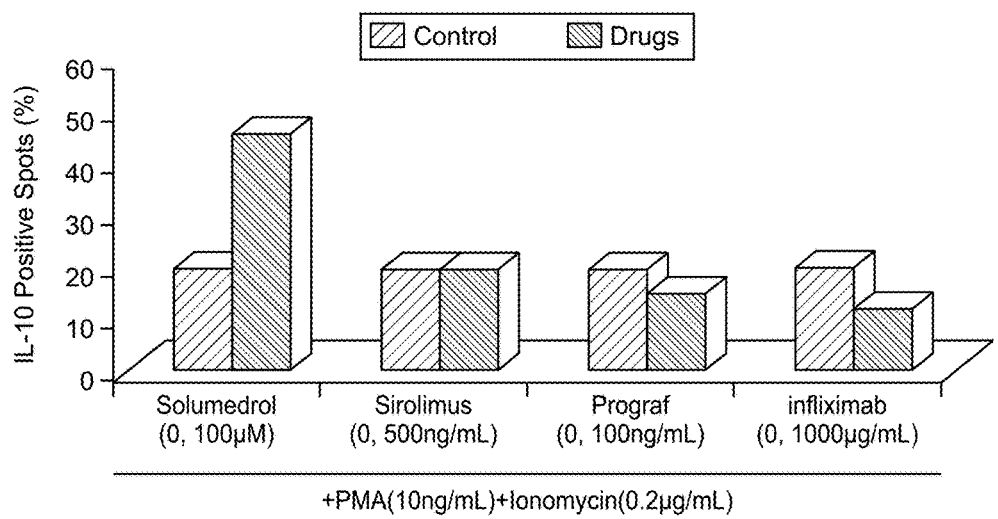

PHA: Phytohemaglutinin; Fluzone: Influenza Virus Vaccine; MTB06R: Mycobacterium tuberculosis antigen 6KDa;
MTB16R: Mycobacterium tuberculosis antigen 16KDa; TTOX15: Purified Tetanus Toxid protein;
DTOX15: Diphtheria Toxoid protein; NY-ESO-1: Testis cancer antigen;

PHA: Phytohemaglutinin; Fluzone: Influenza Virus Vaccine; MTB06R: Mycobacterium tuberculosis antigen 6KDa;
MTB16R: Mycobacterium tuberculosis antigen 16KDa; TTOX15: Purified Tetanus Toxid protein;
DTOX15: Diphtheria Toxoid protein; NY-ESO-1: Testis cancer antigen;

P+I: PMA(Phorbol myristate acetate, 50ng/mL) + Ionomycin(1μg/mL); Fluzone: Influenza Virus Vaccine; MTB06R: Mycobacterium tuberculosis antigen 6KDa; MTB16R: Mycobacterium tuberculosis antigen 16KDa; TTOX15: Purified Tetanus Toxid protein; DTOX15: Diphtheria Toxoid protein; NY-ESO-1: Testis cancer antigen

P+I: PMA(Phorbol myristate acetate, 50ng/mL) + Ionomycin(1μg/mL); Fluzone: Influenza Virus Vaccine; MTB06R: Mycobacterium tuberculosis antigen 6KDa; MTB16R: Mycobacterium tuberculosis antigen 16KDa; TTOX15: Purified Tetanus Toxoid protein; DTOX15: Diphtheria Toxoid protein; NY-ESO-1: Testis cancer antigen

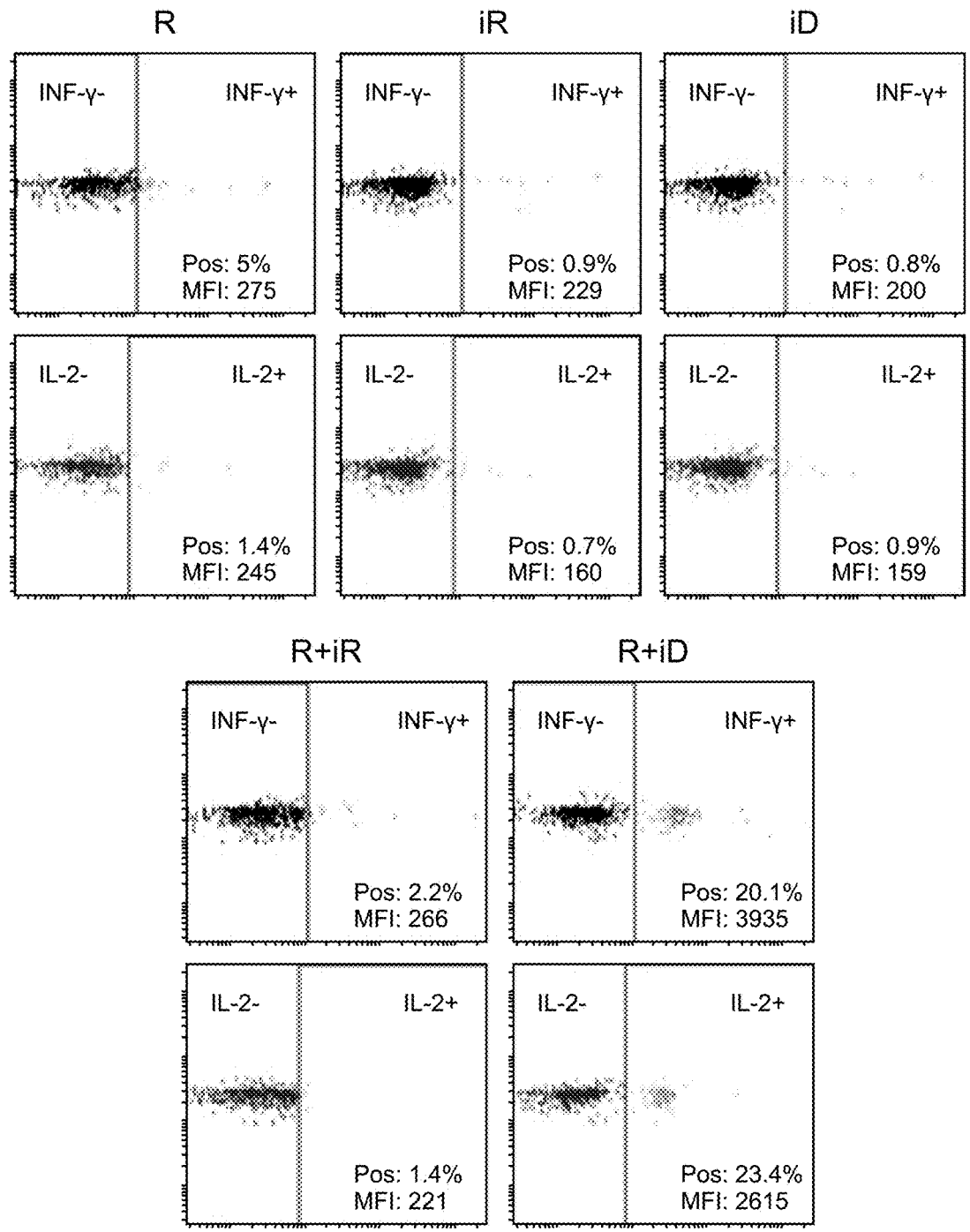

BIOMARKER DETECTION METHODS AND SYSTEMS AND KITS FOR PRACTICING SAME

CROSS-REFERENCE TO RELATED APPLICATIONS

Pursuant to 35 U.S.C. § 119 (e), this application claims priority to the filing date of the U.S. Provisional Patent Application Ser. No. 62/253,549, filed Nov. 10, 2015, the disclosure of which is herein incorporated by reference.

INTRODUCTION

The measurement of soluble and secreted cytokines and other analytes in serum and plasma is becoming increasingly important in the study and management of many diseases. Immune cells can be stimulated by various means to produce specific analytes. Secreted analytes can be quantitatively measured by ELISA or Cytometric Bead Array (CBA). The frequencies of cytokine-producing cells can be measured by Enzyme-Linked Immunospot (ELISPOT) or by flow cytometric analysis of intracellular cytokines.

The ELISPOT assay is a widely used method for monitoring cellular immune responses in humans and other animals, and has found clinical applications in the diagnosis of tuberculosis and the monitoring of graft tolerance or rejection in transplant patients. The ELISPOT technique has proven to be among the most useful means available for monitoring cell-mediated immunity, due to its ability to detect rare antigen-specific T cells (or B cells) and its ability to visualize single positive cells within a population of peripheral blood mononuclear cells (PBMCs). The ELISPOT assay allows visualization of individual activated or responding cells and identification of the secretory product(s) released. Each spot that develops in the assay theoretically represents a single reactive cell, although multiple cells on top of one another cannot be distinguished. Thus, the ELISPOT assay provides both qualitative (regarding the specific cytokine or other secreted immune molecule) and quantitative (the frequency of responding cells within the test population) information. ELISA-based assays have long been the standard for quantitative analysis of cytokines and other biomarkers, but are not well suited for high throughput multiplex analyses and suffer from poor sensitivity due to dilution by diffusion in the supernatant.

The introduction of flow cytometric bead-based technology has added a new approach for investigators to simultaneously measure multiple analytes in biological and environmental samples. In the context of measuring secreted factors, existing cytometric bead-based assays involve culturing cells that secrete the factor(s) of interest, separating the supernatant containing the factor(s) from the cells, combining the supernatant with beads adapted to bind to the factor(s) (e.g., via an antibody linked to the beads), and detecting the resulting complexes in a flow cytometer.

The Cytometric Bead Array (CBA) system from BD Biosciences (San Jose, Calif.) relies on different fluorescent intensities of a single fluorophore to accomplish multiplexing. The xMAP® technology (formerly LabMAP, FlowMetrix) by Luminex (Austin, Tex.) uses digital signal processing capable of classifying polystyrene beads (microspheres) dyed with distinct proportions of red and near-infrared fluorophores. These proportions define 'spectral addresses' for each bead population. Copalis® multiplex technology, produced by DiaSorin, is unique from most other multiplex bead array approaches in that it does not use fluorescence to discriminate different bead populations, but rather differentiates monomeric latex microspheres from latex aggregates and cells on the basis of their unique light scatter properties by flow cytometry. The system can measure two types of events: polystyrene-microparticle latex co-agglutination and polystyrene-gold colloid microparticle coupling. The former is useful for detecting the presence of antibodies to infectious agents or autoantigens, which are coated onto latex microparticles. Further details regarding bead-based assays may be found, e.g., in Elshal & McCoy (2006) *Methods* 38(4):317-323.

SUMMARY

Aspects of the present disclosure include methods that include co-culturing a cell and a microparticle that includes a capture ligand, in a culture medium under conditions in which a biomarker produced by the cell is bound (e.g., immediately bound) by the capture ligand. Such methods may further include detecting (e.g., by flow or mass cytometry) complexes that include the microparticle, the capture ligand, the biomarker, and a detection reagent. The methods may further include determining the proportion or number of cells among a heterogeneous cell population that produced the biomarker and/or the level of biomarker secreted by such cells. Compositions, systems and kits are also provided.

BRIEF DESCRIPTION OF THE FIGURES

FIG. 10 provides data showing the effects of immunotherapeutic agents on the secretion of the Th1 cytokine, IFN-γ, as determined using a method according to one embodiment of the present disclosure.

FIG. 11 provides data showing the effects of immunotherapeutic agents on the secretion of the Th1 cytokine, IL-2, as determined using a method according to one embodiment of the present disclosure.

FIG. 12 provides data showing the effects of immunotherapeutic agents on the secretion of the Th2 cytokine, IL-4, as determined using a method according to one embodiment of the present disclosure.

FIG. 13 provides data showing the effects of immunotherapeutic agents on the secretion of the Th2 cytokine, IL-5, as determined using a method according to one embodiment of the present disclosure.

FIG. 14 provides data showing the effects of immunotherapeutic agents on the secretion of the Th2 cytokine, IL-10, as determined using a method according to one embodiment of the present disclosure.

FIG. 30 provides flow cytometry data relating to the determination of recipient immunity to donor cells using a FlowSpot assay according to one embodiment of the present disclosure.

DETAILED DESCRIPTION

Figure 1:
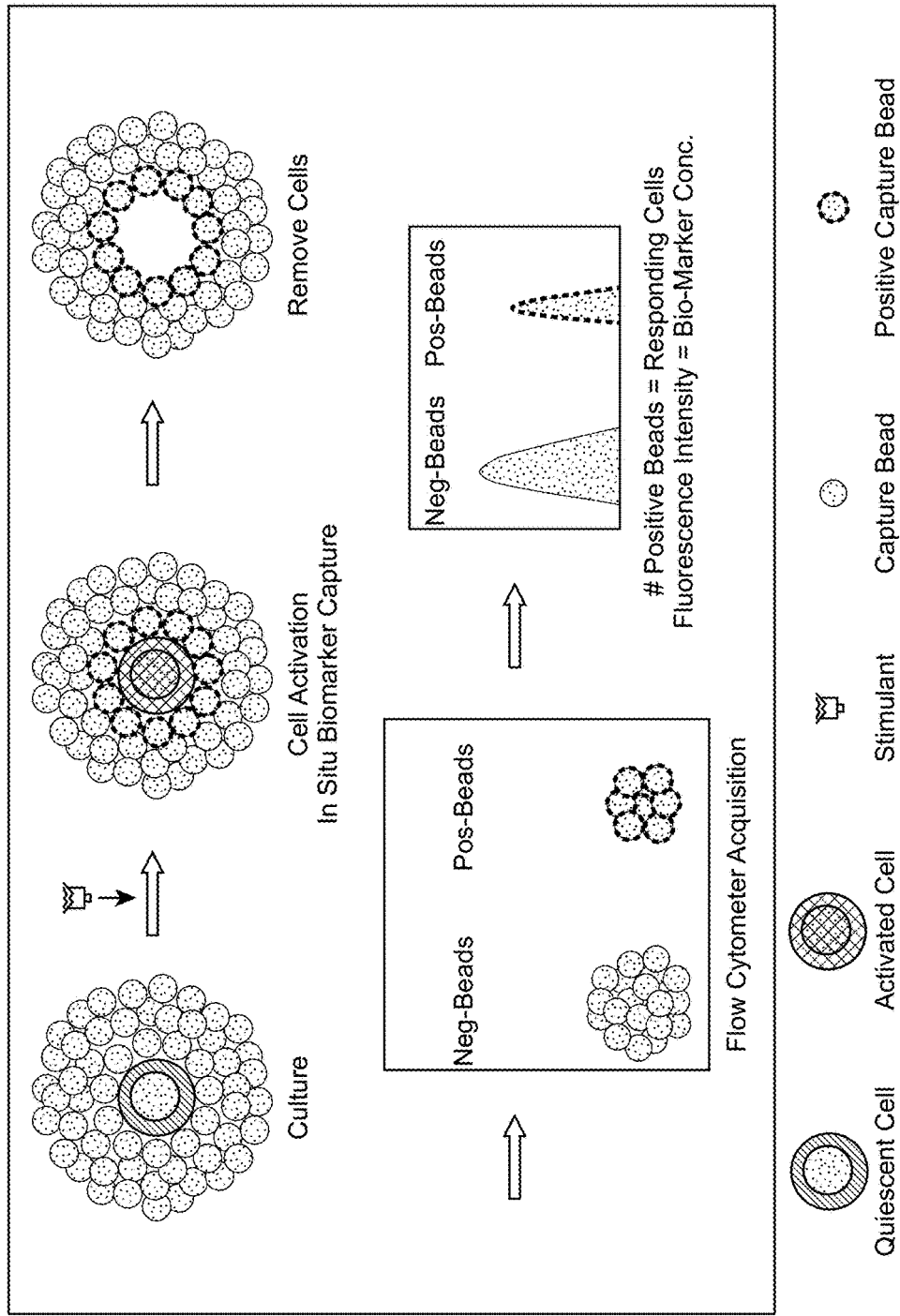
FIG. 1, panels A, B and C, schematically illustrate methods according to embodiments of the present disclosure.
Figure 1:
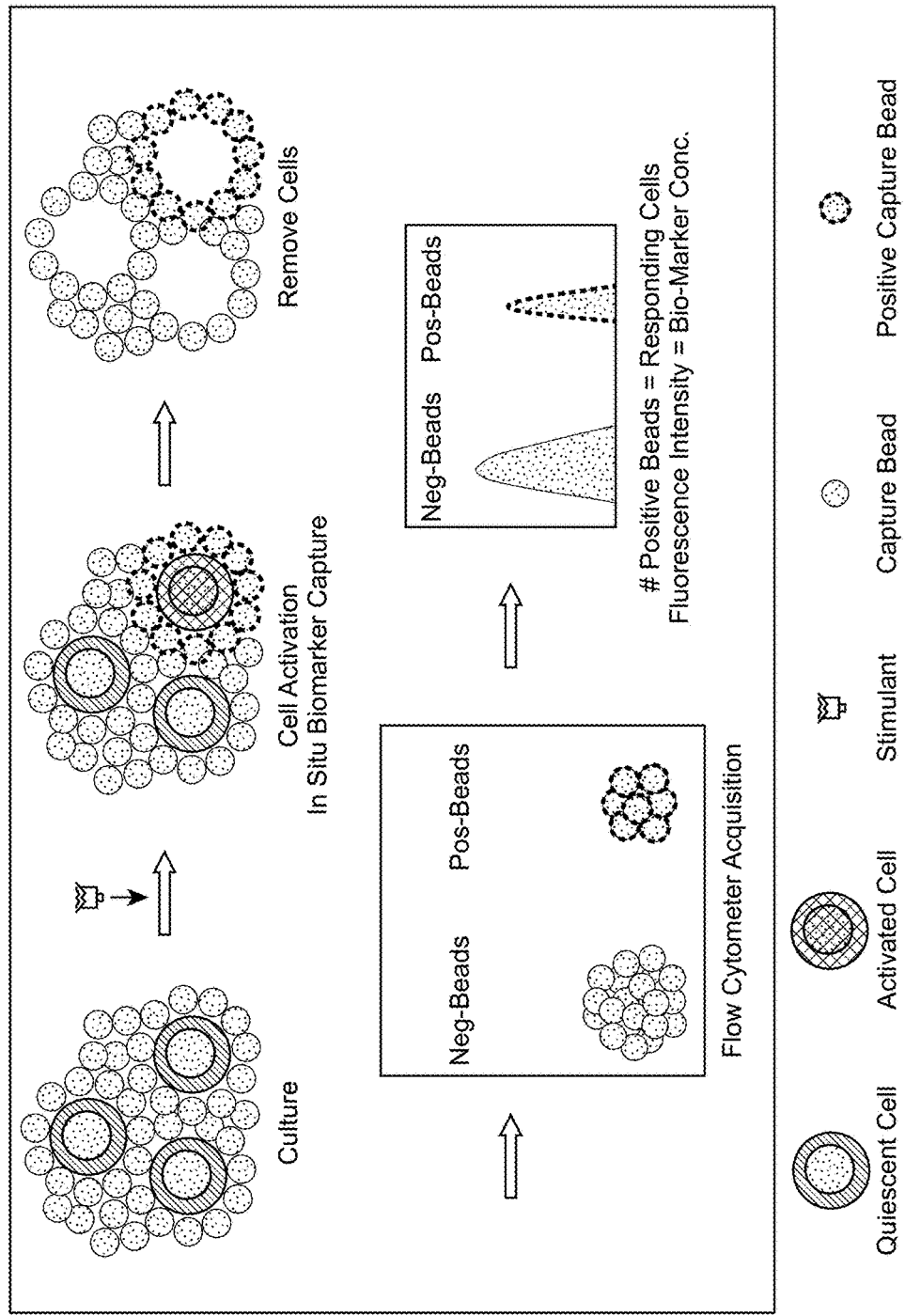
Figure 1:
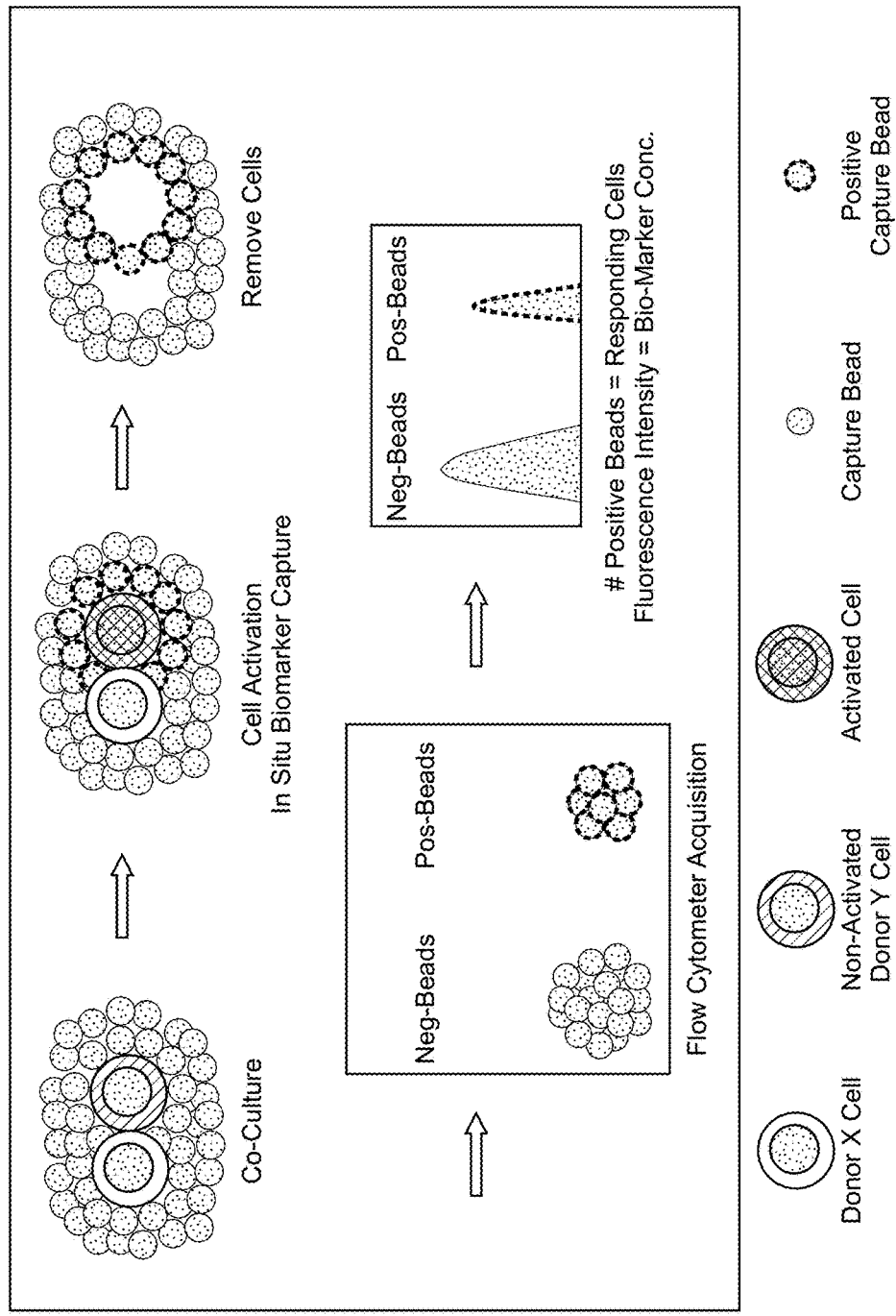

Provided are methods that include co-culturing a cell and a microparticle that includes a capture ligand, in a culture medium under conditions in which a biomarker produced by the cell is bound by the capture ligand. Such methods may further include detecting (e.g., by flow or mass cytometry) complexes that include the microparticle, the capture ligand, the biomarker, and a detection reagent. The methods may further include determining the proportion or number of cells among a purified or heterogeneous cell population that produced the biomarker and/or the level of biomarker secreted by such cells. Compositions, systems and kits are also provided.

Before the methods, compositions, systems and kits of the present disclosure are described in greater detail, it is to be understood that the methods, compositions, systems and kits are not limited to particular embodiments described, as such may, of course, vary. It is also to be understood that the terminology used herein is for the purpose of describing particular embodiments only, and is not intended to be limiting, since the scope of the methods, compositions, systems and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions, systems and kits. The upper and lower limits of these smaller ranges may independently be included in the smaller ranges and are also encompassed within the methods, compositions, systems and kits, subject to any specifically excluded limit in the stated range. Where the stated range includes one or both of the limits, ranges excluding either or both of those included limits are also included in the methods, compositions, systems and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions, systems and kits belong. Although any methods, compositions, systems and kits similar or equivalent to those described herein can also be used in the practice or testing of the methods, compositions, systems and kits, representative illustrative methods, compositions, systems and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions, systems and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions, systems and kits, which are, for clarity, described in the context of separate embodiments, may also be provided in combination in a single embodiment. Conversely, various features of the methods, compositions, systems and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions/kits. In addition, all sub-combinations listed in the embodiments describing such variables are also specifically embraced by the present methods, compositions, systems and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, compositions, systems and kits. Any recited method can be carried out in the order of events recited or in any other order that is logically possible.

Methods

Aspects of the present disclosure include methods that include co-culturing a cell and a microparticle that includes a capture ligand, in a culture medium under conditions in which a biomarker produced by the cell is bound by the capture ligand on the microparticle.

According to certain embodiments, the methods of the present disclosure include co-culturing in a culture medium: a heterogeneous cell population that includes a first subpopulation of cells and a second subpopulation of cells, and microparticles that include capture ligands that specifically bind to a biomarker of interest. Such methods may further include stimulating the first subpopulation of cells to secrete the biomarker, where upon secretion of the biomarker, the biomarker is bound by the capture ligands.

Embodiments of the above methods will now be described in detail.

As summarized above, the cells and microparticles are co-cultured in a culture medium under conditions in which a biomarker produced by the cell is bound by the capture ligand. By "co-culturing" is meant that the cells are cultured (e.g., grown/maintained under controlled conditions) in the presence of the microparticles.

The co-culture may be in suspension, where the cells and microparticles are not attached to a surface of a cell culture container during the co-culture. In other aspects, the co-culture may be an adherent co-culture, in which the cells are attached to a surface of a cell culture container. In this way, the cells and microparticles are spatially "fixed" relative to one another during the co-culture, with some microparticles being in the immediate vicinity of the cells and other microparticles being remote from the cells (and hence less accessible (or completely inaccessible) to any biomarkers secreted by the cells). In certain aspects, the cells are mixed with microparticles and seeded on the bottom of a culture container by centrifugation and/or free sedimentation.

Suitable conditions for culturing one or more cell types of interest are described in detail, e.g., in Aschner et al. *Cell Culture Techniques* (ISBN 978-1-61779-077-5); Mitry & Hughes *Human Cell Culture Protocols* (ISBN 978-1-61779-367-7); Freshney, R. I. *Culture of Animal Cells* (ISBN: 978-0-470-52812-9); Mather *Stem Cell Culture* (ISBN-13: 9780080878041); Coleman et al. *Plant Cell Culture* (ISBN: 9781859963203); and elsewhere. Optimal conditions may vary depending on the particular cell type(s) being cultured. Example conditions for certain cell types are described in the Experimental section below.

The co-culture conditions include co-culturing the cells and microparticles at a suitable temperature (such as from 30° C. to 45° C., e.g., 37° C.), and gas mixture (e.g., from 3% to 10% $CO_2$, e.g., 5% $CO_2$). The co-culture may occur in a suitable culture medium for the cell type being cultured. Culture media that find use in culturing cells are known and include, e.g., DMEM, RPMI, and the like.

The culture medium may be selected or modified to have a suitable pH. Most normal mammalian cell lines grow well at pH 7.4, and there is very little variability among different cell strains. However, some transformed cell lines have been shown to grow better at slightly more acidic environments (e.g., pH 7.0-7.4), and some normal fibroblast cell lines prefer slightly more basic environments (e.g., pH 7.4-7.7). Insect cell lines such as Sf9 and Sf21 grow optimally at pH 6.2.

The culture medium may be selected or modified to include additional components, such as glucose, growth factors, other nutrients, antibiotics, and/or any other components useful for growing/maintaining the cell type(s) of interest. The growth factors used to supplement media may be derived from the serum of animal blood, such as fetal bovine serum (FBS), bovine calf serum, equine serum, and porcine serum. Alternatively, serum-free medium may be used. Antibiotics useful for controlling or eliminating cell culture contamination include, but are not limited to, actinomycin D, kanamycin, ampicillin, neomycin, carbenicillin, penicillin streptomycin (Pen Strep), cefotaxime, polymyxin B, fosmidomycin, streptomycin, and gentamicin.

The co-culture occurs under conditions in which the biomarker produced by the cell is bound by the capture ligand. The co-culture conditions, therefore, include a temperature, pH, etc. such that the conditions are compatible with the binding of the capture ligand to the biomarker, which conditions may vary depending on the particular biomarker and the capture ligand employed when practicing the methods of the present disclosure. Such conditions may be the conditions under which the cell type(s) of interest would otherwise be cultured for standard growth/maintenance.

The ratio of cells to microparticles in the co-culture may vary. In certain aspects, the number of cells is greater than the number of microparticles, and the cell:microparticle ratio at the onset of the co-culture is from 1:1 to 1000:1, including 2:1 to 50:1, such as from 5:1 to 30:1, including 8:1 to 20:1, e.g., 10:1 to 17:1 (e.g., 14:1). According to certain embodiments, when the number of cells is greater than the number of microparticles, the ratio of cells to microparticles at the onset of the co-culture is 2:1 or greater, 3:1 or greater, 4:1 or greater, 5:1 or greater, 6:1 or greater, 7:1 or greater, 8:1 or greater, 9:1 or greater, 10:1 or greater, 11:1 or greater, 12:1 or greater, 13:1 or greater, 14:1 or greater, 15:1 or greater, 16:1 or greater, 17:1 or greater, 18:1 or greater, 19:1 or greater, or 20:1 or greater. In certain aspects, when the number of cells is greater than the number of microparticles, the ratio of cells to microparticles at the onset of the co-culture is 20:1 or less, 19:1 or less, 18:1 or less, 17:1 or less, 16:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, 3:1 or less, or 2:1 or less.

According to certain embodiments, the number of microparticles is greater than the number of cells in the co-culture. For example, the ratio of microparticles to cells at the onset of the co-culture may be from 2:1 to 2000:1, including 2:1 to 200:1, such as from 5:1 to 50:1, including 8:1 to 20:1, e.g., 10:1. In certain aspects, when the number of microparticles is greater than the number of cells, the ratio of microparticles to cells at the onset of the co-culture is 2:1 or greater, 3:1 or greater, 4:1 or greater, 5:1 or greater, 6:1 or greater, 7:1 or greater, 8:1 or greater, 9:1 or greater, 10:1 or greater, 11:1 or greater, 12:1 or greater, 13:1 or greater, 14:1 or greater, 15:1 or greater, 16:1 or greater, 17:1 or greater, 18:1 or greater, 19:1 or greater, 20:1 or greater, 50:1 or greater, or 200:1 or greater. According to certain embodiments, when the number of microparticles is greater than the number of cells, the ratio of microparticles to cells at the onset of the co-culture is 200:1 or less, 50:1 or less, 20:1 or less, 19:1 or less, 18:1 or less, 17:1 or less, 16:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, 3:1 or less, or 2:1 or less.

The cells to be co-cultured with the microparticles may be derived from a source of interest, such as a biological sample. In certain aspects, the cells are obtained from a biological fluid or biological tissue. Examples of biological fluids include blood, plasma, serum, saliva, urine, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries, buccal tissue (e.g., the cells may be obtained from a buccal swab), biopsy tissue, and individual cells.

In certain aspects, the cells to be co-cultured are obtained from a fluid, tissue, organ, and/or the like of a mammal (e.g., a human, a rodent (e.g., a mouse), or any other mammal of interest). In other aspects, the cells to be co-cultured are obtained from a source other than a mammal, such as bacteria, yeast, insects (e.g., *Drosophila*), amphibians (e.g., frogs (e.g., *Xenopus*)), plants, or any other non-mammalian cellular source. According to certain embodiments, viruses (rather than cells) are co-cultured with the microparticles.

The cells may be obtained from an individual (e.g., a human individual) of interest. According to certain embodiments, the individual is one in which it is desirable to predict and monitor vaccine efficacy before or after vaccination. As such, encompassed by the present disclosure are methods of predicting and monitoring vaccine efficacy before or after vaccination. In certain aspects, the individual is one in which it is desirable to evaluate a given specific immunity to a pathogenic organism including bacteria, viruses, fungi, and/or parasites for the purposes of treatment or diagnosing disease susceptibility. Accordingly, encompassed by the present disclosure are methods of determining a given specific immunity of an individual to a pathogenic organism including bacteria, viruses, fungi, and/or parasites, and optionally diagnosing and/or treating the individual accordingly. In certain aspects, the individual is one in which it is desirable to evaluate a given specific immunity to an allergen (e.g., peanuts, ragweed pollen, etc.) for purposes of treatment or diagnosing allergy susceptibility. As such, encompassed by the present disclosure are methods of determining a given specific immunity of an individual to an allergen, and optionally diagnosing and/or treating the individual accordingly. According to certain embodiments, the individual is an immunotherapy patient (e.g., a cancer patient, an auto-immune disease patient, etc.) where it is desirable to evaluate and monitor the potential/actual efficacy of immunotherapy (immunotherapeutic drugs) for the purposes of treatment or disease classification. As such, encompassed by the present disclosure are methods of determining/monitoring in an immunotherapy patient potential/actual efficacy of immunotherapy, and optionally diagnosing and/or treating the patient accordingly. In certain aspects, the individual is a transplant candidate or transplant recipient in which it is desirable to evaluate the given specific immunity or the compatibility between the potential/actual graft donor and recipient, assess risk for transplant rejection with a given donor, monitor graft rejection, and/or guide immunotherapy. Encompassed by the present disclosure, therefore, are methods of assessing risk for transplant rejection with a given donor, monitoring graft rejection, and/or guiding immunotherapy. According to certain embodiments, the individual is a tumor patient in which it is desirable to detect membrane-bound or secreted tumor markers for purposes of treatment or disease classification. As such, encompassed by the present disclosure are methods of treating a tumor patient and/or classifying a tumor of a patient, where the method includes detecting membrane-bound or secreted tumor markers according to the methods of the present disclosure. In certain aspects, the individual is a tumor patient in which it is desirable to monitor tumor metastasis by detecting circulating tumor cells (CTC) for the purposes of treatment or disease classification. Accordingly, aspects of the present disclosure include methods of treating a tumor patient, monitoring tumor metastasis, and/or classifying a tumor of a patient, where the method includes detecting circulating tumor cells (CTC) in the patient using the methods of the present disclosure.

In certain aspects, the cell co-cultured with the microparticles is selected from a peripheral blood mononuclear cell (PBMC), a white cell, a tumor cell, a stem cell, an immune cell, a lymphocyte, a T cell, a B cell, a natural killer (NK) cell, a natural killer T (NKT) cell, a macrophage, a dendritic cell, a monocyte, a granulocyte, an epithelial cell, an endothelial cell, and a platelet.

According to certain embodiments, the cells to be co-cultured are immune cells, such as lymphocytes (e.g., T cells, B cells (e.g., memory B cells), plasma cells, natural killer (NK) cells, and/or natural killer T (NKT) cells), macrophages, dendritic cells, monocytes, platelets, or any combination thereof.

T cells have a variety of roles and are classified by subsets. T cells are divided into two broad categories: CD8+ T cells or CD4+ T cells, based on which protein is present on the cell's surface. T cells carry out multiple functions, including killing infected cells and activating or recruiting other immune cells. CD8+ T cells also are called cytotoxic T cells or cytotoxic lymphocytes (CTLs). CTLs have specialized compartments, or granules, containing cytotoxins that cause apoptosis, i.e., programmed cell death. Because of its potency, the release of granules is tightly regulated by the immune system. The four major CD4+ T-cell subsets are TH1, TH2, TH17, and Treg, with "TH" referring to "T helper cell." TH1 cells interact with professional antigen presenting cells (the cells whose function it is to present antigen) and coordinate immune responses against pathogens. They produce and secrete molecules that alert, recruit, and activate other immune cells to respond (e.g., CD8+ T cells/CTL). TH2 cells interact with B cells and direct the immune response against extracellular pathogens toward antibody secretion. TH17 cells are important for recruiting neutrophils and are named for their ability to produce interleukin 17 (IL-17), a signaling molecule that activates immune and non-immune cells.

B cells function to present antigens to T cells, and to produce antibodies to neutralize infectious microbes, other foreign substances, cryptic antigens (e.g., DNA), or other antibodies. Antibodies are expressed in two ways. The B-cell receptor (BCR), which is present on the surface of a B cell, is a membrane bound antibody. B cells (and differentiated plasma cells) also secrete antibodies to diffuse and bind to pathogens and other foreign antigens. This dual expression is important because the initial problem, e.g., a bacterium, is recognized by a unique BCR and activates the B cell. The activated B cell responds by secreting antibodies, essentially the BCR but in soluble form.

In certain aspects, the cells to be co-cultured are obtained from a tumor. "Tumor", as used herein, refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, myeloma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like. In certain aspects, the cells to be co-cultured are circulating tumor cells (CTCs). In certain aspects, the cells to be co-cultured are obtained from a pre-cancerous tissue, such as the relevant tissue of an individual having a pre-cancerous condition, such as myelodysplastic syndrome (MDS) or the like.

As summarized above, the cells of interest are co-cultured with microparticles. By "microparticle" is meant a small particle (which is not a cell), having a greatest dimension ranging from 0.001 μm to 1000 μm, such as from 0.5 μm to 100 μm, e.g., 0.1 μm to 20 μm. In certain aspects, the microparticle has a greatest dimension of 20 μm or less, such as 15 μm or less, 10 μm or less, 5 μm or less, 1 μm or less, 0.75 μm or less, 0.5 μm or less, 0.4 μm or less, 0.3 μm or less, 0.2 μm or less, 0.1 μm or less, 0.01 μm or less, or 0.001 μm or less.

The microparticles may have any suitable shape, including but not limited to spherical, spheroid, rod-shaped, disk-shaped, pyramid-shaped, cube-shaped, cylinder-shaped, nanohelical-shaped, nanospring-shaped, nanoring-shaped, arrow-shaped, teardrop-shaped, tetrapod-shaped, prism-shaped, or any other suitable geometric or non-geometric shape.

The microparticles may be made of any suitable material, including but not limited to, latex, polystyrene, silica, a magnetic material, a paramagnetic material, or any combination thereof.

The microparticles include capture ligands present on (e.g., covalently attached to) the surface thereof. By "capture ligand" is meant a binding partner (e.g., a specific binding partner) for the biomarker, in which the capture ligand binds (or "captures") the biomarker upon contacting the biomarker under the co-culture conditions. Capture ligands that find use in practicing the methods of the present invention include, but are not limited to, an antibody (e.g., when the biomarker is an antigen or antibody to which the antibody specifically binds), an antigen (e.g., when the biomarker is an antibody that specifically binds the antigen), an enzyme (e.g., when the biomarker is a specific substrate of the enzyme), a substrate (e.g., when the biomarker is an enzyme that specifically acts upon the substrate), a protein, a peptide, a nucleic acid (e.g., when the biomarker is complementary nucleic acid), a drug, a chemical compound, and any combination thereof. For example, when the method involves detecting the secretion of a cytokine from the cells of interest, the capture ligand on the surface of the microparticles may be an antibody that specifically binds the cytokine. Also by way of example, when the method involves detecting the presence of proteins on the surface of a cell (e.g., B cell receptors (BCRs) on the surface of memory B cells) or membrane bound cytokines on the surface of a cell, the capture ligand on the surface of the microparticles may be a ligand to which the protein on the surface of the cell binds. For example, when the cells co-cultured with the microparticles are memory B cells, the capture ligand on the surface of the microparticles may be an antigen (e.g., an HLA antigen) to which the BCR specifically binds. In certain aspects, the capture ligand is a cluster of differentiation (CD) molecule, a tumor marker, a carbohydrate, a lipid, a peptide, a vitamin, a small chemical/molecule, or a binding partner (e.g., an antibody) that binds (e.g., specifically binds) to a cluster of differentiation (CD) molecule, a tumor marker, a carbohydrate, a lipid, a peptide, a vitamin, a small chemical/molecule, or the like.

The terms "specific binding," "specifically binds," and the like, refer to the preferential binding to a molecule relative to other molecules or moieties in a solution or reaction mixture. In some embodiments, the affinity between binding member and the target analyte to which it specifically binds when they are specifically bound to each other in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-19}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower $K_d$. As such, "binds specifically" or "specifically binds" is not meant to preclude a given binding member from binding to more than one analyte of interest. For example, antibodies that bind specifically to an analyte polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

As used herein, the term "antibodies" includes antibodies or immunoglobulins of any isotype, fragments of antibodies which retain specific binding to antigen, including, but not limited to, Fab, F(ab')$_2$, Fv, scFv, bi-specific-scFv, diabody, Fd, and Fc fragments, chimeric antibodies, humanized antibodies, fully human antibodies, single-chain antibodies, and fusion proteins including an antigen-binding portion of an antibody and a non-antibody protein.

The biomarker may be any biomarker of interest. For example, the biomarker may be a biomarker present within and secreted by the cells. Alternatively, the biomarker may be a biomarker expressed and/or present on (e.g., attached to) the surface of the cell. Biomarkers present on the surface of cells include, but are not limited to, cell surface receptors, such as an immunoglobulin in the case of B cell receptors present on the surface of memory B cells. In certain aspects, the biomarker captured by the capture ligand is a cytokine, an immunoglobulin (e.g., an antibody), a hormone, a growth factor, an enzyme, a protease, a protein, a heat shock protein, a glycoprotein, a peptide, a nucleic acid, a drug, a cluster differentiation (CD) molecule, a tumor marker, a receptor, a phosphorylated cell signaling protein, a complement component, a perforin, a nucleic acid, or any combination thereof. When the biomarker is a cytokine, the cytokine may be an interferon (e.g., IFN-γ, etc.), a chemokine, an interleukin (e.g., IL-2, IL-4, IL-5, IL-6, IL-10, IL-12, IL-17 etc.), a lymphokine, a tumor necrosis factor (e.g., TNF-α, etc.), transforming growth factor β (TGFβ), and the like, or any combination thereof. In certain aspects, the biomarker is a response element, such as perforin, granzyme B, or the like.

When the biomarker is secreted from the cells, the methods may include stimulating the cells to secrete the biomarker. In certain aspects, stimulating the cells to secrete the biomarker includes adding a stimulant to the culture medium. Various stimulants for stimulating the secretion of particular biomarkers from particular cell types of interest are known. In some embodiments, the stimulant is an antigen, a ligand, a protein, a lectin, a nucleic acid, a sub-cellular component, a microorganism (e.g., a bacteria, a virus, etc.) or component thereof (e.g., a bacterial or viral peptide), a chemical compound, an agonist, an antagonist, an enzyme, a drug, a vaccine, a CD (cluster differentiation) molecule, a receptor, and combinations thereof. The stimulant is provided in the culture medium at a concentration sufficient to stimulate the cells to secrete the biomarker. Specific examples of stimulants and conditions suitable for eliciting the secretion of biomarkers of interest from cells of interest are described in the Experimental section below.

According to certain embodiments, when the methods include stimulating the cell to secrete the biomarker, the cell and the microparticle are co-cultured in the presence of cells that are not stimulated to secrete the biomarker. For example, the cells in the co-culture may constitute a heterogeneous cell population that includes a first subpopulation of cells and a second subpopulation of cells, where only the first subpopulation of cells is of a type that secretes the biomarker upon being contacted by the stimulant.

In certain aspects, the methods include lysing the cells upon binding of the biomarker to the capture ligands. Any suitable approach for lysing the cells in the co-culture may be employed. According to certain embodiments, lysing the cells includes the addition of a lysis buffer (e.g., NP-40 lysis buffer) to the co-culture after the biomarker is bound to the capture ligands. Such a lysis step may be employed to facilitate certain downstream applications, such as detection of complexes that include the microparticle, capture ligand, biomarker and a detection reagent in a flow or mass cytometer.

According to certain embodiments, the methods include, after the biomarker is bound by the capture ligand, contacting the biomarker with a detection reagent to form a complex including the microparticle, the capture ligand, the biomarker, and the detection reagent. The detection reagent may be a binding partner (e.g., a specific binding partner) for the biomarker, which detection reagent is capable of binding to the biomarker when the biomarker is also bound by the capture ligand. According to certain embodiments, the detection reagent is an antibody (e.g., an antibody that specifically binds the biomarker), an antigen, a ligand, a protein, a receptor, a peptide, an enzyme, a substrate, a nucleic acid, a drug, a chemical compound, a carbohydrate, and combinations thereof.

In certain aspects, the detection reagent includes a detectable label. Detectable labels that find use in practicing the subject methods include, but are not limited to, fluorescent labels, metal elements (e.g., for use in a mass cytometry instrument), radiolabels, luminescent agents, and the like. For example, when it is desirable to detect the complex in a flow cytometer, a fluorescent label suitable/compatible with the particular flow cytometer may be employed. Detection reagents (e.g., antibodies, antigens, etc.) having such labels are available and include, but are not limited to, phycoerythrin (PE or R-PE), FITC, Cy-Chrome™ dye (BD Biosciences, San Jose, Calif.), peridinin chlorophyll protein (PerCP), allophycocyanin (APC), APC-Cy7, Alexa Fluor 488, Alexa Fluor 633, and the like.

Methods (generally referred to herein as "FlowSpot" assays) according to embodiments of the present disclosure are schematically illustrated in FIG. 1, panels A, B and C. Shown in panel A is a cell co-cultured with microparticles. In this example, a stimulant is added to the co-culture medium, which stimulant stimulates (e.g., activates) the cell to secrete a biomarker. The microparticles include a capture ligand that specifically binds to the biomarker. The microparticles adjacent (or in close proximity) to the responding stimulated cells are exposed to a higher concentration of the secreted biomarker, and therefore will capture more biomarker than microparticles more distant to the stimulated cells or to microparticles adjacent to non-responsive cells. In this example, the cell is lysed after stimulation. Following cell lysis, complexes that include the microparticle, capture ligand, and biomarker are contacted with a labeled detection reagent (e.g., a fluorescently-labeled antibody) that specifically binds the biomarker (e.g., if the capture ligand itself is not already labeled), forming complexes that include the microparticle, the capture ligand, the biomarker, and the labeled detection reagent. The microparticles are harvested and acquired on a flow or mass cytometer. The number of positive complexes ("events" or "spots") detected during flow or mass cytometric analysis may be counted.

Shown in panel B is a heterogeneous cell population that includes a first subpopulation of cells and a second subpopulation of cells, co-cultured with microparticles. A stimulant is added to the co-culture medium, which stimulant only stimulates (e.g., activates) cells of the first subpopulation of cells to secrete a biomarker. The microparticles include a capture ligand that specifically binds to the biomarker. The microparticles adjacent (or in close proximity) to the responding stimulated cells are exposed to a higher concentration of the secreted biomarker, and therefore will capture more biomarker than microparticles more distant to the stimulated cells or to microparticles adjacent to non-responsive cells. In this example, the cells are lysed after stimulation. Following cell lysis, complexes that include the microparticle, capture ligand, and biomarker are contacted with a labeled detection reagent (e.g., a fluorescently-labeled antibody) that specifically binds the biomarker (e.g., if the capture ligand itself is not already labeled), forming complexes that include the microparticle, the capture ligand, the biomarker, and the labeled detection reagent. The microparticles are harvested and acquired on a flow or mass cytometer. The number of positive microparticles ("events" or "spots") detected during flow or mass cytometric analysis may be counted, and the number of microparticles counted may be used to determine the number of cells that were stimulated in the co-culture and/or the proportion (e.g., percentage) of responding cells within the heterogeneous cell population. The signal intensity (e.g., Median Fluorescence Intensity; MFI) of positive microparticles may be used to determine concentration of the biomarker secreted from responding cells; or biomarker secreting capability of responding cells. Microparticles that were adjacent (or in close proximity) to the stimulated cells during the co-culture will have a higher detectable signal by virtue of the greater "load" of biomarker/labeled detection reagent on the surface thereof, as compared to microparticles that were more distant to the stimulated cells in the co-culture.

Shown in panel C is a heterogeneous cell population that includes a first donor cell and a second donor cell, co-cultured with microparticles. In this example, the first donor cell activates the second donor cell, which activation causes the second donor cell to secrete a biomarker. The microparticles include a capture ligand that specifically binds to the biomarker. The microparticles adjacent (or in close proximity) to the activated donor cell are exposed to a higher concentration of the secreted biomarker, and therefore will capture more biomarker than microparticles more distant to the activated cell or to microparticles adjacent to any non-activated cells in the co-culture. In this example, the cells are lysed after the co-culture. Following cell lysis, complexes that include the microparticle, capture ligand, and biomarker are contacted with a labeled detection reagent (e.g., a fluorescently-labeled antibody) that specifically binds the biomarker (e.g., if the capture ligand itself is not already labeled), forming complexes that include the microparticle, the capture ligand, the biomarker, and the labeled detection reagent. The microparticles are harvested and acquired on a flow or mass cytometer. The number of positive complexes ("events" or "spots") detected during flow or mass cytometric analysis may be counted.

In any embodiment in which flow or mass cytometric analysis is employed, the cytometric analysis may include—in addition to counting the number of positive complexes ("events" or "spots") detected—determining a signal intensity for each detected complex. Such signal intensity data may be used to determine the mean or median signal intensity of the detected complexes, which mean or median signal intensity may be used to determine a level of biomarker secretion (and, therefore, level of cell stimulation/activation) in the co-culture. Such information is not provided by existing bead-based approaches for detecting cell stimulation/activation, such as the existing cytometric bead array (CBA) approach.

Figure 2:
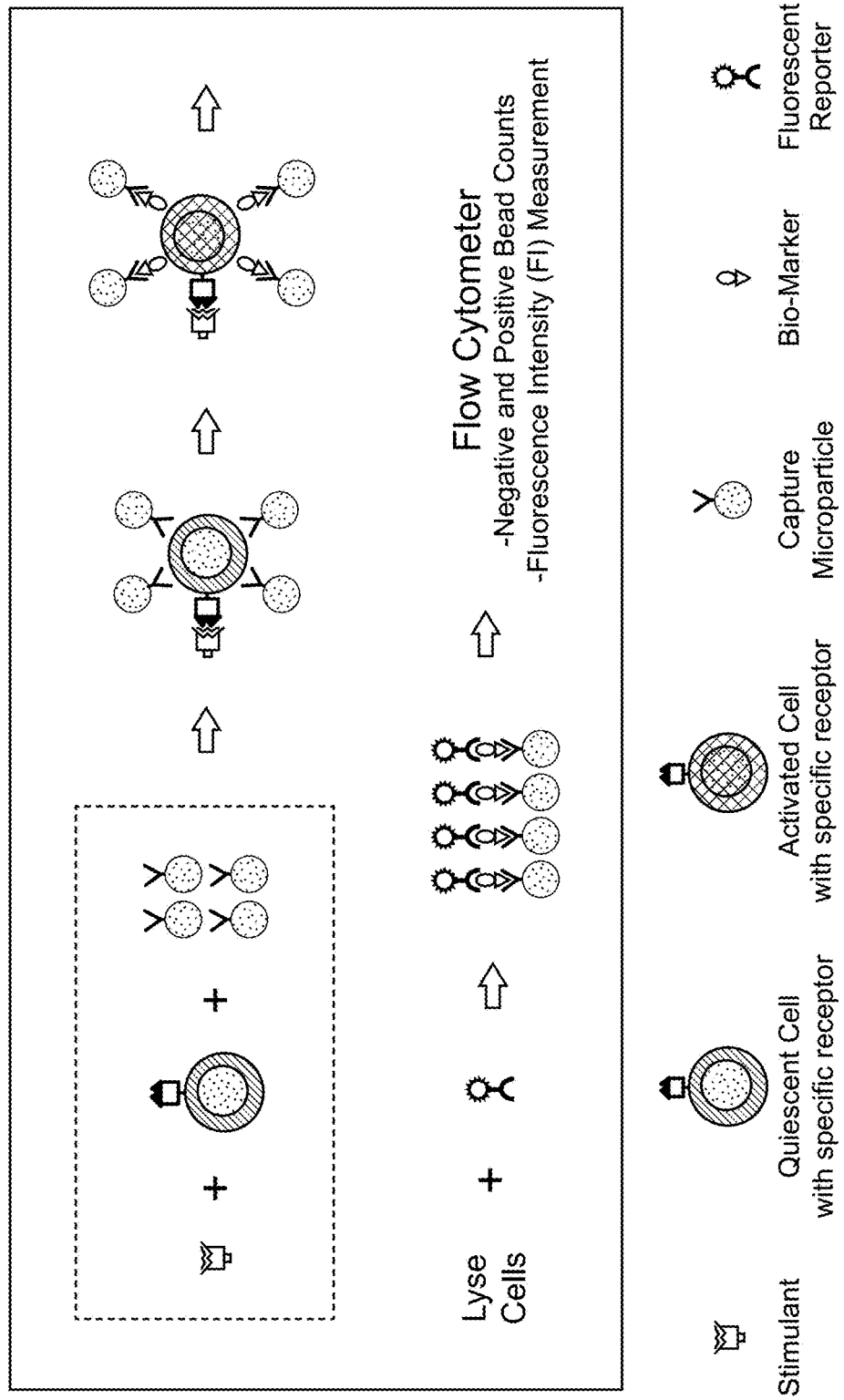
FIG. 2 schematically illustrates a method for detecting antigen-specific cellular responses according to one embodiment of the present disclosure.

A detection scheme according to one embodiment of the present disclosure is schematically illustrated in FIG. 2. In this example, antigen-specific cell responses are detected. A population of cells is co-cultured with microparticles, and cells (e.g., a subpopulation of cells among a heterogeneous cell population) are stimulated by addition of an antigen to the culture medium. The stimulated cells secrete a biomarker (e.g., a cytokine), which biomarker is captured by capture ligands present on the surface of the microparticles. The biomarker is then contacted with a labeled detection reagent (in this example, a fluorescent reporter), and the resulting complexes are acquired on a flow cytometer and detected, e.g., to determine the number and/or proportion of cells activated by the antigen in the co-culture based on the number of positive spots, and/or the level of activation based on the fluorescence intensity of the positive spots.

Figure 8:
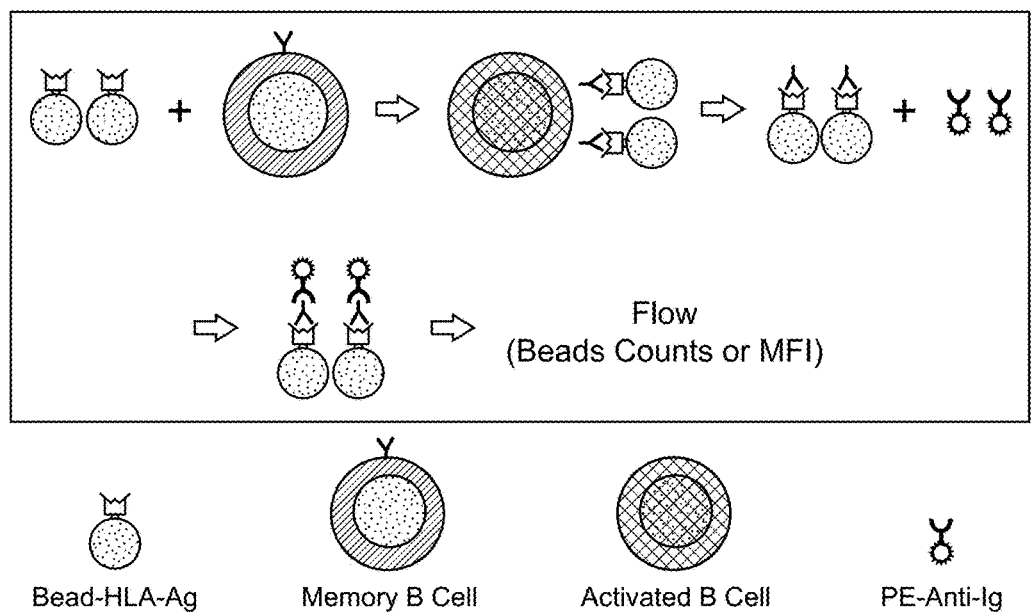
FIG. 8 schematically illustrates a method according to one embodiment of the present disclosure for antigen-specific memory B cell detection.

A further example FlowSpot method according to one embodiment of the present disclosure is schematically illustrated in FIG. 8. In this example, a sample containing memory B cells is co-cultured with microparticles and interrogated to determine whether the sample includes memory B cells having B cell receptors (BCRs) that specifically bind to an antigen of interest. During the culture, memory B cells can also differentiate to secrete antibodies (soluble BCR) that bind to the corresponding antigen-coated microparticles.

Here, the capture ligand present on the microparticles is the antigen of interest. Once the BCRs have had an opportunity to bind the antigen present on the microparticles, the cells are optionally lysed, and the BCRs are contacted with a detection reagent (in this example, a fluorescently-labeled anti-Ig antibody (PE-anti-Ig)). Any resulting microparticle-antigen-BCR-detection reagent complexes may then be acquired on a flow cytometer and counted. Any detected microparticle-antigen-BCR-detection reagent complexes indicate the presence of memory B cells in the co-culture having BCRs that specifically bind the antigen of interest. The number and/or proportion of such memory B cells among the starting heterogeneous population of memory B cells may be determined based on the number of complexes counted by the flow cytometer. Such an assay may be used to interrogate a cell population of interest for the presence (and optionally, the number and/or proportion) of cells having any cell surface receptor, where the ligand for the receptor is present on the microparticles, etc.).

Figure 23:
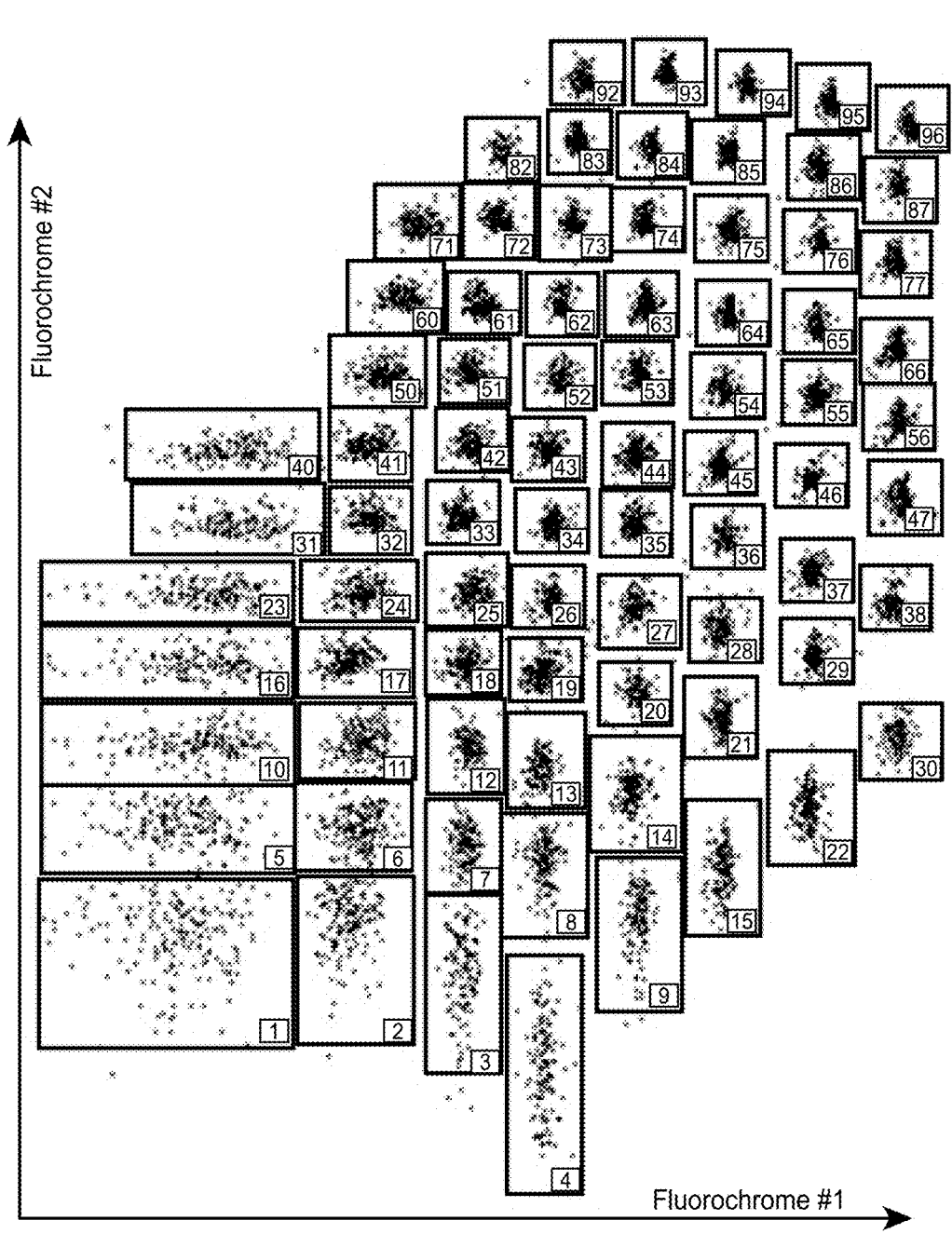
FIG. 23 illustrates the principle of a multiplex HLA antigen-specific memory B cell assay according to one embodiment of the present disclosure.
Figure 23:
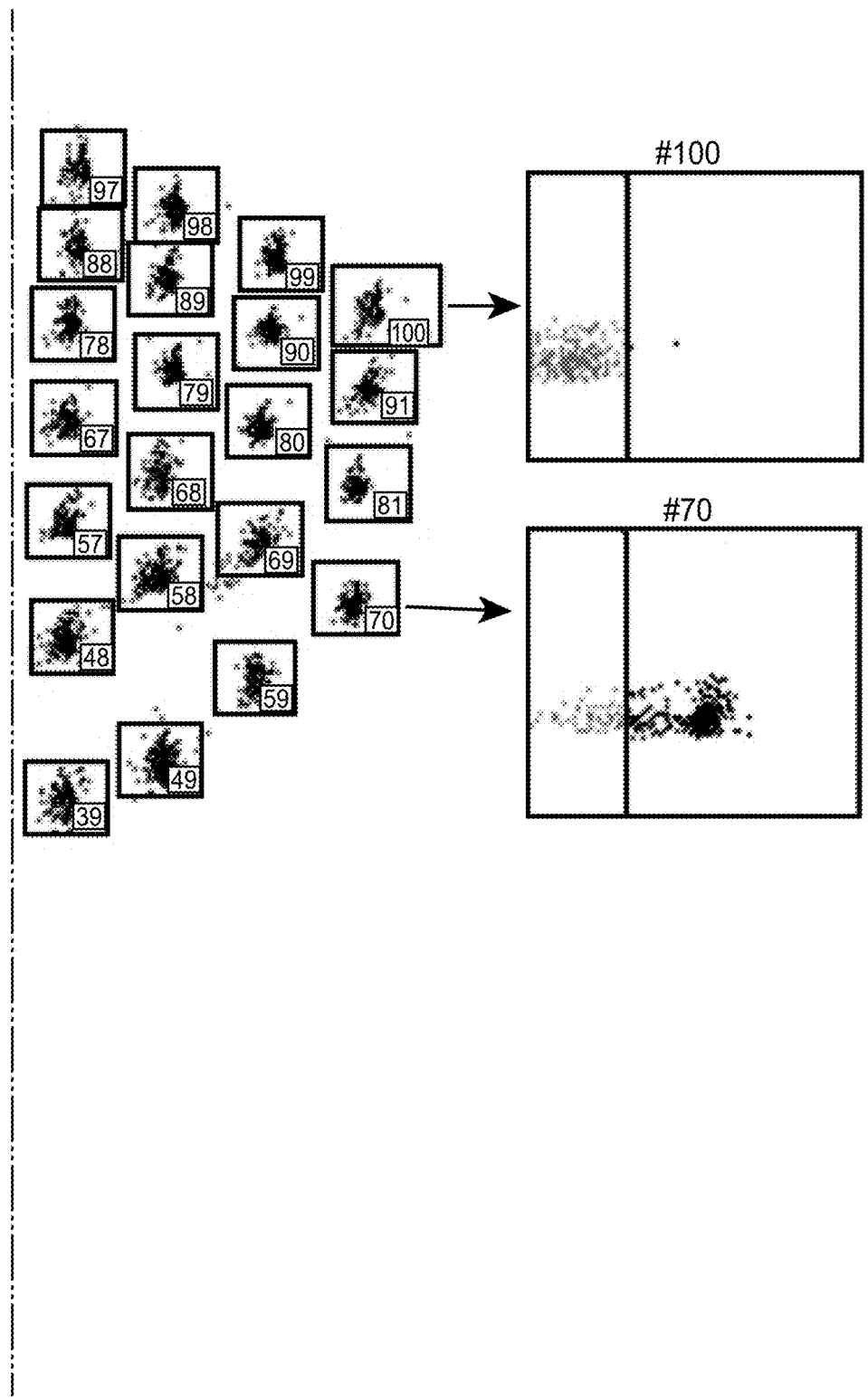
Figure 24:
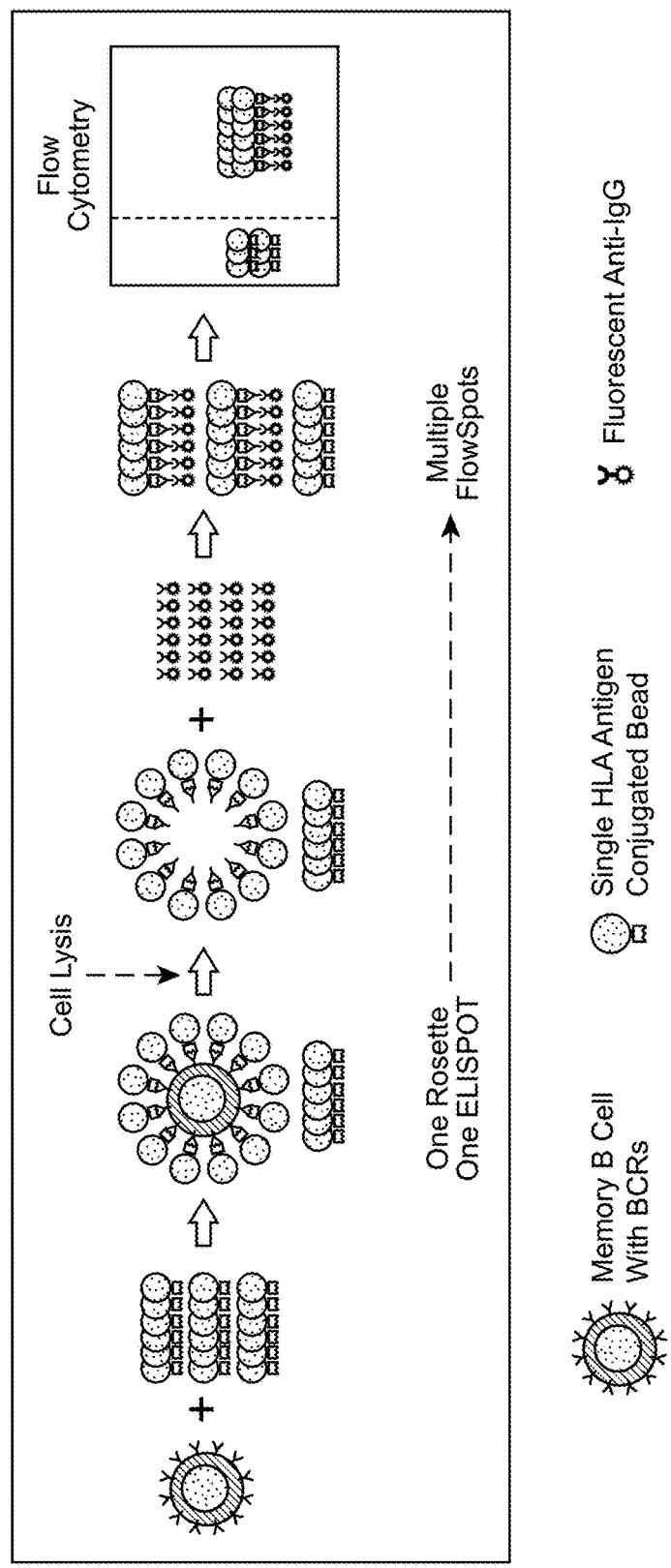
FIG. 24 illustrates the principle of a multiplex HLA antigen-specific memory B cell assay according to one embodiment of the present disclosure.

Also provided by the present invention are multiplexed methods useful for interrogating a cell population of interest for the presence (and optionally, the number and/or proportion) of multiple different cells that secrete, or present on their surface, various biomarkers of interest. One example of a multiplexed method according to an embodiment of the present disclosure is schematically illustrated in FIG. 23. This example involves a heterogeneous population of microparticles, where an intrinsic fluorescent property of each subpopulation of microparticle corresponds to a specific capture ligand (e.g., antigen, antibody, etc.) disposed on the surface thereof. The intrinsic fluorescent property may be based, e.g., on the proportion of a first fluorochrome and a second fluorochrome in the microparticle, as shown on the axes in FIG. 23. In this way, a heterogeneous cell population may be interrogated using a panel of capture ligands (e.g., a panel of antigens, such as HLA antigens) to detect cells in the heterogeneous cell population that secrete (or present on the surface thereof) a biomarker that binds to any one of the different capture ligands. FIG. 24 illustrates a FlowSpot assay according to one embodiment, while FIG. 23 illustrates how this approach may be multiplexed. As shown in FIG. 24, a sample containing memory B cells may be co-cultured with microparticles having a particular antigen of interest (here, an HLA antigen of interest) disposed on the surface thereof. BCRs that specifically bind to the HLA antigen are captured by the microparticles via the HLA antigen. The complexes may subsequently be detected and counted in a flow cytometer or a Luminex machine. Such an assay may be multiplexed by co-culturing a heterogeneous population of memory B cells with a heterogeneous population of microparticles that make up a panel of HLA antigens, as shown in FIG. 23.

Utility

The methods of the present disclosure (as well as the compositions, systems and kits described below) find use in a variety of applications, including, e.g., research applications, clinical applications (e.g., clinical diagnostic applications), etc.

According to certain embodiments, methods of the present disclosure find use in evaluating (optionally, quantitatively) specific cellular (including immune) response to virus, bacteria, allergens, allo-antigens, auto-antigens, tumors, and the like. In certain aspects, methods of the present disclosure find use in evaluating (optionally, quantitatively) the efficacy of vaccines, a therapy (e.g., immunotherapy), and the like. According to certain embodiments, methods of the present disclosure find use in the context of solid organ, bone marrow, and/or stem cell transplantation. For example, the methods enable detection, characterization, and/or quantitation of specific, potential or actual, anti-donor/graft immune responses for purposes of pre- and post-transplant monitoring.

The methods herein have a number of advantages over existing approaches. For example, the co-culture of cells with the microparticles provides direct cell to ligand contact, so that no dilution effect in solution occurs (e.g., dilution of secreted cytokine by diffusion in the medium). The number of specifically responding cells and the amount/concentration of the biomarker(s) can be quantitated by positively stained microparticles and fluorescence intensity, respectively. The methods do not suffer from steric hindrance due to size or inability to distinguish individual cells (e.g., cells on top of cells) because the capture ligand is present on the much smaller microparticle which flows through the cytometer as a single event, one after the other. The need for dedicated (e.g., limited use) and specialized equipment (e.g., an ELISPOT reader) or the need to send samples to reference labs (e.g., for ELISPOT analysis) is eliminated because flow cytometers are standard equipment and routinely used for enumerating cells/particles with specific characteristics. Another advantage of the methods of the present disclosure is that radioactivity is not required.

Compositions

Aspects of the present disclosure further include compositions. The compositions of the present disclosure find a variety of uses, including in some aspects, practicing the methods of the present disclosure. As such, provided are compositions that include any of the cells, microparticles, reagents, etc. described above in relation to the subject methods, in any desired combination.

According to certain embodiments, provided is a composition that includes a culture medium, a population of cells (at least a subpopulation of which expresses or is capable of expressing a biomarker), a cell lysis buffer, and microparticles including a capture ligand that specifically binds the biomarker.

The population of cells may be any cell population of interest, including but not limited to immune cells, lymphocytes, T cells, B cells, natural killer (NK) cells, natural killer T (NKT) cells, macrophages, dendritic cells, monocytes, and platelets.

In certain aspects, the biomarker is a cytokine, an immunoglobulin, a hormone, a growth factor, an enzyme, a protease, a protein, a glycoprotein, a peptide, a CD (cluster differentiation) molecule, a receptor, a nucleic acid, or any combination thereof. When the biomarker is a cytokine, the cytokine may be an interferon, a chemokine, an interleukin, a lymphokine, a tumor necrosis factor, or any combination thereof.

According to certain embodiments, the compositions further include a stimulant that stimulates at least a subpopulation of cells to secrete the biomarker. Stimulants that may be present in the subject compositions include, but are not limited to, an antigen, a ligand, a protein, an allergen, a peptide, a lectin, a nucleic acid, a DNA, a RNA, a cell, a sub-cellular component, a microorganism, a drug, a chemical compound, an agonist, an antagonist, and any combination thereof.

Any of the compositions of the present disclosure may be present in a container (e.g., a tissue culture container). Suitable containers include, but are not limited to, tubes, vials, tissue culture plates (e.g., a 96- or other-well tissue culture plates, etc.), petri dishes, etc.

Any of the compositions of the present disclosure may be present in a device, e.g., an incubator suitable for co-culturing cells and microparticles.

Systems

Also provided by the present disclosure are systems. According to certain embodiments, the systems find use in practicing one or more steps of the methods of the present disclosure.

In certain aspects, the system (e.g., a flow cytometry system) is adapted to count a number of positive microparticle complexes, where the positive microparticle complexes include a microparticle, a capture ligand, a biomarker, and a fluorescently-labeled detection reagent. The flow cytometry system is further adapted to determine the total number of microparticle complexes acquired by the system, calculate the percentage of positive microparticle complexes among the total number of microparticle complexes, and determine the number and/or proportion of cells in a cell-microparticle co-culture that included the biomarker. In certain aspects, the system is further adapted to determine a mean or median fluorescence intensity of the positive microparticle complexes acquired by the system, and determine a level of the biomarker present in the cell-microparticle co-culture.

By "adapted to" is meant that the system includes the components and functionality to perform the recited determinations, calculations, etc. For example, in certain aspects, the system includes a processor and a computer-readable medium (e.g., a non-transitory computer-readable medium). The computer-readable medium includes instructions executable by the processor to, e.g., count a number of positive microparticle complexes, determine the total number of microparticle complexes acquired by the system, calculate the percentage of positive microparticle complexes among the total number of microparticle complexes, and determine the number and/or proportion of cells in a cell-microparticle co-culture that included the biomarker. The computer-readable medium may further include instructions executable by the processor to determine a mean or median fluorescence intensity of the positive microparticle complexes acquired by the system, and determine a level of the biomarker present in the cell-microparticle co-culture.

The computer-readable medium (or processor-readable medium) is non-transitory in the sense that it does not include transitory propagating signals per se (e.g., a propagating electromagnetic wave carrying information on a transmission medium such as space or a cable). The media and instructions may be those designed and constructed for the specific purpose or purposes. Examples of non-transitory computer-readable media include, but are not limited to: magnetic storage media such as hard disks, portable flash drives, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Kits

As summarized above, the present disclosure provides kits. The kits may include one or more of any of the components/reagents described above in the section describing the methods of the present disclosure.

According to certain embodiments, the kits include microparticles that include a capture ligand that specifically binds a biomarker of interest, and a stimulant capable of stimulating a cell type of interest to secrete the biomarker. The kits may include any additional useful components and/or reagents, such as a detection reagent that specifically binds the biomarker. Such a detection reagent may be, e.g., an antibody, a ligand, a receptor, or a nucleic acid, and may include a detectable label (e.g., a fluorescent label, a radiolabel, a luminescent agent, or the like). The kit may include a cell lysis buffer to be used for removing cells after co-culturing the microparticles with cells.

Components of the kits of the present disclosure may be present in separate containers, or multiple components may be present in a single container. For example, the microparticles may be provided in a container separate from a container in which the stimulant is provided. The components may be provided in any suitable container(s), such as a tube (e.g., vial), in one or more wells of a plate (e.g., a 96-well plate, a 384-well plate, etc.), or the like.

In addition to the above-mentioned components, a kit of the present disclosure may further include instructions for using the components of the kit, e.g., to practice the methods of the present disclosure. For example, the kit may include instructions for co-culturing the microparticles and the cells of interest, instructions for stimulating the cell type of interest and detecting a complex that includes the microparticle, the capture ligand, the biomarker, and the detection reagent, and/or instructions for detecting the complex by flow cytometry. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Materials and Methods
ELISPOT Procedure

Each well was pre-wet with 15 µL of 35% ethanol (v/v in $ddH_2O$) for one min, and then rinsed with 150 µL sterile phosphate buffered saline (PBS) three times before the ethanol evaporated. MultiScreen IP plates (Millipore, Cat No. S2EM004M99) were coated with 100 µL (5 µg/mL final concentration) anti-IFN-gamma capture antibody in Coating Buffer ((1×PBS): 8 g NaCl; 0.2 g KCl; 1.44 g $Na_2HPO_4.7H_2O$, 0.24 g $KH_2PO_4$, dissolved in $H_2O$ to a final volume of 1 L. pH 7.2, sterile-filtered (0.2 µm-sized pore filter) and stored at 4° C.). Plates were incubated overnight at 4° C.

Coating Antibody was discarded, and wells washed 1× with 200 µL/well Blocking Solution (complete tissue culture medium (e.g. RPMI 1640 containing 10% Fetal Bovine Serum (FBS) and 1% Penicillin-Streptomycin-L-Glutamine)). 200 µL/well Blocking Solution was added and wells were incubated for 2 h at room temperature.

Blocking Solution was discarded. Mitogen or antigen was prepared, diluted in complete tissue culture medium (e.g., RPMI 1640 with FBS, Pen/Strep, and L-glutamine), and 100 µL/well was added to ELISPOT plate.

Cell suspensions were prepared at different densities, (e.g., $1\times10^5$-$2\times10^6$ cells/mL). 100 µL/well of each cell suspension was added to ELISPOT plate wells (the cell concentration used was $1\times10^5$/mL). ELISPOT plate lid was replaced, and ELISPOT plate was incubated at 37° C., 5% $CO_2$ and 99% humidity. The duration of the incubation time can be varied (e.g., 2 h-24 h) depending on the nature of the stimulatory cell culture system (incubation time presently used was 16 h).

Cell suspension was aspirated, and wells were washed 2× with deionized (DI) water. Wells were allowed to soak for 3-5 min at each wash step. Wells were washed 3× with 200 µL/well Wash Buffer I (1×PBS containing 0.05% nonionic detergent TWEEN®20 (0.5 mL TWEEN®20 per 1 L PBS), and Wash Buffer was discarded. Human IFNγ Detection Antibody (#Cat. 51-1890KZ, BD Biosciences; 2 µg/mL final concentration) was diluted in Dilution Buffer (1×PBS containing 10% FBS), and 100 µL was added per well. Lid was replaced and wells were incubated for 2 h at room temperature.

Detection Antibody solution was discarded and wells were washed 3× with 200 µL/well Wash Buffer I. Streptavidin-Horseradish Peroxidase (BD™ ELISPOT Streptavidin-HRP, Cat. No. 557630) was diluted in Dilution Buffer (1:100), and 100 µL/well diluted Streptavidin-HRP was added. Lid was replaced and wells incubated for 1 h at room temperature.

Streptavidin-HRP solution was discarded, and wells were washed 4× with 200 µL/well Wash Buffer I. Wells were washed 2× with 200 µL/well Wash Buffer II (1×PBS). 100 µL of Final Substrate Solution (BD™ ELISPOT AEC Substrate Set Cat. No. 551951) was added to each well. Spot development was monitored from 5-60 min.

No more than 15 min prior to use, one drop (20 µL) of AEC Chromogen was mixed with each 1 mL of AEC Substrate. Any remaining prepared AEC Substrate was discarded after use. Substrate reaction was stopped by washing wells with DI water. Plate was air-dried for 2 h—overnight at room temperature in the dark, until the plate was completely dry. Plates were stored in the dark prior to analysis. Spots were enumerated automatically using an ELISPOT Analyzer.

FlowSpot Procedure Example $1 \times 10^7$-$1 \times 10^8$ carboxyl microspheres (Spherotech, CP-35) were transferred to a microcentrifuge tube. Microspheres were pelleted by centrifugation at 20,000×g for 5 min. Supernatant was removed and microspheres were resuspended in 100 µL dH$_2$O by vortex and sonication for 30 seconds. Microspheres were pelleted by centrifugation at 20,000×g for 5 min. Supernatant was removed and the microspheres were resuspended in 200 µL 100 mM Monobasic Sodium Phosphate, pH 6.2 by vortex. 10 µL of 50 mg/mL Sulfo-NHS (Thermo Scientific, Cat No. 24520) diluted in dH$_2$O was added to the microspheres and mixed gently by vortex. 10 µL of 50 mg/mL EDC (Thermo Scientific, Cat No. 22980) diluted in dH$_2$O was added to the microspheres and mixed gently by vortex. Microspheres were incubated for 20 min at room temperature with gentle mixing by vortex at 10 min intervals. Activated microspheres were pelleted by centrifugation at 20,000×g for 5 min. Supernatant was removed and the microspheres were resuspended in 250 µL of 50 mM MES, pH 5.0 (Sigma, Cat No. M2933), by vortex and sonication for approximately 30 seconds. Microspheres were pelleted by centrifugation at 20,000×g for 5 min. Previous wash was repeated (for a total of two washes with 50 mM MES, pH 5.0). Supernatant was removed and the activated and washed microspheres were resuspended in 200 µL of 50 mM MES, pH 5.0 by vortex and sonication for approximately 30 seconds.

10-400 µg of the specific capture antibodies (e.g. monoclonal antibodies against interferon gamma (INFγ), interleukin-2 (IL-2), IL-4, IL-5, IL-10, Granzyme B (GrB), etc.) was added to the microspheres and total volume was brought up to 500 µl with 50 mM MES, pH 5.0. Coupling reaction was mixed by vortex and incubated at room temperature for 2 h with constant vortexing on a vortexer. Coupled microspheres were pelleted by centrifugation at 20,000×g for 5 min. Supernatant was removed and pelleted microspheres were resuspended in 500 µL of PBS-TBN (PBS, 0.1% BSA, 0.02% Tween-20, 0.05% Azide, pH 7.4) by vortex and sonication for approximately 30 seconds. This was followed by 30 min incubation with constant vortexing at room temperature. Coupled microspheres were pelleted by centrifugation at 20,000×g for 5 min. Supernatant was removed, and the microspheres were resuspended in 1 mL of PBS-TBN by vortex and sonication for approximately 30 seconds. Microspheres were pelleted by centrifugation at 20,000×g for 5 min. Previous wash was repeated (for a total of two washes with 1 mL PBS-TBN). Supernatant was removed, and the capture antibody conjugated microspheres were resuspended in 250-1000 µL of PBS-TBN. About 1000-10,000 capture microspheres were used for each 0.1× 10$^6$ cells.

One hundred thousand peripheral blood mononuclear cells (0.1×10$^6$ PBMC) or purified lymphocytes were mixed with 7,000 capture microspheres and distributed into each assay well of a 96-well U bottom plate. The plate was centrifuged at 1,500×g for 5 min and the supernatant was removed. The pellet of cells and capture beads were resuspended in 200 µL culture medium with or without testing reagent(s) or stimulus(i), then the plate was incubated in a humidified 37° C., 5% CO$_2$ incubator for 10 min to 7 days (usually 2 to 16 h). After incubation, the cells were lysed in NP-40 lysis buffer (10 mM Tris-HCl, pH 7.4, 10 mM NaCl, 3 mM MgCl$_2$, 0.5% NP-40). The capture beads were washed twice with 3% HBSA (3% BSA in HBSS) and incubated with 50 µL PE-labeled anti-Bio-marker for 60 min at room temperature. After two washes of 3% HBSA, the beads were acquired and analyzed on a BD FACSCanto II flow cytometer. The number of positive spots was calculated based on the following formulas:

Percent positive spots (%)=Number of positive particles acquired/Total number of particles acquired×100

Total number of positive spots=Percent positive spots (%)×7,000 (where 7,000=total number of particles/test)

Control wells used were as follows:
a. Negative control-1: beads+media only (no cells)
b. Negative control-2: beads+cells+media; without primary antibody
c. Negative control-3: beads+cells+media; control antigen (non-activator)
d. Positive control: cells+media+polyclonal T or B cell activators (e.g., PHA, PMA)

Example 1: Detection of Phytohaemagglutinin (PHA) Induced Interferon Gamma (IFNγ) Spots by ELISPOT and FlowSpot

ELISPOT

Figure 3:
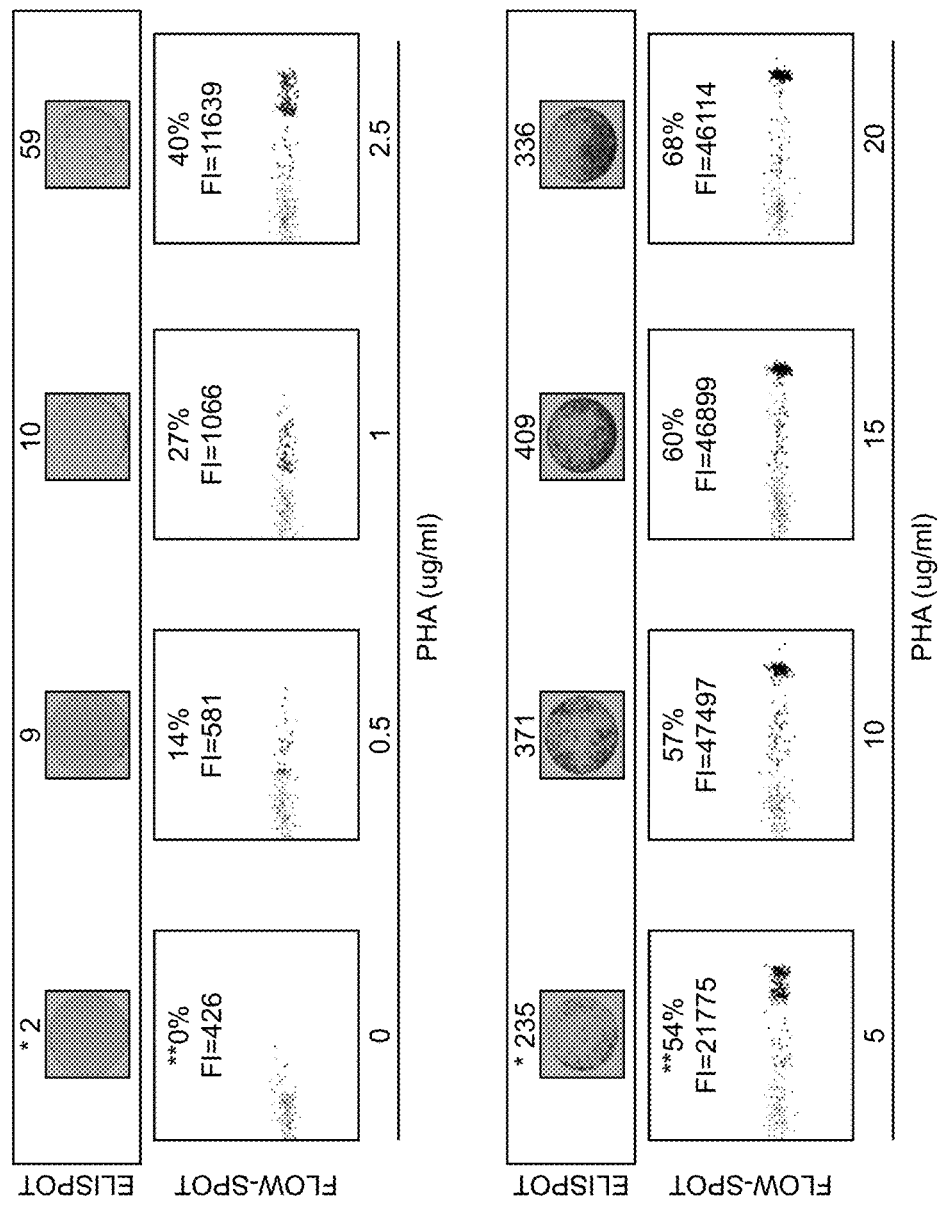
FIG. 3 shows the detection of phytohaemagglutinin (PHA)-induced interferon gamma (IFNγ) spots by ELISPOT and a FlowSpot assay according to one embodiment of the present disclosure.
Figure 4:
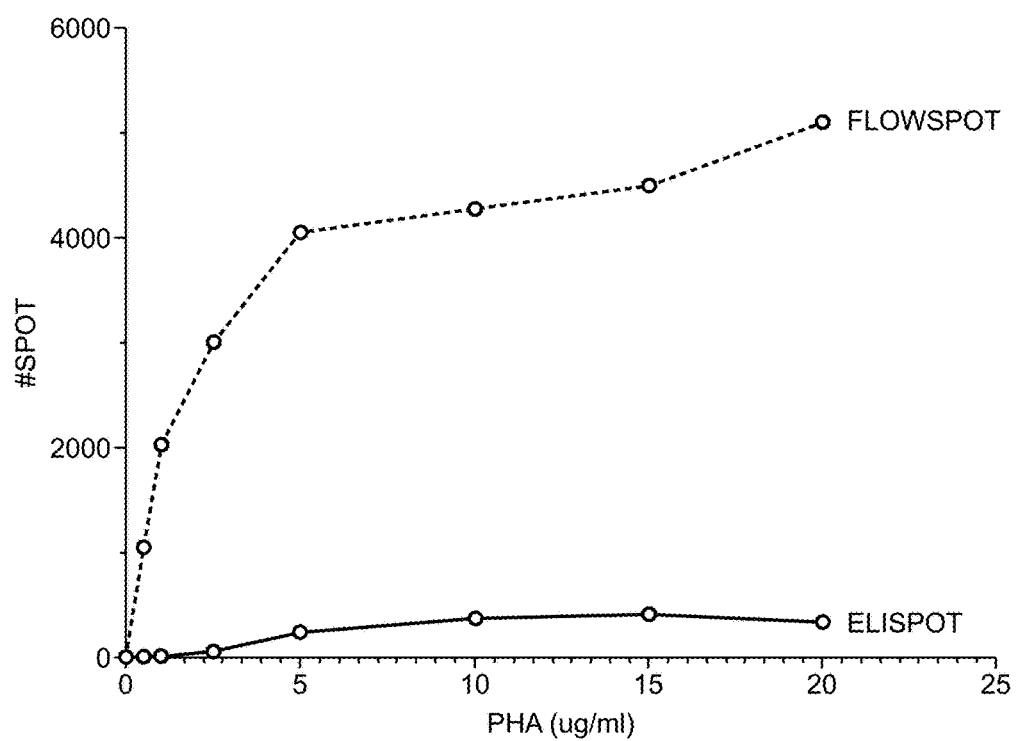
FIG. 4 shows the number of spots counted at various concentrations of PHA by ELISPOT and a FlowSpot assay according to one embodiment of the present disclosure.

One hundred thousand PBMC cells from C.T.L. (Cat# CTL-QC1, Shaker Heights, Ohio) were plated into a filter plate well pre-coated with IFNγ capture antibody and cultured for 16 h in the presence of PHA at various concentrations. The positive IFNγ spots were enumerated using a C.T.L. ImmunoSpot® Analyzer (FIG. 3 and FIG. 4).

FLOWSPOT

One hundred thousand of the same PBMC cells used in ELISPOT procedure were co-cultured with 7,000 IFNγ capture microparticles for 16 h in the presence of PHA at various concentrations. The spots and fluorescence intensity (FI) of FLOWSPOT were counted and measured by a FACSCanto II flow cytometer (BD Biosciences). Total number of positive IFNγ spots were calculated based on the previously described formulas. The FLOWSPOT was observed to be at least twenty times more sensitive than ELISPOT and able to detect very weak IFNγ responses induced by PHA (FIG. 3 and FIG. 4).

Example 2: Peptide Specific IFNγ Spots Detection by FLOWSPOT

Figure 5:
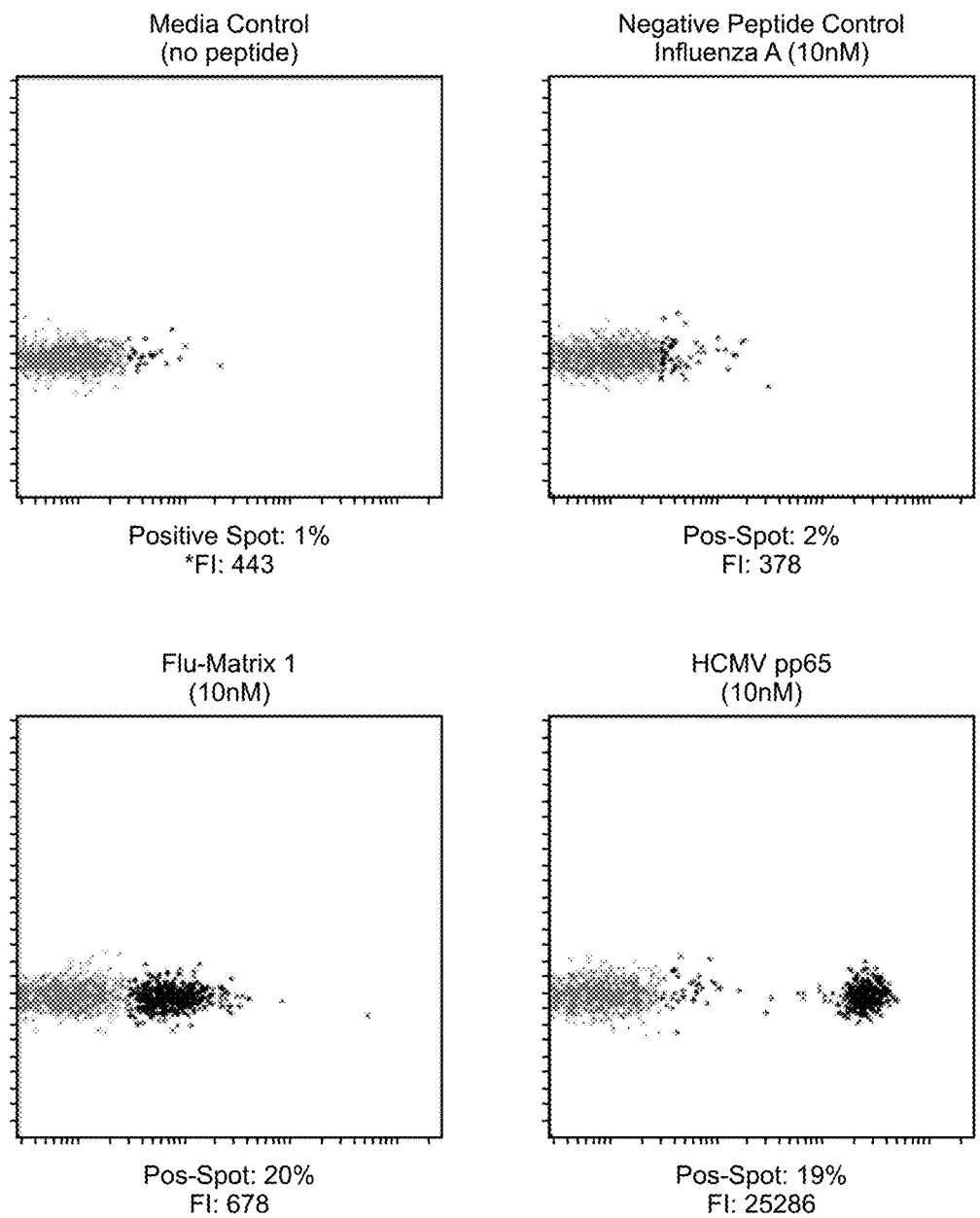
FIG. 5 shows flow cytometric data relating to viral peptide-specific T cell detection according to one embodiment of the present disclosure.

One hundred thousand HLA-typed antigen specific T cells from C.T.L. (Cat# CTL-QC1, Shaker Heights, Ohio) were co-cultured with 7,000 IFNγ capture microparticles for 16 h in the presence of the different peptides (10 nM) specified in FIG. 5. The IFNγ secretion induced by three peptides (#Cat. CTL-QC1; C.T.L.) were previously tested against the paired PMBCs (C.T.L. cells) by ELISPOT assay in C.T.L. and showed that HCMV pp65, Flu-Matrix, and influenza A were able to elicit strong, medium, and negative IFNγ responses on the PBMCs respectively. The same response pattern was also observed using FLOWSPOT but yielded a two-parameter result collected simultaneously in the same reaction well, i.e., the percentage of positive responding cells (% positive spots) and the relative IFNγ concentration (FI). As shown in FIG. 5, HCMV pp65 induced 19% IFNγ positive spots (1,330 spots) with a high FI (FI=25,286) and Flu-Matrix induced 20% positive spots (1,400 spots) with a weak FI (FI=678) compared to the negative response induced by influenza A (2% positive spots=140 spots; FI=378) and the media control (1% positive spots=70 spots; FI=443).

Example 3: Two-Color IFNγ/IL-2 Detection by FLOWSPOT

Figure 6:
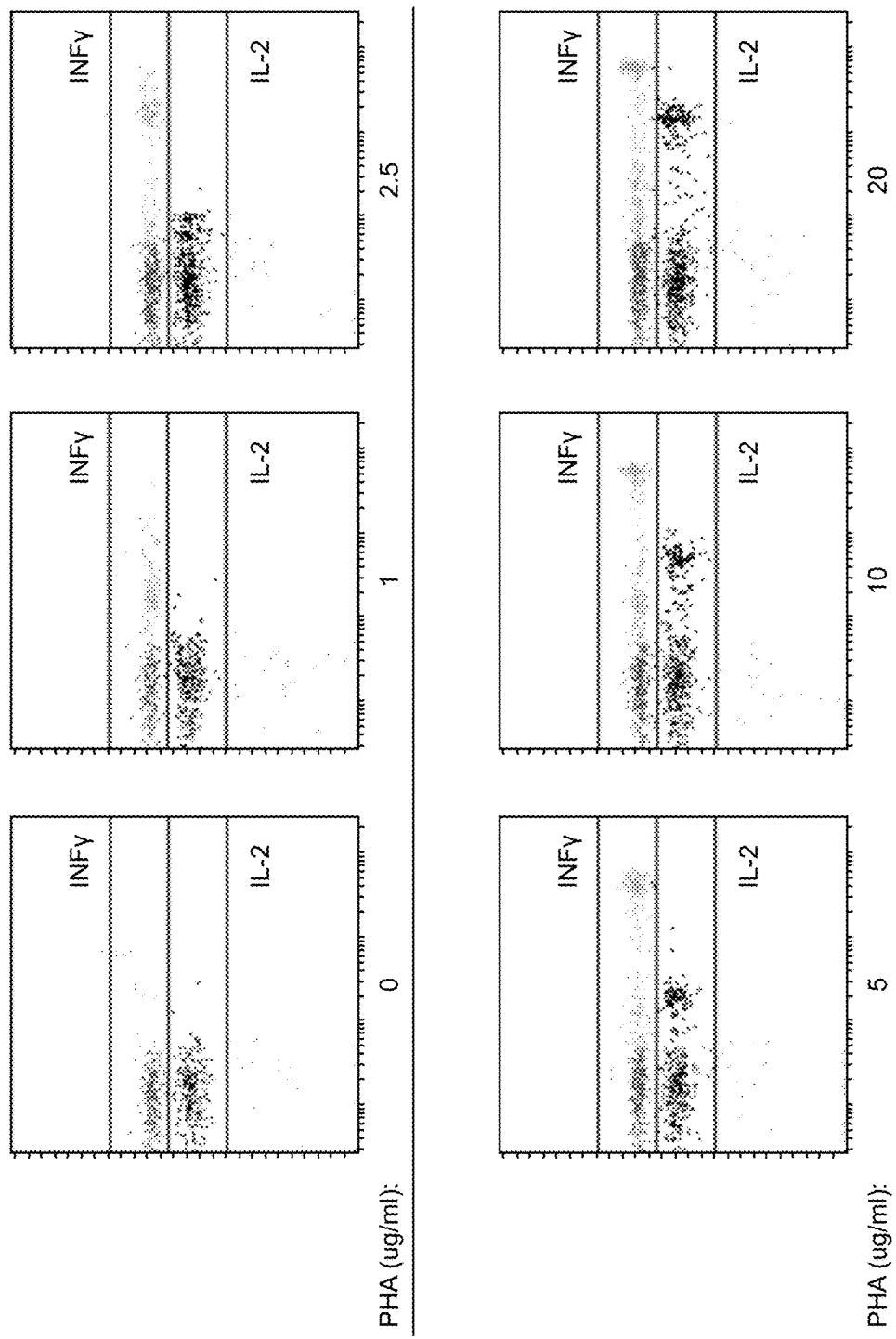
FIG. 6 provides flow cytometric data relating to two-color detection of IFNγ and interleukin-2 (IL-2) according to one embodiment of the present disclosure.

One hundred thousand C.T.L. cells were co-cultured with a mix of IFNγ and IL-2 capture microparticles (7,000 each with different fluorescent ID codes) for 16 h in the presence of PHA at various concentrations. FIG. 6 shows the dose-dependent responses of IFNγ and IL-2 to polyclonal T cell stimulus PHA.

Example 4: Three-Color IFNγ/IL-2/GrB (Granzyme B) Detection by FLOWSPOT

Figure 7:
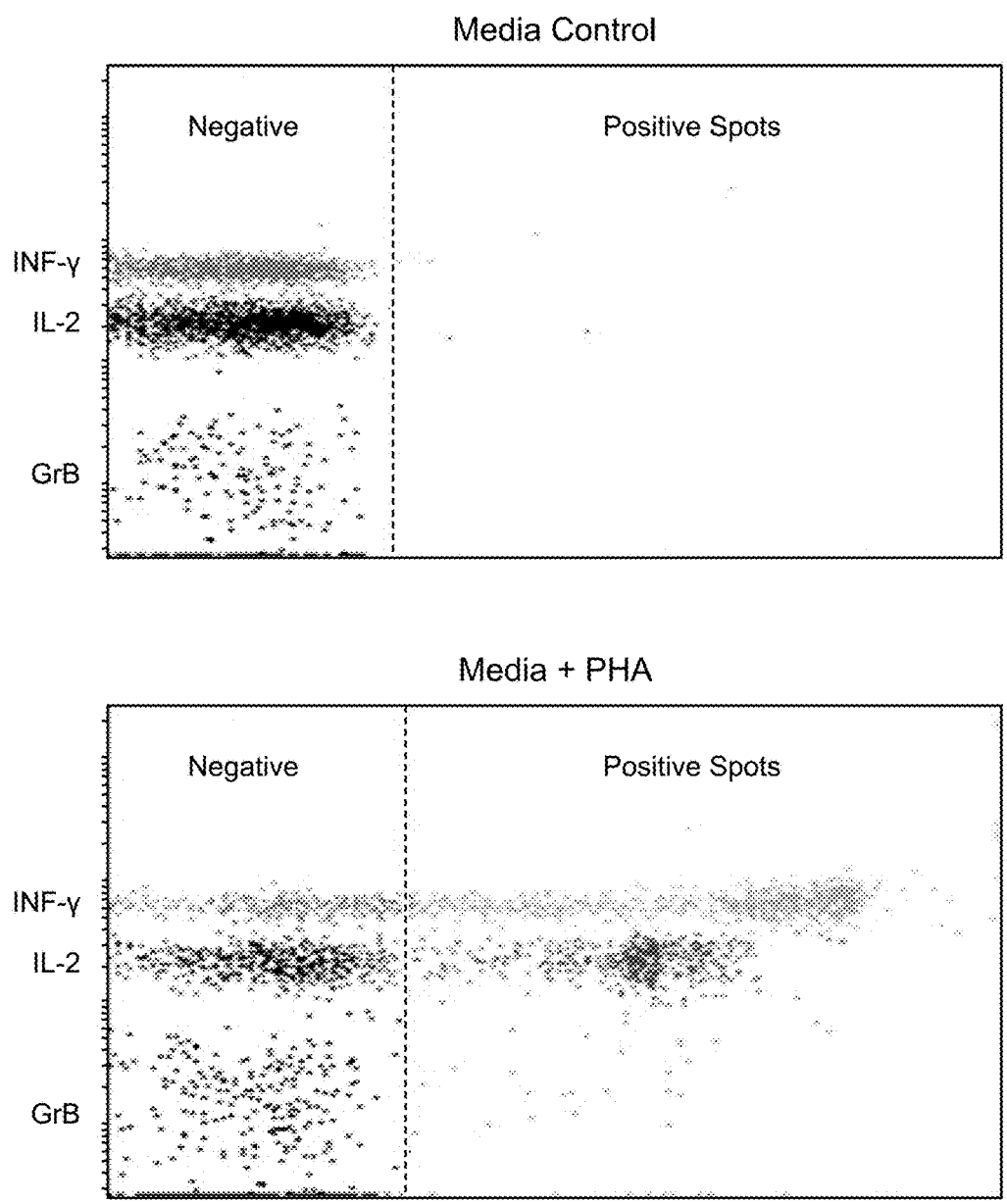
FIG. 7, Panels A and B, provides flow cytometric data relating to three-color detection of IFN-γ, IL-2 and Granzyme B (GrB) according to one embodiment of the present disclosure.
Figure 7:
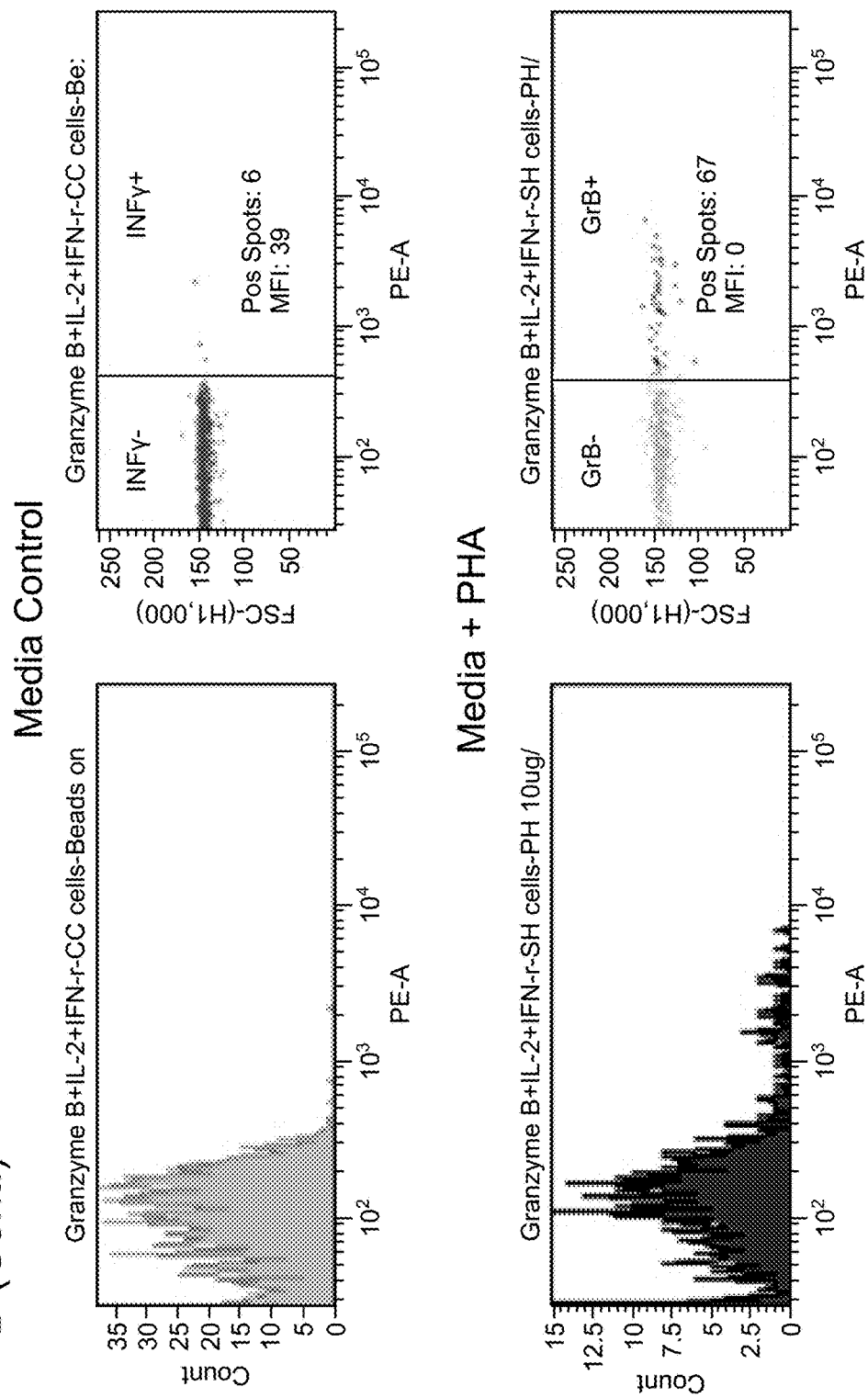

One hundred thousand PBMC cells were co-cultured with a mix of IFNγ, IL-2, and GrB capture microparticles (7,000 each with different fluorescent ID codes) for 16 h in the presence or absence of PHA (20 μg/mL). The captured IFNγ, IL-2, and GrB on microparticles were detected by a mix of corresponding PE-labeled antibodies (PE-anti-INF-γ, PE-anti-IL-2, and PE-anti-GrB, BD Bioscience). FIG. 7 shows the number of positive spots induced by PHA stimulation was 5,320 for IFNγ, 4,340 for IL-2, and 630 for GrB respectively. There were no more than 6 positive spots observed in the media controls. Results also showed that the intensity (amount) of IFNγ secretion was significantly greater than for IL-2 with median channel values (MCV) of 653 and 407, respectively. FIG. 5 shows that even when the percentage of positive cells is approximately the same [e.g., Flu-Matrix 1 (20%) and HCMV pp65 (19%)] the difference in intensity (FI) is significantly different (678 versus 25,286, respectively).

Example 5: HLA Antigen Memory B Cell Detection

Figure 9:
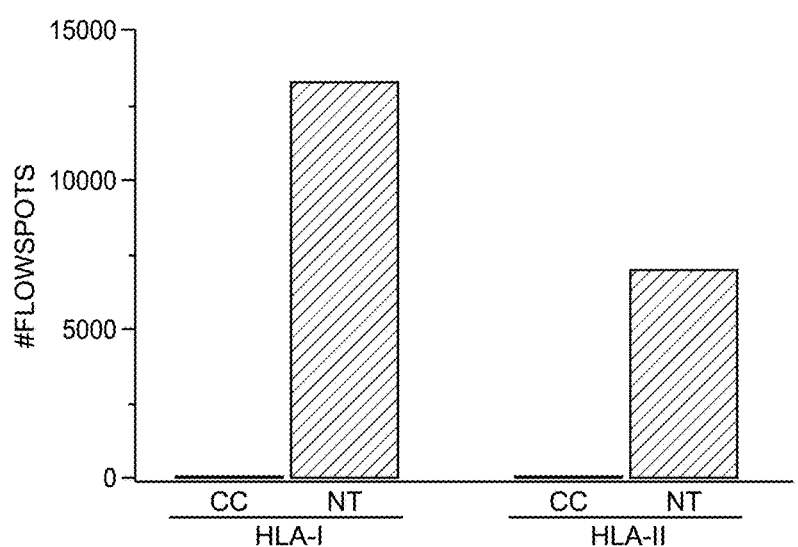
FIG. 9 shows data relating to HLA antigen specific memory B cell detection using the method illustrated in FIG. 8.
Figure 15:
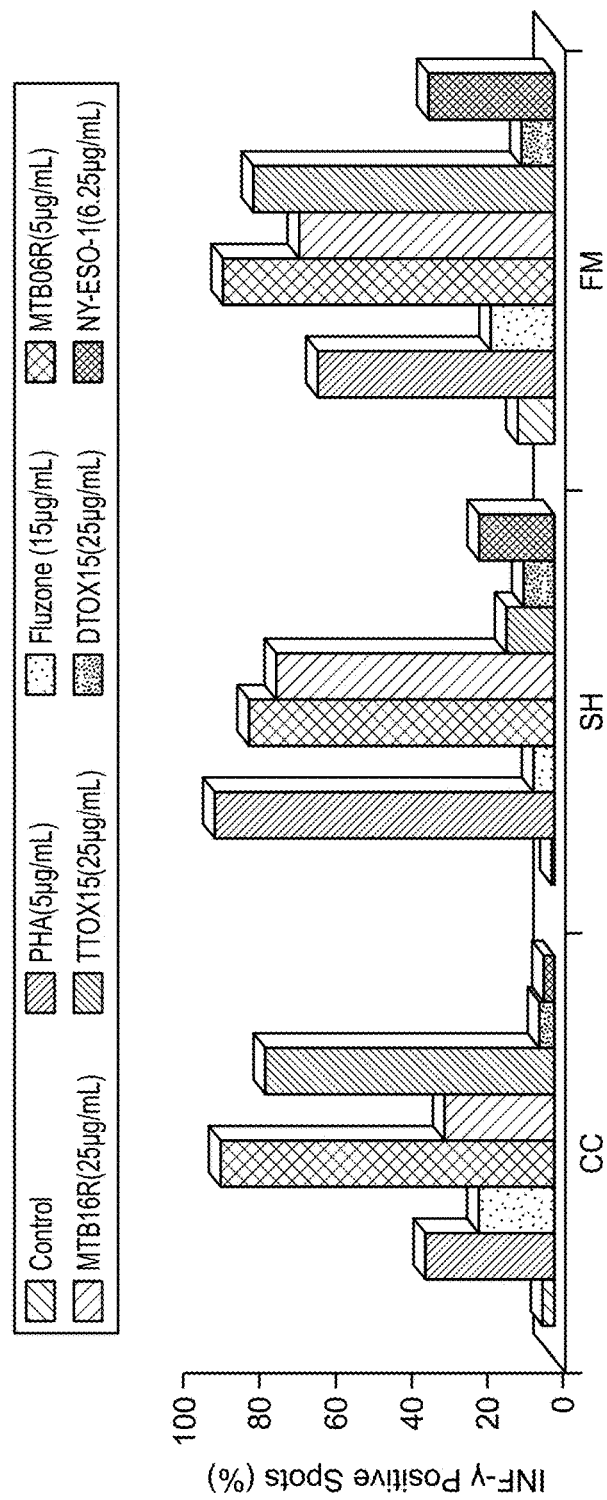
FIG. 15 shows data in which antigen-specific immunity to viral and bacterial peptides and proteins was assessed (based on IFN-γ secretion) using a method according to one embodiment of the present disclosure.
Figure 16:
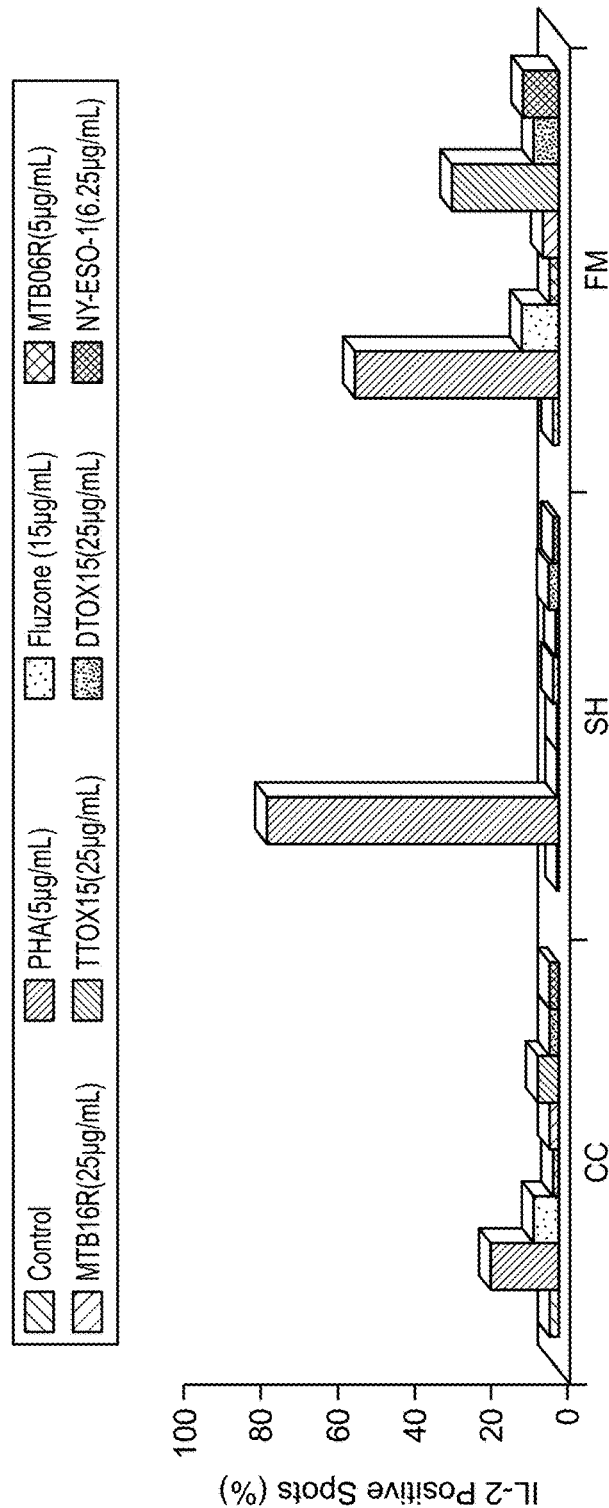
FIG. 16 shows data in which antigen-specific immunity to viral and bacterial peptides and proteins was assessed (based on IL-2 secretion) using a method according to one embodiment of the present disclosure.
Figure 17:
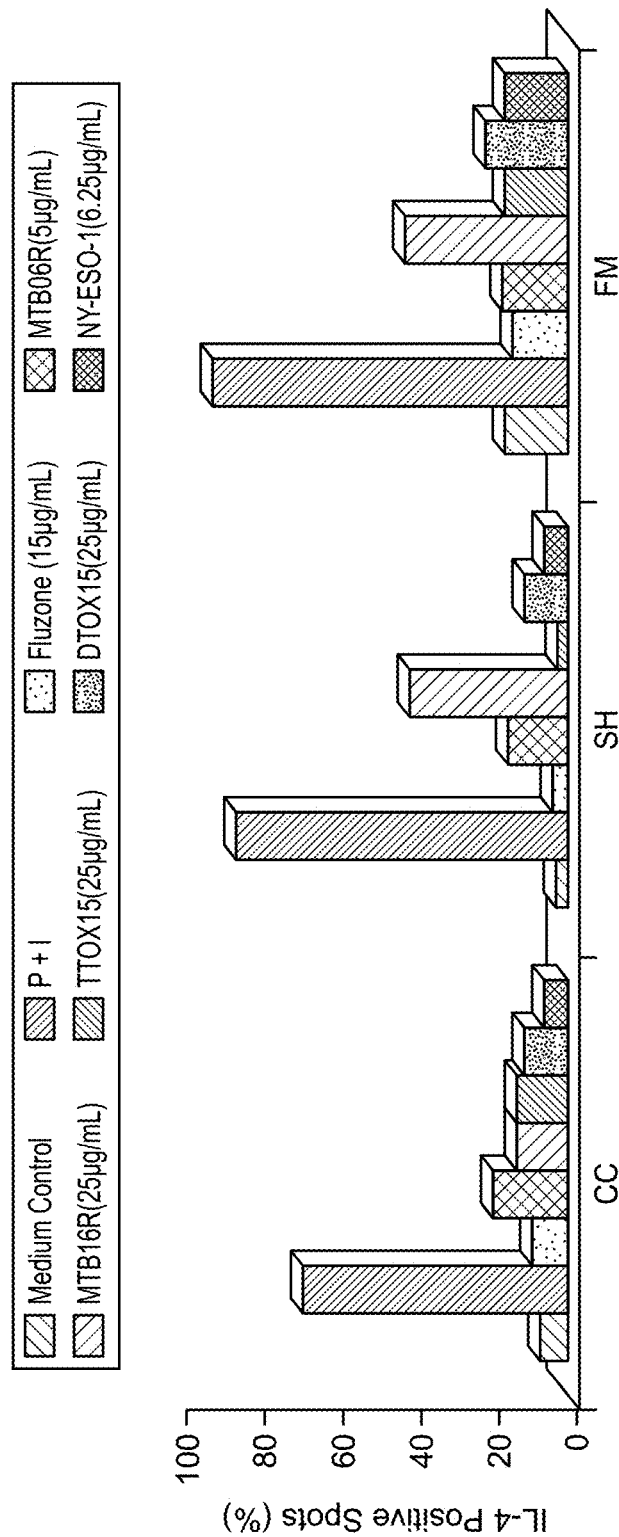
FIG. 17 shows data in which antigen-specific immunity to viral and bacterial peptides and proteins was assessed (based on IL-4 secretion) using a method according to one embodiment of the present disclosure.
Figure 18:
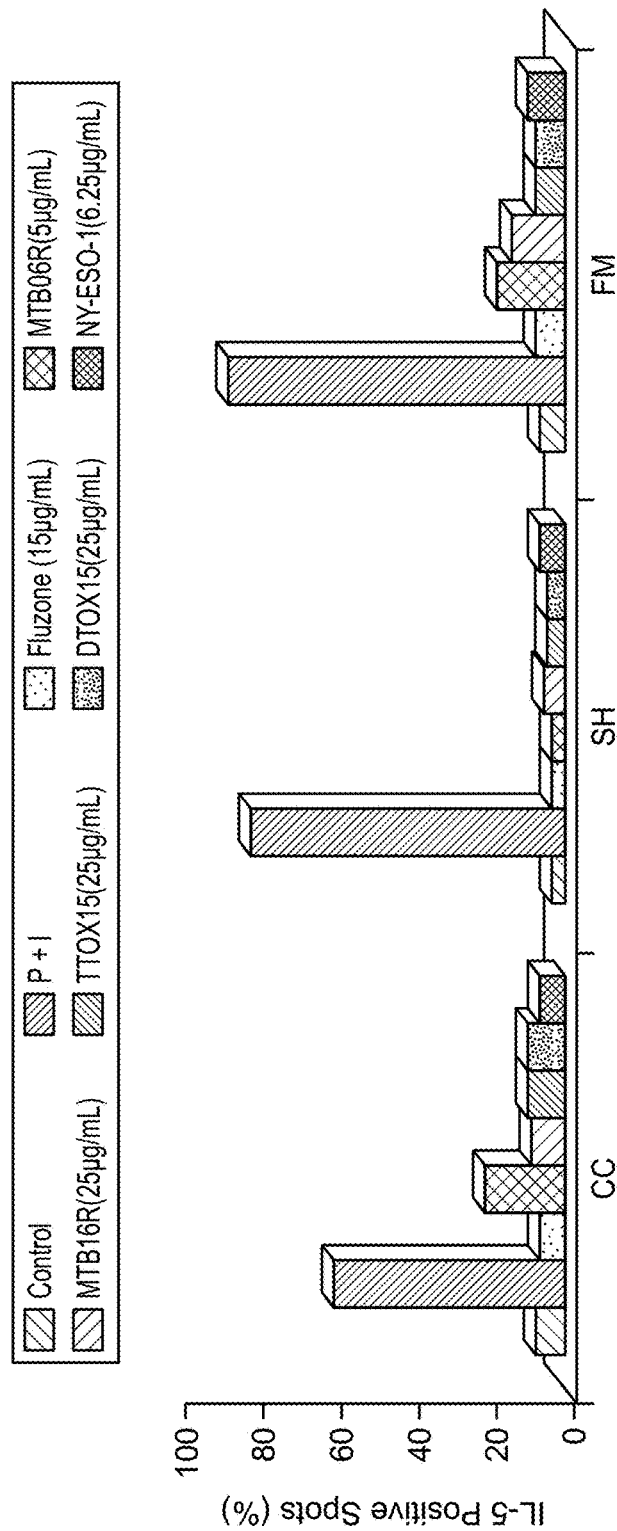
FIG. 18 shows data in which antigen-specific immunity to viral and bacterial peptides and proteins was assessed (based on IL-5 secretion) using a method according to one embodiment of the present disclosure.
Figure 19:
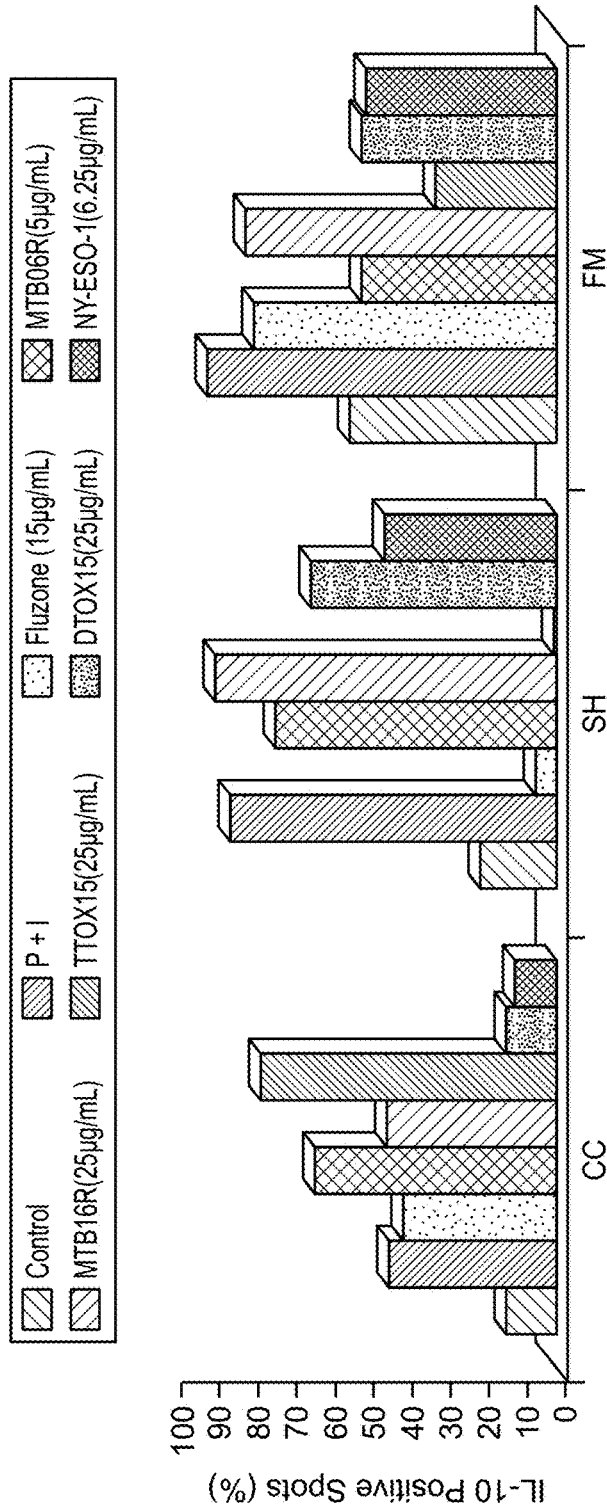
FIG. 19 shows data in which antigen-specific immunity to viral and bacterial peptides and proteins was assessed (based on IL-10 secretion) using a method according to one embodiment of the present disclosure.
Figure 20:
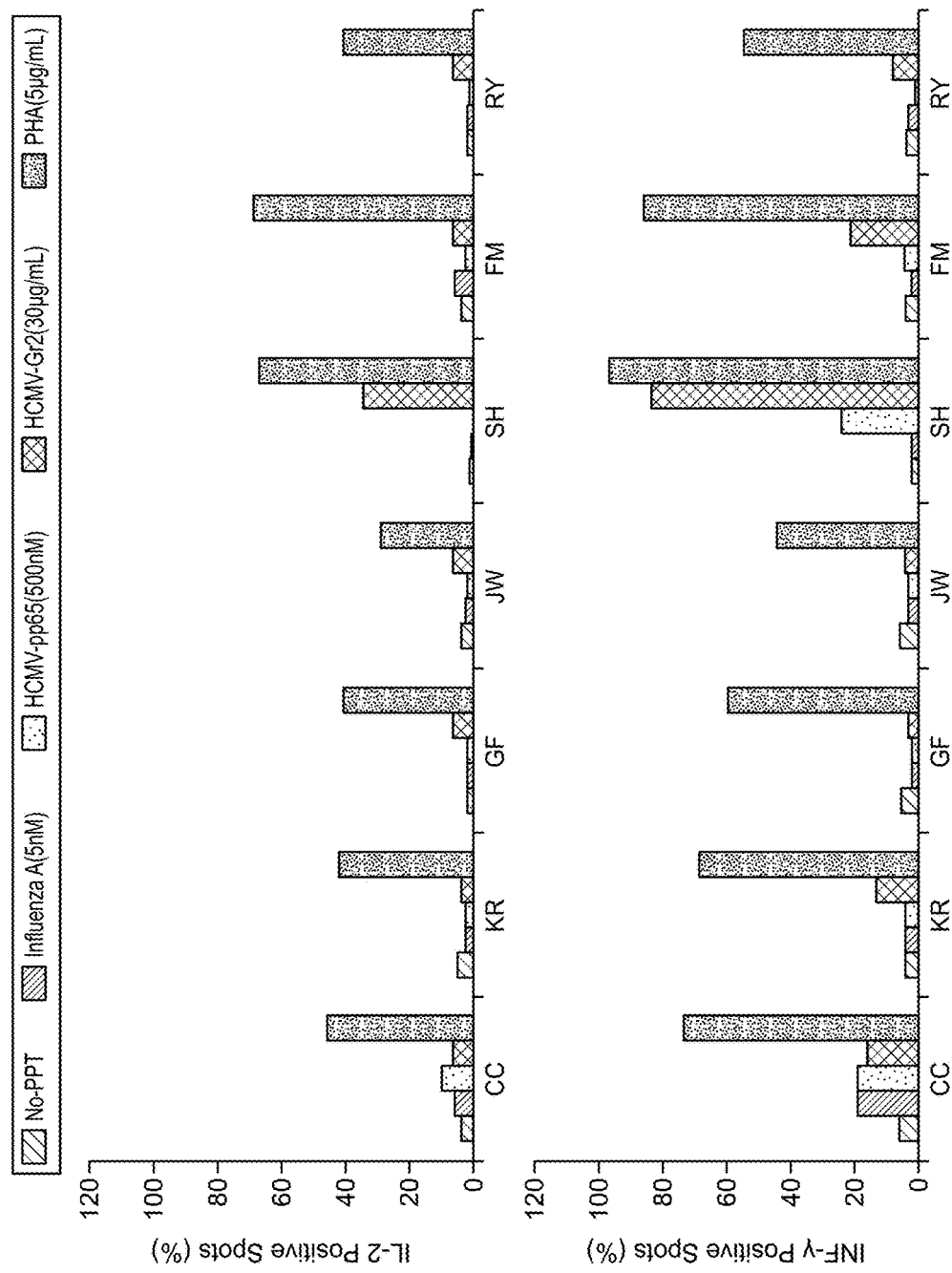
FIG. 20 shows data from seven individuals in which native viral peptide/antigen-specific T cell responses were assessed (based on IFN-γ and IL-2 secretion) using a method according to one embodiment of the present disclosure.
Figure 21:
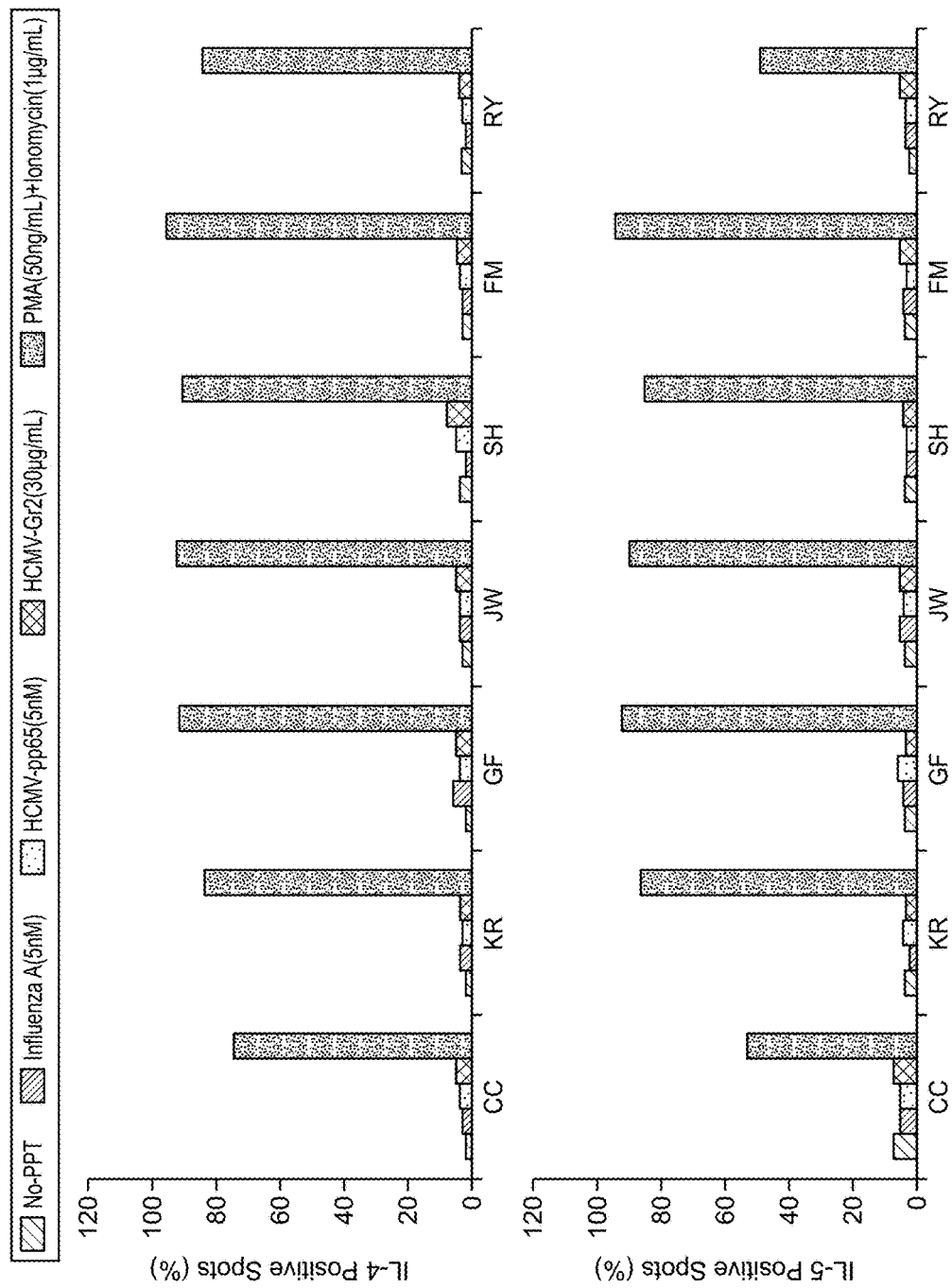
FIG. 21 shows data from seven individuals in which virus peptide/antigen-specific T cell responses were assessed (based on IL-4 and IL-5 secretion) using a method according to one embodiment of the present disclosure.
Figure 22:
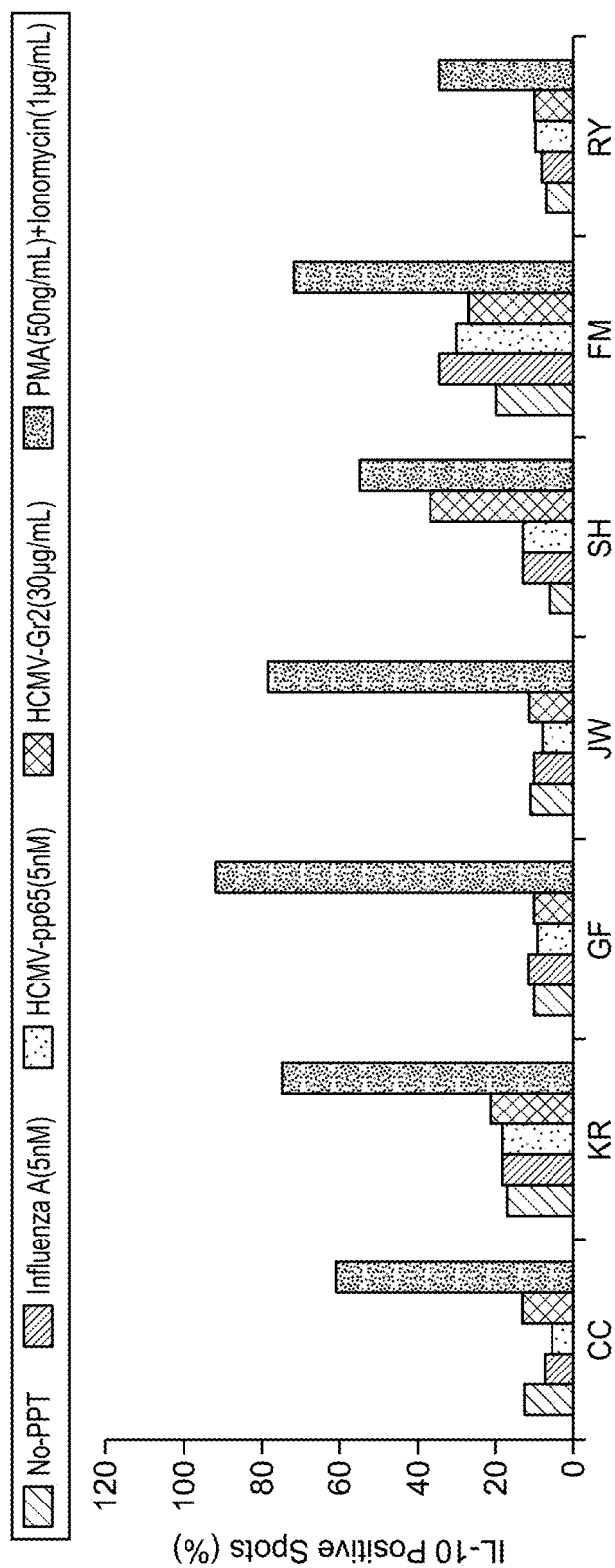
FIG. 22 shows data from seven individuals in which virus peptide/antigen-specific T cell responses were assessed (based on IL-10 secretion) using a method according to one embodiment of the present disclosure.

FIG. 8 depicts the principle of FLOWSPOT for antigen-specific memory B cell detection. One hundred thousand PBMC cells from donor NT with positive multiple specificity human leukocyte antigen (HLA) class I and II antibodies (HLA Class I Antibodies: A1, A2, A3, A9, A10, A11, A23, A24, A25, A26, A28, A34, A36, A43, A6602, A68, A69, A80; B8, B12, B14, B15, B16, B18, B21, B22, B35, B39, B40, B41, B45, B46, B50, B54, B55, B56, B60, B61, B62, B64, B65, B70, B71, B72, B75, B76, B78, B82, Bw4; Cw3, Cw9, Cw10; HLA Class II Antibodies: DR4, DR7, DRB, DR9, DR12, DRB3*01:01, DR3*03:01, DR53; DQA1*03; DPA1*02:01) or from donor CC with negative HLA antibody were co-cultured with single antigen Luminex beads coated with HLA class-I (147,000 microparticles/test; One Lambda) and -II antigens (139,000/test; One Lambda) for 6 days in a humidified 37° C., 5% $CO_2$ incubator. After cell lysis and washes, the HLA antibody bound on the HLA antigen beads was detected by adding 100 μL of PE-labeled Goat-anti human IgG (Jackson ImmunoResearch) and incubated at 22° C. for 30 min. The beads were washed and acquired on a FACSCanto II flow cytometer. As shown in FIG. 9, a total of 13,230 HLA class I and 6,975 HLA class II positive spots were detected on NT but none were detected with negative control CC cells (zero positive spots).

Example 6: Evaluation of Immunotherapeutic Drug Effects on Th1 and Th2 Cytokine Secretion by FLOWSPOT $0.1 \times 10^6$ lymphocytes were incubated with a mix of Th1 cytokine (IFN-γ and IL-2) or Th2 cytokine (IL-4, IL-5, and IL-10) capture microparticles (8,000/each with different fluorescent ID codes) in control media or the conditioned media containing various types of immunotherapeutic agents (Solumedrol 100 μM, Pharmacia & Upjohn Co.; Sirolimus 500 ng/mL, Wyeth pharmaceuticals Inc.; Prograf 100 ng/mL, Astellas Pharma US, Inc.; Infliximab 1 mg/mL, Janssen Biotech, Inc.) at 37° C. in a 5% $CO_2$ incubator for 16 h with and without adding PHA or P+I (50 ng/mL of PMA+1 μg/mL of Ionomycin). The cells were lysed with lysis buffer (50 mM Tris-HCl pH 7.4, 150 mM NaCl, 2 mM EDTA, 1% NP-40) and washed three times with 3% HBSA wash buffer (3% Bovine Serum Albumin in Hank's Balanced Salt Solution), the capture microparticles were then incubated with 50 μL detection antibodies mix (PE-anti-INF-γ, PE-anti-IL-2, PE-anti-IL-4, PE-anti-IL-5 and PE-anti-IL-10) from BD Bioscience at RT for 1 h with shaking. After three more washes, the microparticles were acquired and analyzed on a BD FACSCanto II flow cytometer. The result was expressed as a percentage of each of the different positive cytokine capture microparticles. FIG. 10-FIG. 14 depict the differential effects of the immunotherapeutic agents on the secretion of Th1 and Th2 cytokines.

Example 7: Evaluation of Specific Immunity to Virus Vaccine, Bacterial, and Tumor Antigens by FLOWSPOT $0.1 \times 10^6$ PBMC from each of three donors (CC, SH, and FM) were incubated with a mix of Th1 cytokine (IFN-γ and IL-2) or Th2 cytokine (IL-4, IL-5, and IL-10) capture microparticles (8000/each with different fluorescent ID codes) in control media or the conditioned media containing various types of antigens (45 μg/mL Fluzone, Sanofi Pasteur Inc.; 25 μg/mL of *Mycobacterium tuberculosis* Ag 6KDa, ADJ; 25 μg/mL of *Mycobacterium tuberculosis* Ag 16KDa, ADJ; 25 μg/mL of Tetanus Toxoid Protein, ADJ; 25 μg/mL of Diphtheria Toxoid Protein, ADJ; and 6.25 μg/mL of Testis Cancer Antigen, NY-ESO-1, JPT) at 37° C. in a 5% $CO_2$ incubator for 16 h. The cells were lysed with lysis buffer (50 mM Tris-HCl pH 7.4, 150 mM NaCl, 2 mM EDTA, 1% NP-40) and washed three times with wash buffer, the capture microparticles were then incubated with 50 μL mix of Th1 detection antibodies (PE-anti-INF-γ and PE-anti-IL-2) or Th2 detection antibody mix (PE-anti-IL-4, PE-anti-IL-5 and PE-anti-IL-10) at RT for 1 h with shaking. After three more washes, the microparticles were acquired and analyzed on a BD FACSCanto II flow cytometer. The final result (FIG. 15-FIG. 19) was expressed as percentage of positive microparticles compared to the total number of microparticle complexes. Results demonstrated that the specific immunities to various antigens of virus, bacteria, and tumor are significantly different in three donors.

Example 8: Detection of Virus Peptide/Antigen Specific T Cells Response by FLOWSPOT $0.1 \times 10^6$ PBMC from each of 7 blood donors were incubated with a mix of Th1 cytokine (IFN-γ and IL-2) or Th2 cytokine (IL-4, IL-5, and IL-10) capture microparticles (8000/each with different fluorescent ID codes) in control media or the conditioned media containing various types of virus peptides and antigen purchased from C.T.L. (5 nM Influenza A PA peptide, 500 nM HCMV-pp65, 30 μg/mL HCMV-Gr2 Ag) at 37° C. in a 5% $CO_2$ incubator for 16 h.

The cells were lysed with lysis buffer (50 mM Tris-HCl pH7.4, 150 mM NaCl, 2 mM EDTA, 1% NP-40) and washed three times with wash buffer, the capture microparticles were then incubated with 50 μL mix of Th1 detection antibodies (PE-anti-INF-γ and PE-anti-IL-2) or Th2 detection antibody mix (PE-anti-IL-4, PE-anti-IL-5 and PE-anti-IL-10) at RT for 1 h with shaking. After three more washes, the microparticles were acquired and analyzed on a BD FACSCanto II flow cytometer. The results (FIG. 5, FIG. 20-FIG. 22) show that the response patterns of Th1 and Th2 cytokine secretion varies in different donors against different virus peptides and antigens.

Example 9: Multiplex HLA Antigen Specific Memory B Cell Detection

Principle of Assay

FIG. 23 and FIG. 24 depict the principle of the assay, as described below. The biological sample containing memory B cells was incubated with a mix of uniquely labeled fluorescent beads, each conjugated with different purified HLA antigens. The HLA antigen specific memory B cells can be captured by the corresponding HLA antigen beads through the interaction of membrane B cell receptors (mBCR) and HLA antigens on the bead surface(s). After cell lysis, the captured mBCR on each HLA antigen bead can be detected by fluorescent anti-immunoglobulin in a flow cytometer. The number and fluorescence intensity of positive beads are proportional to the number of HLA antigen specific memory B cells.

Methods and Results

Figure 25:
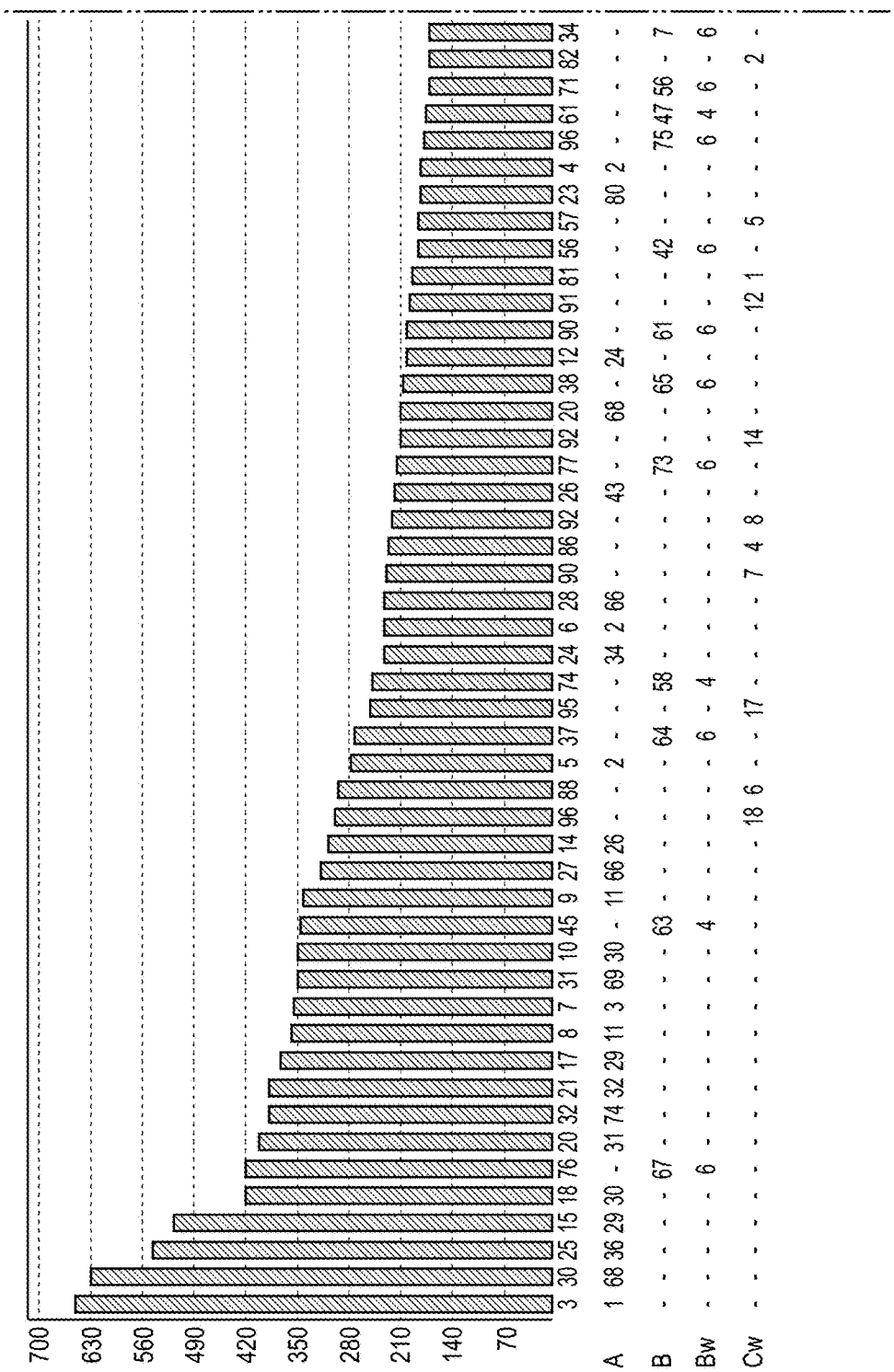
FIG. 25 shows the results of a multiplex HLA antigen-specific memory B cell assay as illustrated in FIGS. 23 and 24.
Figure 25:
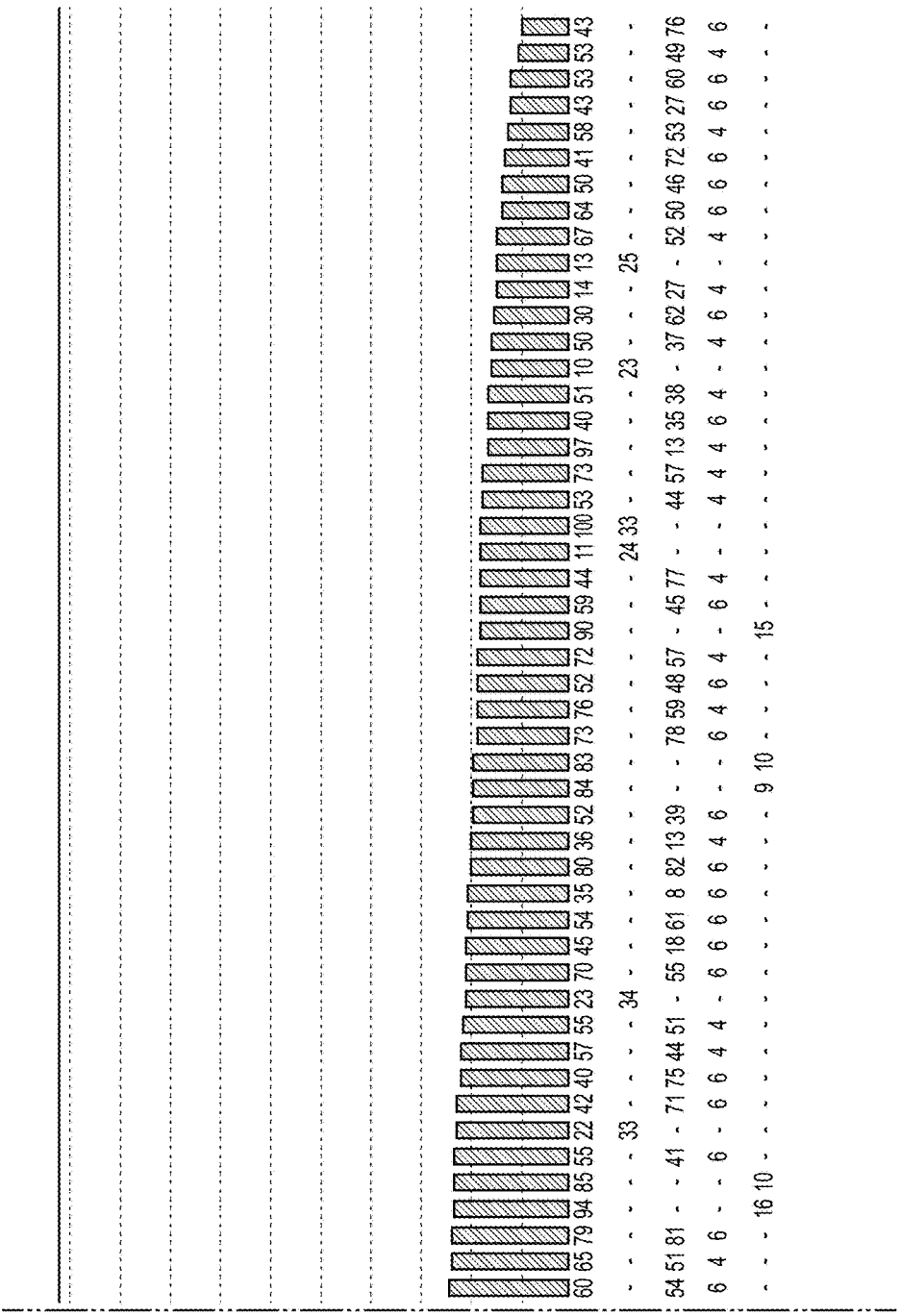
Figure 26:
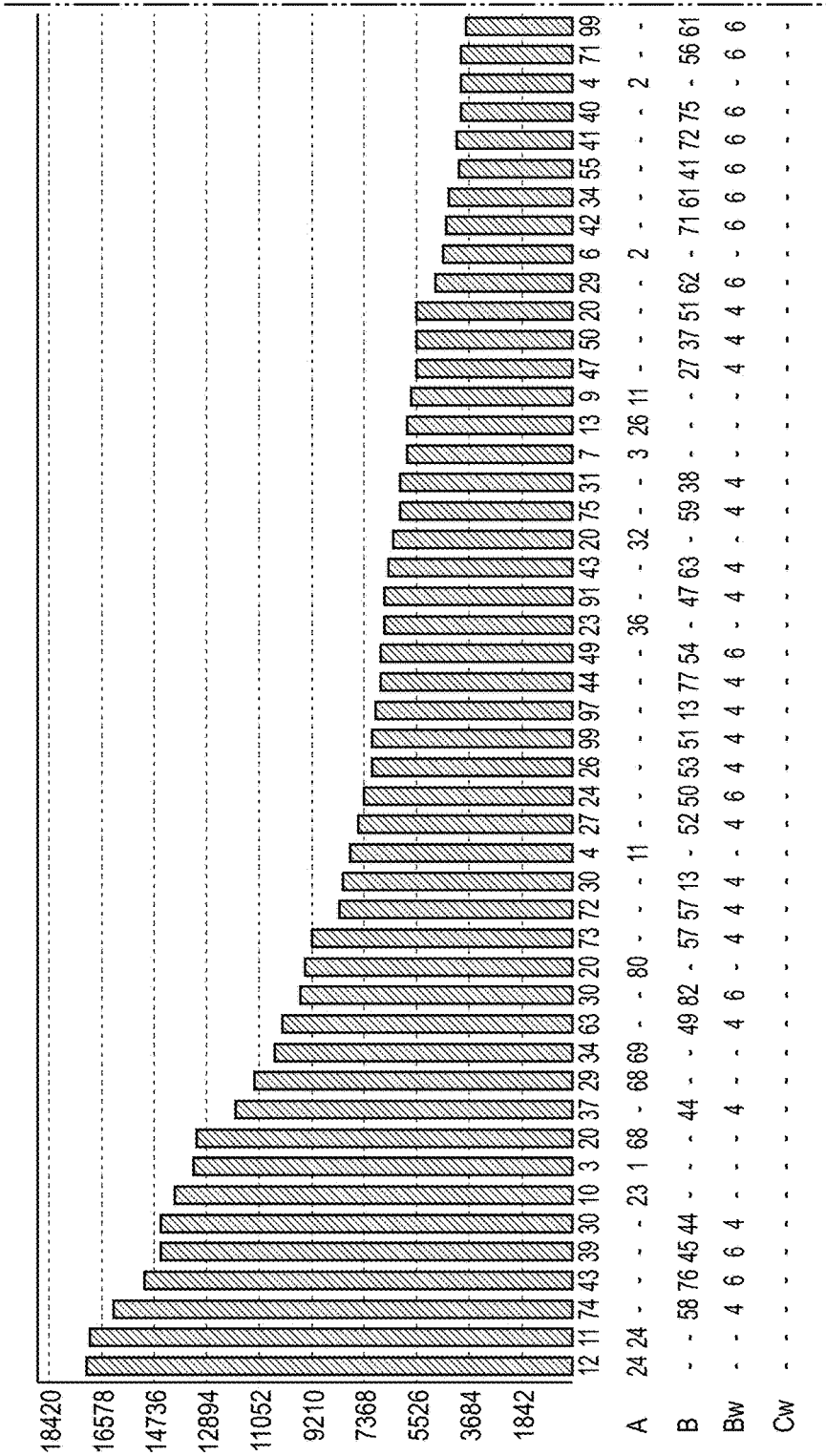
FIG. 26 shows the results of a multiplex HLA antigen-specific memory B cell assay as illustrated in FIGS. 23 and 24.
Figure 26:
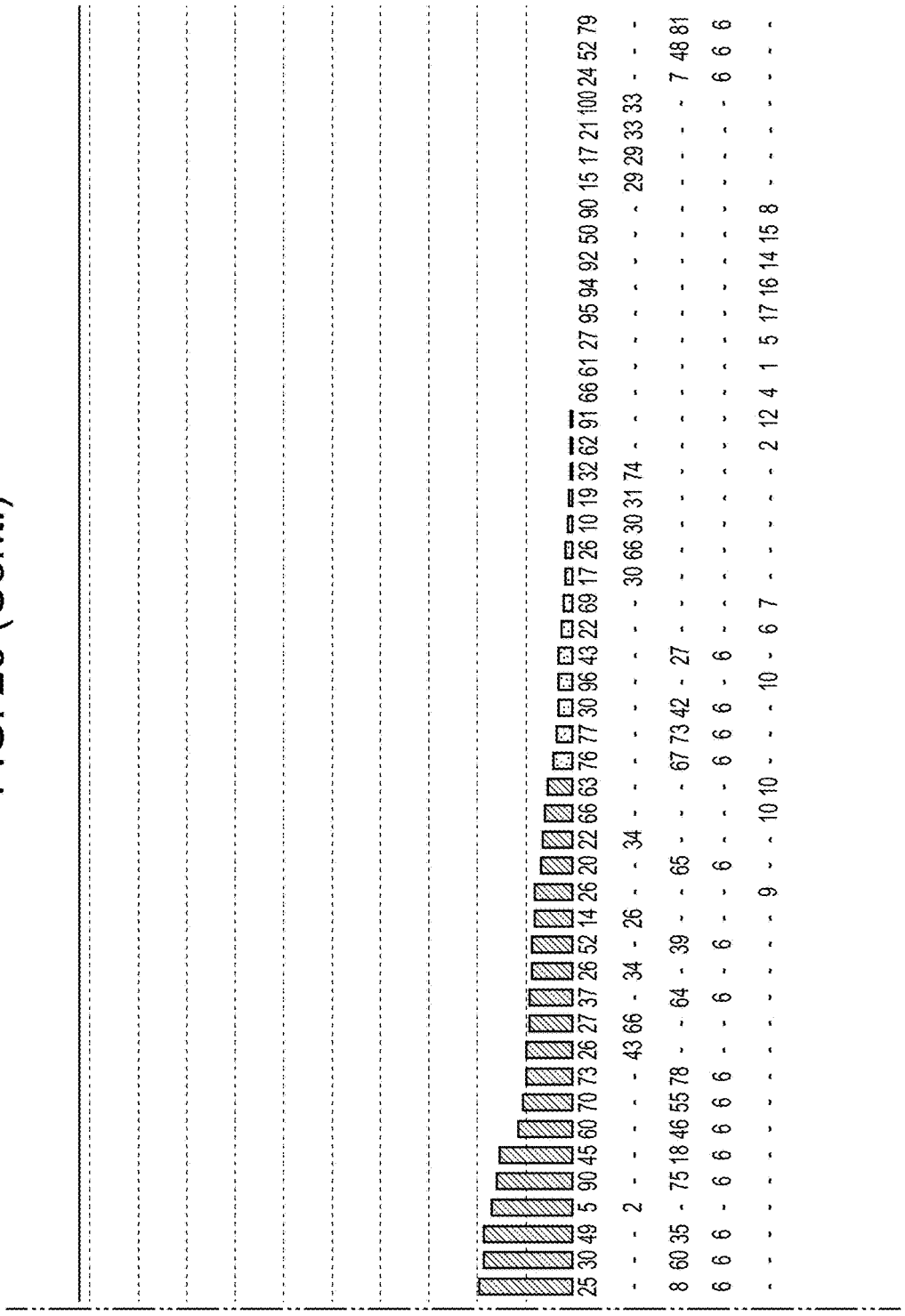

One hundred thousand PBMC cells from donors positive (NT) (FIG. 26) or negative (RT) (FIG. 25) for multiple HLA class I antibody specificities (HLA Class I Antibodies: A1, A2, A3, A9, A10, A11, A23, A24, A25, A26, A28, A32, A34, A36, A43, A6602, A68, A69, A80; B8, B12, B14, B15, B16, B18, B21, B22, B35, B39, B40, B41, B45, B46, B50, B54, B55, B56, B60, B61, B62, B64, B65, B70, B71, B72, B75, B76, B78, B82, Bw4; Cw3, Cw9, Cw10) were co-cultured independently and concurrently with 97 single HLA class-I antigens coated Luminex beads (147,000 beads/test; One Lambda) for 16 h in a humidified 37° C., 5% $CO_2$ incubator. After cell lysis and washes, the HLA antibodies secreted from plasma cells and/or IgG B cell receptors (BCR) bound on each single HLA antigen beads were labeled by adding 100 uL of PE-labeled Goat-anti human IgG (Jackson ImmunoResearch) and incubated at 22° C. for 30 min. The final washed beads were acquired on a FACSCanto II flow cytometer. The (97) bead populations were gated on a dot plot and the percentage of positive FLOWSPOTS on each single HLA antigen bead population was calculated by using Diva software (BD Biosciences).

Figure 27:
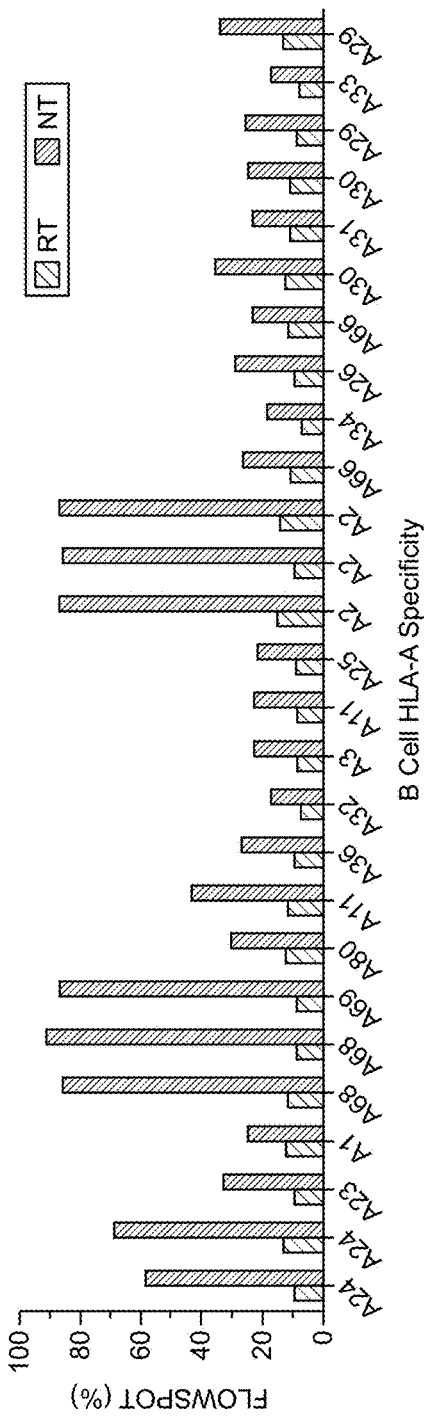
FIG. 27 shows the results of a multiplex HLA antigen-specific memory B cell assay as illustrated in FIGS. 23 and 24.
Figure 28:
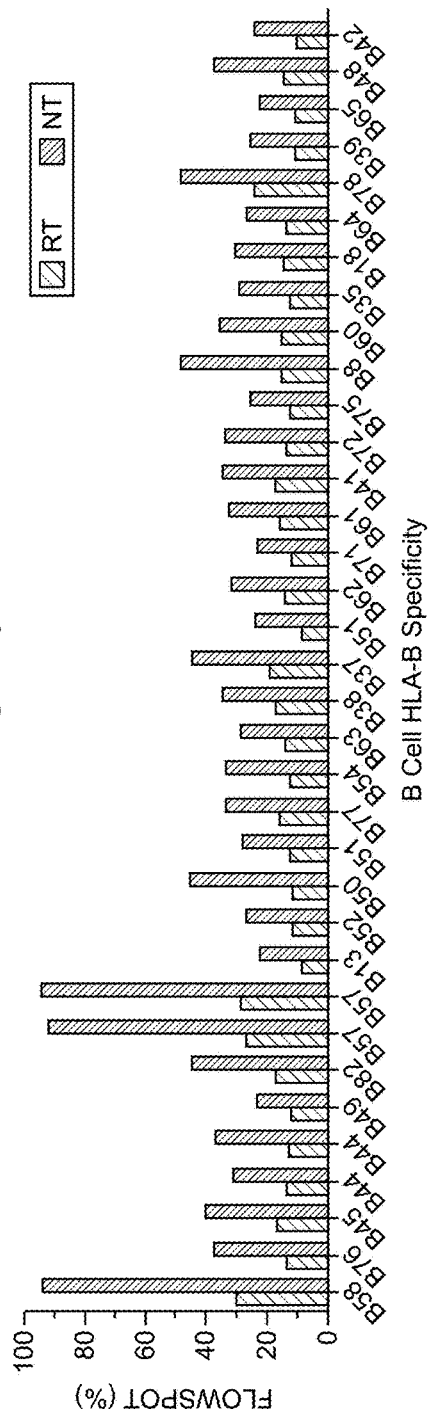
FIG. 28 shows the results of a multiplex HLA antigen-specific memory B cell assay as illustrated in FIGS. 23 and 24.

A total of 27 HLA-A (FIG. 27) and 35 HLA-B (FIG. 28) specific bead populations were detected positive by FLOWSPOT in NT cells but negative in RT cells. The positive FLOWSPOT populations were concordant with serum HLA antibody screening results by Luminex single antigen beads assay.

Example 10: INF-γ Secretion Detection by CBA and FlowSpot

Cytometric Bead Array (CBA): INF-γ Secretion Detection in Culture Media

Figure 29:
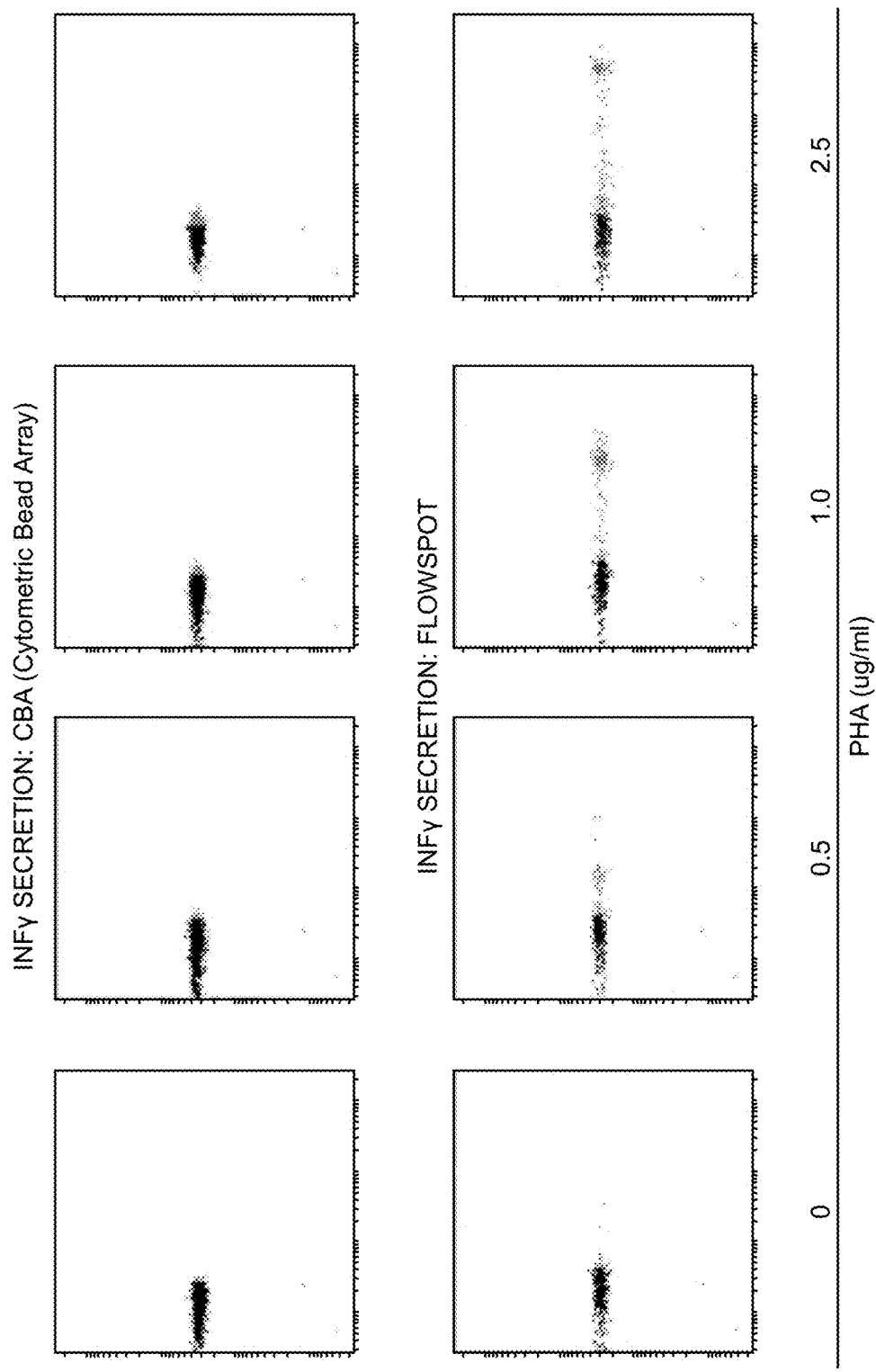
FIG. 29 provides flow cytometry data comparing the results of a cytometric bead array (CBA) assay to the results produced using a FlowSpot assay according to one embodiment of the present disclosure.
Figure 29:
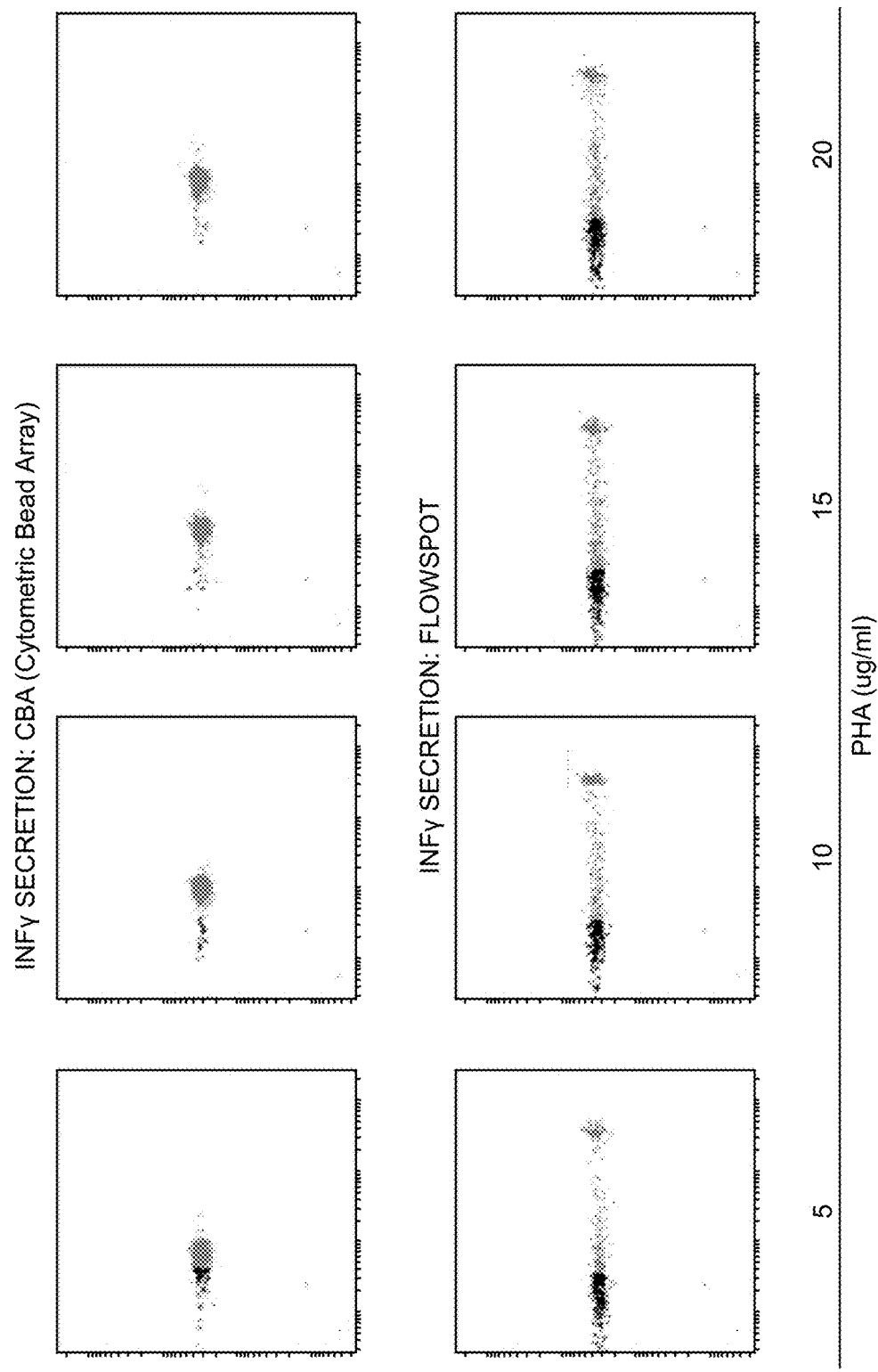

One hundred thousand peripheral blood mononuclear cells ($0.1 \times 10^6$ PBMC) in 100 μL of 10% FBS RPMI 1640 containing varying concentrations of PHA were seeded in each well in a 96 well plate and incubated in a humidified 37° C., 5% $CO_2$ incubator for 16 h. The plate was centrifuged at 2,500 g for 3 min and 50 μL culture medium of each well was carefully transferred into each corresponding test well in a new 96 well plate. After adding 50 μL INFγ capture beads (BD Biosciences; Cat. 558269) into each well, the plate was incubated at room temperature (RT) for 60 min with constant shaking on a plate shaker. After adding 50 μL INFγ PE-detection reagents (BD Biosciences; Cat. 51-9004031), the plate was continually incubated at RT for additional 2 h. The beads were then washed three times with 200 μL wash buffer (0.05% Tween-20 in PBS) and acquired on a BD FACSCanto II flow cytometer. The concentrations of INFγ in the culture media from each well were extrapolated from the standard curve generated from a series of known INFγ standards in the same batch of CBA assay. Results are shown in FIG. 29.

FlowSpot: INF-γ Secretion In Situ Detection

In parallel, $0.1 \times 10^6$ PBMC cells from the same donor were co-cultured with 7,000 IFNγ capture microparticles in a humidified 37° C., 5% $CO_2$ incubator for 16 h in the presence of PHA at various concentrations. After incubation, the cells were lysed in NP-40 lysis buffer (10 mM Tris-HCl, pH 7.4, 10 mM NaCl, 3 mM $MgCl_2$, 0.5% NP-40). The capture beads were washed twice with 3% HBSA (3% BSA in HBSS) and incubated with 50 μL PE-labeled anti-IFNγ for 60 min at room temperature. After an additional two washes of 3% HBSA, the beads were acquired and analyzed on a BD FACSCanto II flow cytometer. The number of positive spots is calculated based on the previously described formulas, and results are shown in FIG. 29.

A comparison of IFNγ Detection by FLOWSPOT and CBA is shown in Table 1 below.

TABLE 1

Comparison of IFNγ Detection by FLOWSPOT and CBA
Comparison of IFNγ Detection by FLOWSPOT and CBA

| PHA (μg/mL) | FLOWSPOT | | | CBA |
|---|---|---|---|---|
| | % Positive Spot | SPOTS (n) | MFI | IFNγ (pg/ml) |
| 0 | 0 | 0 | 0 | 10 |
| 0.5 | 24 | 1680 | 166 | 17 |
| 1 | 35 | 2450 | 659 | 36 |
| 2.5 | 43 | 3010 | 4050 | 76 |
| 5 | 45 | 3150 | 9541 | 174 |
| 10 | 56 | 3920 | 19594 | 281 |
| 15 | 57 | 3990 | 21680 | 344 |
| 20 | 55 | 3850 | 22241 | 312 |

The BD™ Cytometric Bead Array (CBA) is a multiplex detection system to quantify multiple proteins in a biological sample simultaneously. CBA is a uniform (homogeneous) testing system in which the analytes are evenly distributed in a liquid sample and all capture microparticles have a same probability to capture the analytes. In contrast to CBA, Flowspot is a non-uniform (or inhomogeneous) detection system. Depending on the distribution of microparticles and cells, the capture microparticles adjacent to the biomarker secreting cells (e.g., responding cells) have a higher probability, due to proximity, to capture the biomarkers secreted from the responding cells than the cells that are distant from the responding cells, as well as a higher probability to saturate more of the capture ligands due to high proximal biomarker concentration. Therefore, the percentage of positive reacting microparticles is proportionately correlated to the number of reacting cells; and the fluorescence intensity of positive microparticles reflects the relative biomarker secreting capability of the responding cells. Compared to CBA, Flowspot is more sensitive and more specific.

Example 11: Evaluation of Specific Immunity to Donor Cells by Flowspot

Recipient (R) Cells:
HLA Type: A*02:01, 03:01; B*07:02, 37:01; Bw4, w6; C*06:02, 07:02; DRB1*15:01, X; DR51; DQB1*06:02, X; DPB1*02:01, 04:01; DPA1*01:03/10, X Donor (D) Cells:
HLA Type: A*26:01, 30:01; B*13:02, 38:01; Bw4; C*06:02, 12:03; DRB1*04:03, 13:01; DR52, 53; DQB1*03:05, 06:03; DPB1*02:01, 04:01

Procedure:
$0.1 \times 10^6$ of recipient, R, PBMCs were co-cultured with an equal number of 50 Gy gamma irradiated autologous (iR) or donor (iD) PBMCs and a mix of Th1 cytokine (IFN-γ and IL-2) capture microparticles (8,000/each with different fluorescent ID codes) at 37° C. in a 5% $CO_2$ incubator for 72 h. The cells were lysed with lysis buffer (50 mM Tris-HCl pH 7.4, 150 mM NaCl, 2 mM EDTA, 1% NP-40) and washed three times with 3% HBSA wash buffer (3% Bovine Serum Albumin in Hank's Balanced Salt Solution). The capture microparticles were then incubated with 50 µL detection antibodies mix (PE-anti-INF-γ and PE-anti-IL-2) from BD Bioscience at RT for 1 h with shaking. After three more washes, the microparticles were acquired and analyzed on a BD FACSCanto II flow cytometer. The results were expressed as the percent positive of the total and the median fluorescent intensity (MFI) for each of the different cytokine capture microparticles.

As shown in FIG. 30, the recipient has a negative response to irradiated autologous cells (R+iR) but a strong positive response to irradiated donor cells (R+iD) for both interferon gamma (IFN-γ) and interleukin-2 (IL-2) secretion.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A method for detecting a biomarker, comprising:
co-culturing:
a cell; and
a microparticle comprising a capture ligand,
in a culture medium under conditions in which a biomarker secreted by the cell is bound by the capture ligand, and
detecting presence of the bound biomarker.

2. The method according to claim 1, wherein the biomarker is selected from the group consisting of: a cytokine, an immunoglobulin, a hormone, a growth factor, an enzyme, a protease, a protein, an allergen, a peptide, a nucleic acid, a drug, a cluster differentiation (CD) molecule, a tumor marker, a receptor, and combinations thereof.

3. The method according to claim 2, wherein the biomarker is a cytokine selected from the group consisting of: an interferon, a chemokine, an interleukin, a lymphokine, a tumor necrosis factor, and combinations thereof.

4. The method according to claim 1, wherein the method comprises stimulating the cell to secrete the biomarker.

5. The method according to claim 4, wherein stimulating the cell to secrete the biomarker comprises adding a stimulant to the culture medium.

6. The method according to claim 5, wherein the stimulant is selected from the group consisting of: an antigen, a ligand, a protein, a glycoprotein, a peptide, a lectin, a nucleic acid, a cell, a sub-cellular component, a microorganism, an allergen, a drug, an interferon, a chemokine, an interleukin, a CD molecule, a chemical compound, an agonist, an antagonist, and combinations thereof.

7. The method according to claim 1, wherein the cell and the microparticle are co-cultured in the presence of cells that are not stimulated to secrete the biomarker.

8. The method according to claim 1, wherein the cell is of a type selected from: a peripheral blood mononuclear cell (PBMC), a white cell, a tumor cell, a stem cell, an immune cell, a lymphocyte, a T cell, a B cell, a natural killer (NK) cell, a natural killer T (NKT) cell, a macrophage, a dendritic cell, a monocyte, a granulocyte, an epithelial cell, an endothelial cell, and a platelet.

9. The method according to claim 1, wherein the biomarker is present on the surface of the cell.

10. The method according to claim 9, wherein the biomarker is a cell surface receptor.

11. The method according to claim 10, wherein the cell surface receptor is an immunoglobulin.

12. The method according to claim 11, wherein the cell is a memory B cell.

13. The method according to claim 1, wherein the microparticle comprises a material selected from the group consisting of: latex, polystyrene, silica, a magnetic material, a paramagnetic material, and combinations thereof.

14. The method according to claim 1, wherein the microparticle has a greatest dimension of from 0.001 µm to 20 µm.

15. The method according to claim 1, wherein the capture ligand is selected from the group consisting of: an antibody, an antigen, a protein, an enzyme, a substrate, an allergen, a peptide, a nucleic acid, a drug, a chemical compound, a carbohydrate, and combinations thereof.

16. The method according to claim 1, further comprising, after the biomarker is bound by the capture ligand, lysing the cell.

17. The method according to claim 1, further comprising, after the biomarker is bound by the capture ligand, contacting the biomarker with a detection reagent to form a complex comprising the microparticle, the capture ligand, the biomarker, and the detection reagent.

18. The method according to claim 17, wherein the detection reagent is a reagent that specifically binds the biomarker.

19. The method according to claim 18, wherein the detection reagent is selected from the group consisting of: an antibody, an antigen, a ligand, a protein, an allergen, a peptide, a receptor, an enzyme, a substrate, a nucleic acid, a drug, a chemical compound, a carbohydrate, and combinations thereof.

20. The method according to claim 18, wherein the detection reagent comprises a detectable label.

21. The method according to claim 20, wherein the detectable label is selected from the group consisting of: a fluorescent label, a radiolabel, a luminescent agent, and a metal element label.

22. The method according to claim 17, further comprising detecting the complex.

23. The method according to claim 22, wherein the detecting is by flow cytometry.

24. The method according to claim 22, wherein the detecting is by mass cytometry.

25. The method according to claim 22, wherein the detecting comprises counting the number of positive complexes.

26. The method according to claim 22, comprising determining a signal intensity of each detected complex.

27. The method according to claim 26, comprising determining a level of the biomarker based on the mean or median signal intensity of the detected complexes.

* * * * *